United States Patent
Frey et al.

(10) Patent No.: US 9,198,678 B2
(45) Date of Patent: *Dec. 1, 2015

(54) PATIENT-MATCHED APPARATUS AND METHODS FOR PERFORMING SURGICAL PROCEDURES

(71) Applicants: George Frey, Englewood, CO (US); Benjamin Majors, Denver, CO (US); Charles O'Neil, Littleton, CO (US); Geoff Lai, Lakewood, CO (US); Russ Rydin, Highlands Ranch, CO (US)

(72) Inventors: George Frey, Englewood, CO (US); Benjamin Majors, Denver, CO (US); Charles O'Neil, Littleton, CO (US); Geoff Lai, Lakewood, CO (US); Russ Rydin, Highlands Ranch, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/298,634

(22) Filed: Jun. 6, 2014

(65) Prior Publication Data

US 2014/0350614 A1 Nov. 27, 2014

Related U.S. Application Data

(63) Continuation-in-part of application No. 13/841,069, filed on Mar. 15, 2013, now Pat. No. 8,870,889.

(60) Provisional application No. 61/832,583, filed on Jun. 7, 2013, provisional application No. 61/845,463, filed on Jul. 12, 2013, provisional application No. 61/877,837, filed on Sep. 13, 2013.

(51) Int. Cl.
*A61B 17/58* (2006.01)
*A61B 17/17* (2006.01)
(Continued)

(52) U.S. Cl.
CPC ............... *A61B 17/1757* (2013.01); *A61B 5/05* (2013.01); *A61B 17/15* (2013.01); *A61B 17/151* (2013.01);
(Continued)

(58) Field of Classification Search
CPC ................... A61B 2017/00526; A61B 17/155; A61B 17/157; A61B 2017/568; A61B 17/151; A61B 19/50; A61B 17/15; A61B 17/1671; A61B 17/70; A61B 17/7047; A61B 17/8863; A61B 2019/0278; A61B 2019/508; Y10T 409/30084; A61F 2/30965; A61F 2/4405; A61F 2/4611; A61F 2002/3095; A61F 2002/30952; A61F 2002/4687; A61F 2310/00017; A61F 2310/00023; A61F 2310/00029; A61F 2310/00047; A61F 2310/00059; G06F 17/50; G09B 23/30
USPC ........ 600/407–430, 437–469; 606/79, 88–96; 602/26
See application file for complete search history.

(56) References Cited

U.S. PATENT DOCUMENTS 3,151,392 A 10/1964 Chambers
5,201,734 A 4/1993 Cozad et al.
(Continued)

FOREIGN PATENT DOCUMENTS

CN 201275138 7/2009
CN 201404283 2/2010
(Continued)

OTHER PUBLICATIONS

Official Action for China Patent Application No. 201180029692.7, mailed Oct. 8, 2014 12 pages.
(Continued)

*Primary Examiner* — Sanjay Cattungal
(74) *Attorney, Agent, or Firm* — Sheridan Ross P.C.

(57) ABSTRACT

A system and method for developing customized apparatus for use in one or more surgical procedures is disclosed. The system and method incorporates a patient's unique anatomical features or morphology. According to a preferred embodiment, the customized apparatus comprises a plurality of complementary surfaces. Thus, each apparatus may be matched and oriented around the patient's own anatomy, and may further provide any desired axial alignments or insertional trajectories. In an alternate embodiment, the apparatus may further be aligned and/or matched with at least one other apparatus used during the surgical procedure.

19 Claims, 108 Drawing Sheets

(51) Int. Cl.

| | | |
|---|---|---|
| *A61B 5/05* | (2006.01) | |
| *A61B 17/15* | (2006.01) | |
| *A61B 17/70* | (2006.01) | |
| *A61B 17/88* | (2006.01) | |
| *A61B 19/02* | (2006.01) | |
| *A61B 19/00* | (2006.01) | |
| *A61F 2/46* | (2006.01) | |
| *G06F 17/50* | (2006.01) | |
| *G09B 23/30* | (2006.01) | |
| *A61B 17/16* | (2006.01) | |
| *A61B 17/56* | (2006.01) | |
| *A61F 2/30* | (2006.01) | |
| *A61F 2/44* | (2006.01) | |

(52) U.S. Cl.
CPC ............ *A61B 17/70* (2013.01); *A61B 17/7047* (2013.01); *A61B 17/8863* (2013.01); *A61B 19/0271* (2013.01); *A61B 19/50* (2013.01); *A61F 2/4611* (2013.01); *G06F 17/50* (2013.01); *G09B 23/30* (2013.01); *A61B 17/1671* (2013.01); *A61B 2017/568* (2013.01); *A61B 2019/0278* (2013.01); *A61B 2019/508* (2013.01); *A61F 2/30965* (2013.01); *A61F 2/4405* (2013.01); *A61F 2002/3095* (2013.01); *A61F 2002/30952* (2013.01); *A61F 2002/4687* (2013.01); *A61F 2310/00017* (2013.01); *A61F 2310/00023* (2013.01); *A61F 2310/00029* (2013.01); *A61F 2310/00047* (2013.01); *A61F 2310/00059* (2013.01)

(56) References Cited

U.S. PATENT DOCUMENTS

| | | |
|---|---|---|
| D359,557 S | 6/1995 | Hayes |
| D403,066 S | 12/1998 | DeFonzo |
| D412,032 S | 7/1999 | Mikula-Curtis et al. |
| D420,132 S | 2/2000 | Bucholz et al. |
| D428,989 S | 8/2000 | Segermark et al. |
| 6,711,432 B1 | 3/2004 | Krause et al. |
| 6,755,839 B2 | 6/2004 | Van Hoeck et al. |
| D532,515 S | 11/2006 | Buttler et al. |
| D533,664 S | 12/2006 | Buttler et al. |
| 7,235,076 B2 | 6/2007 | Pacheco |
| 7,491,180 B2 | 2/2009 | Pacheco |
| 7,623,902 B2 | 11/2009 | Pacheco |
| D606,195 S | 12/2009 | Eisen et al. |
| 7,658,610 B2 | 2/2010 | Knopp |
| D618,796 S | 6/2010 | Cantu et al. |
| 7,844,356 B2 | 11/2010 | Matov et al. |
| 7,957,824 B2 | 6/2011 | Boronvinskih et al. |
| 8,159,753 B2 | 4/2012 | Ojeda Castaneda et al. |
| 8,167,884 B2 | 5/2012 | Pacheco |
| 8,206,396 B2 | 6/2012 | Trabish |
| 8,214,014 B2 | 7/2012 | Pacheco |
| 8,257,083 B2 | 9/2012 | Berckmans et al. |
| D669,176 S | 10/2012 | Frey |
| 8,277,461 B2 | 10/2012 | Pacheco |
| D672,038 S | 12/2012 | Frey |
| 8,419,740 B2 | 4/2013 | Aram et al. |
| D705,929 S | 5/2014 | Frey |
| 8,758,357 B2 | 6/2014 | Frey |
| 2004/0097925 A1 | 5/2004 | Boehm et al. |
| 2005/0148843 A1 | 7/2005 | Roose |
| 2006/0084986 A1 | 4/2006 | Grinberg et al. |
| 2006/0095044 A1 | 5/2006 | Grady, Jr. et al. |
| 2006/0149375 A1 | 7/2006 | Yuan et al. |
| 2006/0241385 A1 | 10/2006 | Dietz |
| 2007/0288030 A1 | 12/2007 | Metzger et al. |
| 2008/0114370 A1 | 5/2008 | Schoenefeld |
| 2008/0161815 A1 | 7/2008 | Schoenefeld et al. |
| 2008/0183214 A1 | 7/2008 | Copp et al. |
| 2008/0257363 A1 | 10/2008 | Schoenefeld et al. |
| 2008/0275452 A1 | 11/2008 | Lang et al. |
| 2008/0312659 A1 | 12/2008 | Metzger et al. |
| 2008/0319491 A1 | 12/2008 | Schoenefeld |
| 2009/0087276 A1 | 4/2009 | Rose |
| 2009/0088674 A1 | 4/2009 | Caillouette et al. |
| 2009/0088761 A1 | 4/2009 | Roose et al. |
| 2009/0088763 A1 | 4/2009 | Aram et al. |
| 2009/0093816 A1 | 4/2009 | Roose et al. |
| 2009/0099567 A1 | 4/2009 | Zajac |
| 2009/0110498 A1 | 4/2009 | Park |
| 2009/0138020 A1 | 5/2009 | Park et al. |
| 2009/0187194 A1 | 7/2009 | Hamada |
| 2009/0198277 A1 | 8/2009 | Gordon et al. |
| 2009/0254093 A1 | 10/2009 | White et al. |
| 2009/0270868 A1 | 10/2009 | Park et al. |
| 2010/0016984 A1 | 1/2010 | Trabish |
| 2010/0049195 A1 | 2/2010 | Park et al. |
| 2010/0082035 A1 | 4/2010 | Keefer |
| 2010/0087829 A1 | 4/2010 | Metzger et al. |
| 2010/0100193 A1 | 4/2010 | White |
| 2010/0152782 A1 | 6/2010 | Stone et al. |
| 2010/0191244 A1 | 7/2010 | White et al. |
| 2010/0217270 A1 | 8/2010 | Polinski et al. |
| 2010/0217336 A1 | 8/2010 | Crawford et al. |
| 2010/0305700 A1 | 12/2010 | Ben-Arye et al. |
| 2010/0324692 A1 | 12/2010 | Uthgenannt et al. |
| 2011/0015636 A1 | 1/2011 | Katrana et al. |
| 2011/0015639 A1 | 1/2011 | Metzger et al. |
| 2011/0046735 A1 | 2/2011 | Metzger et al. |
| 2011/0054478 A1 | 3/2011 | Vanasse et al. |
| 2011/0071533 A1 | 3/2011 | Metzger et al. |
| 2011/0093023 A1 | 4/2011 | Lee et al. |
| 2011/0093086 A1 | 4/2011 | Witt et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0213376 A1 | 9/2011 | Maxson et al. |
| 2011/0218545 A1 | 9/2011 | Catanzarite et al. |
| 2011/0224674 A1 | 9/2011 | White et al. |
| 2011/0288433 A1 | 11/2011 | Kelleher et al. |
| 2012/0041445 A1 | 2/2012 | Roose et al. |
| 2012/0130434 A1 | 5/2012 | Stemniski |
| 2012/0179259 A1 | 7/2012 | McDonough et al. |
| 2012/0215315 A1 | 8/2012 | Hochschuler et al. |
| 2013/0218163 A1 | 8/2013 | Frey |

FOREIGN PATENT DOCUMENTS

| | | |
|---|---|---|
| CN | 101390773 | 11/2010 |
| CN | 101953713 | 1/2011 |
| EP | 2168507 | 3/2010 |
| WO | WO 2007/145937 | 12/2007 |
| WO | WO 2008/027549 | 3/2008 |
| WO | WO 2009/129063 | 10/2009 |
| WO | WO 2010/033431 | 3/2010 |
| WO | WO 2010/148103 | 12/2010 |
| WO | WO 2011/041398 | 4/2011 |
| WO | WO 2011/080260 | 7/2011 |
| WO | WO 2011/106711 | 9/2011 |
| WO | WO 2011/109260 | 9/2011 |

OTHER PUBLICATIONS

Notice of Allowance for U.S. Appl. No. 13/841,069, mailed Sep. 18, 2014 7 pages.

Brussel et al. "Medical Image-Based Design of an Individualized Surgical Guide for Pedicle Screw Insertion." 18th Annual International Conference of the IEEE Engineering in Medicine and Biology Society, Amsterdam 1996, pp. 225-226.

Partial Search Report for European Patent Application No. 11804191.2, dated Jan. 20, 2015 6 pages.

International Preliminary Report on Patentability for International (PCT) Patent Application No. PCT/US2013/036535, mailed Oct. 30, 2014 7 pages.

(56) References Cited

OTHER PUBLICATIONS

International Search Report and Written Opinion for International (PCT) Patent Application No. PCT/US2014/041379, mailed Oct. 28, 2014 7 pages.
U.S. Appl. No. 29/476,699, filed Dec. 16, 2013, Frey et al.
U.S. Appl. No. 29/476,705, filed Dec. 16, 2013, Frey et al.
U.S. Appl. No. 29/476,709, filed Dec. 16, 2013, Frey et al.
U.S. Appl. No. 29/496,231, filed Jul. 10, 2014, Frey et al.
Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pp. 184-191. (Abstract Only).
Lu et al. "A Novel Patient-Specific Navigational Template for Cervical Pedicle Screw Placement," Spine, Dec. 15, 2009, vol. 34, No. 26, pp. E959-E966 (Abstract Only).
Owen et al. "Rapid prototype patient-specific drill template for cervical pedicle screw placement." Computer Aided Surgery, Sep. 2007, vol. 12, No. 5, pp. 303-308 (Abstract Only).
Ryken et al. "Image-based drill templates for cervical pedicle screw placement Laboratory investigation," Journal of Neurosurgery, Jan. 2009, vol. 10, No. 1 (Abstract Only).
Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).
International Search Report and Written Opinion for International (PCT) Patent Application No. PCT/US11/42412 mailed Nov. 8, 2011, 8 pages.
International Preliminary Report on Patentability for International (PCT) Patent Application No. PCT/US11/42412 mailed Jan. 17, 2013, 7 pages.
International Search Report and Written Opinion for International (PCT) Patent Application No. PCT/US2013/036535, mailed Jun. 26, 2013 8 pages.
Official Action for Australian Patent Application No. 2011276468 dated Apr. 10, 2013, 3 pages.
Official Action for U.S. Appl. No. 13/172,683, mailed Sep. 10, 2013 7 pages.
Official Action for U.S. Appl. No. 13/172,683, mailed Feb. 24, 2014, 10 pages.
Notice of Allowance for U.S. Appl. No. 13/172,683 mailed Apr. 23, 2014, 7 pages.
Notice of Allowance for U.S. Appl. No. 29/409,734, mailed May 11, 2012 8 pages.
Notice of Allowance for U.S. Appl. No. 29/427,918, mailed Oct. 15, 2012 9 pages.
Notice of Allowance for U.S. Appl. No. 29/432,668 mailed Nov. 27, 2013, 11 pages.
Official Action for U.S. Appl. No. 13/841,069 mailed Jul. 8, 2014, 6 pages.
Official Action for U.S. Appl. No. 13/841,069, mailed Jul. 31, 2014 9 pages.

Insert Diameter for 4.5 mm Tap

Insert Diameter for 1/8" Drill Bit

FIG. 33A
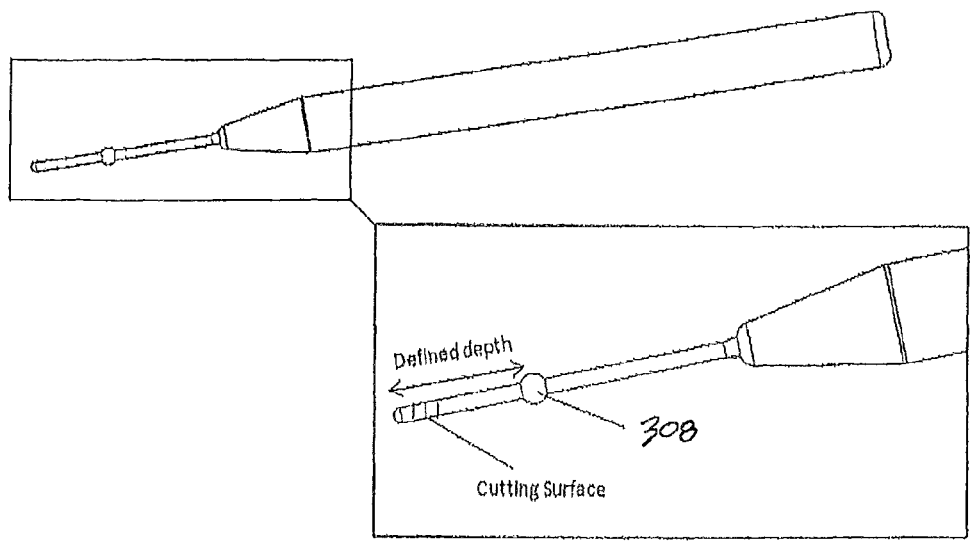
FIG. 33B
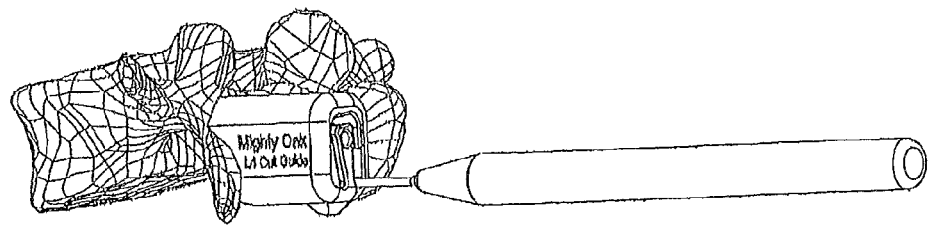
FIG. 33C

FIGURE 40 A-D

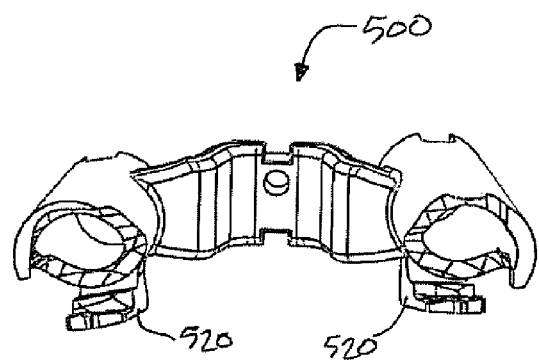
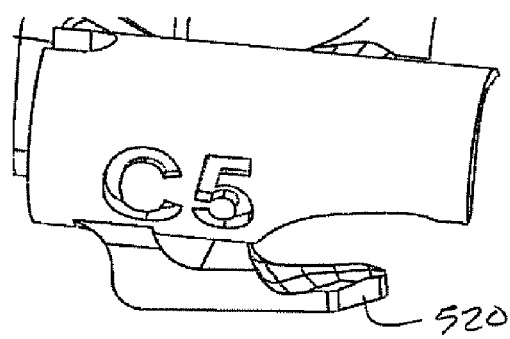
FIG. 51A   FIG. 51B
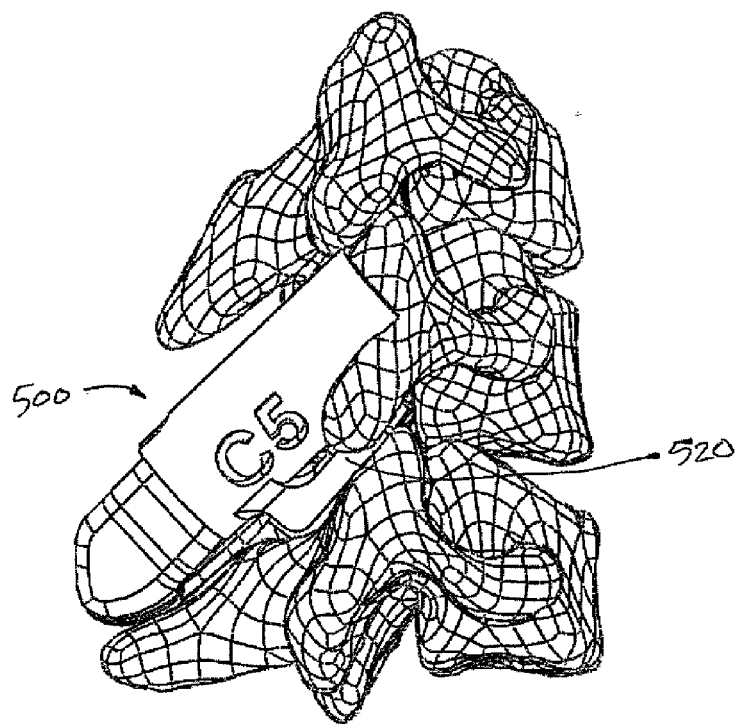
FIG. 51C

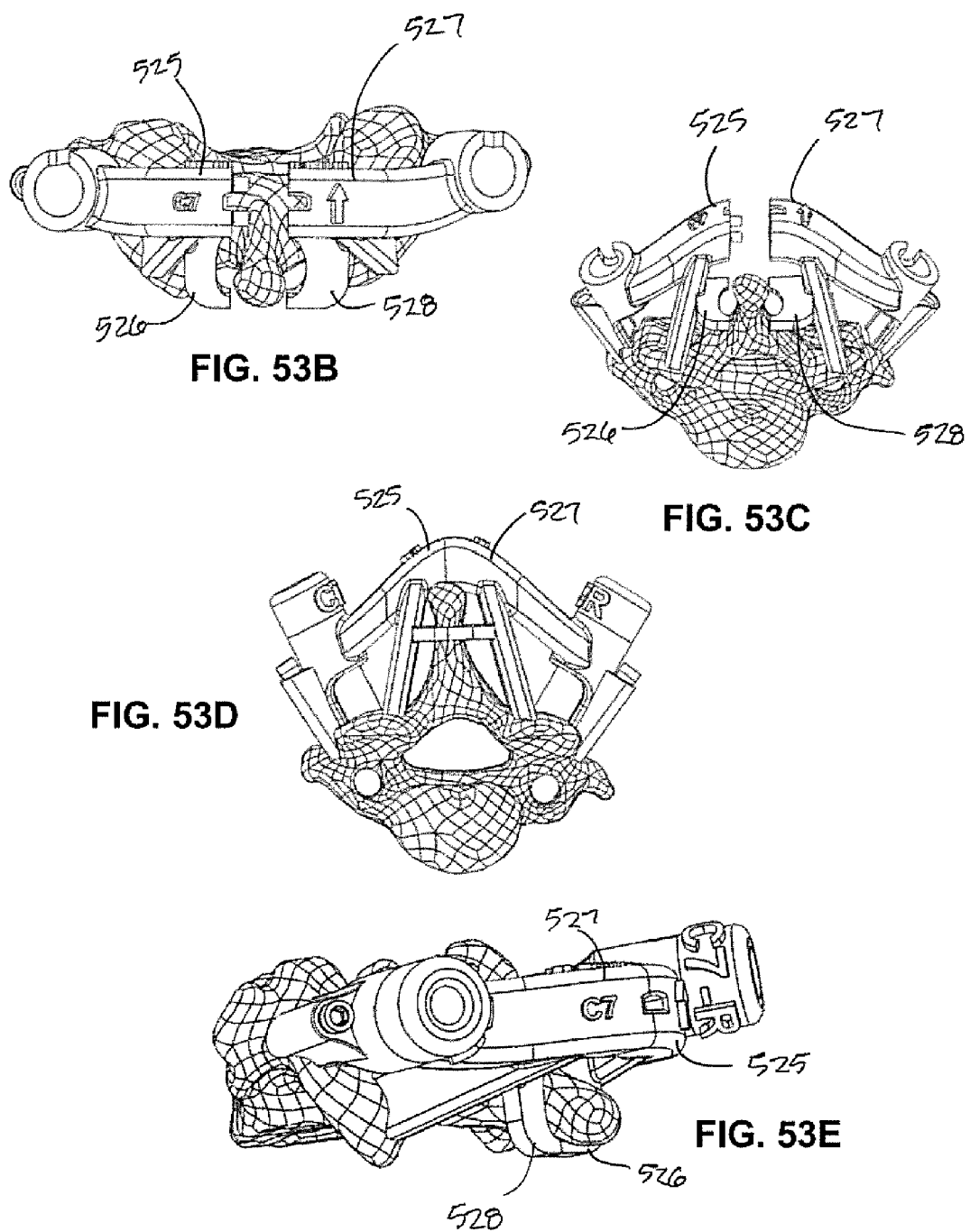

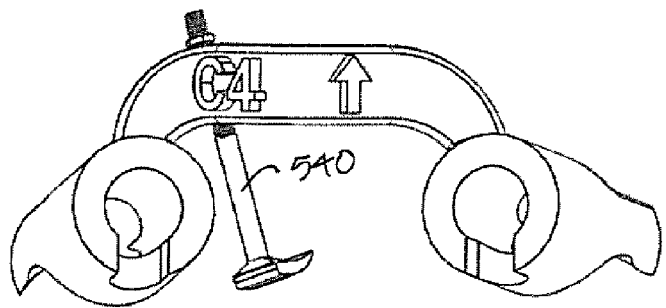
FIG. 55A
FIG. 55B
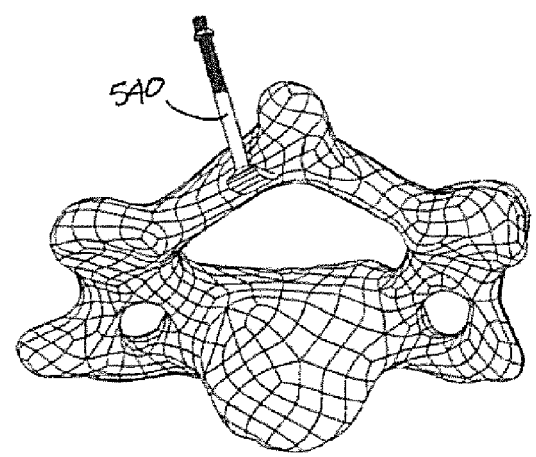
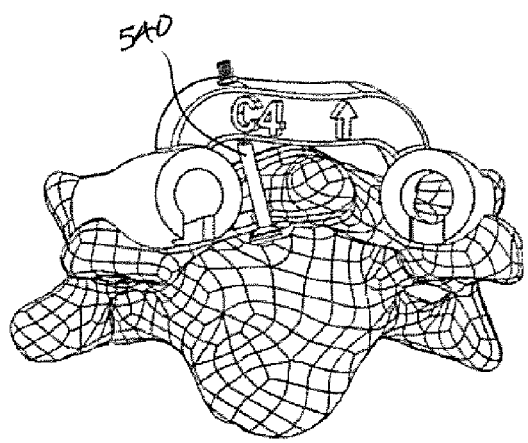
FIG. 55C

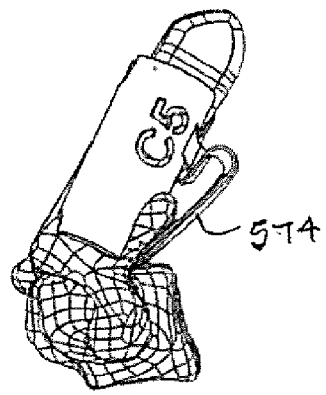
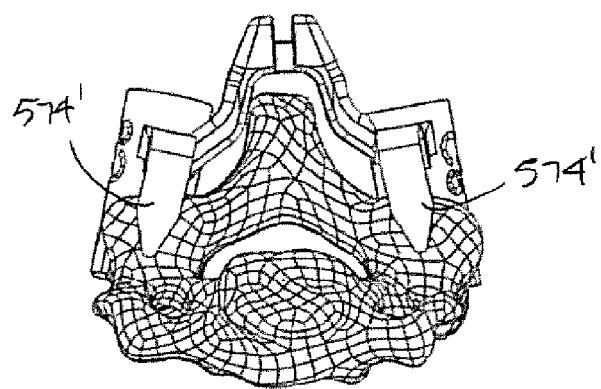
FIG. 60A  FIG. 60B
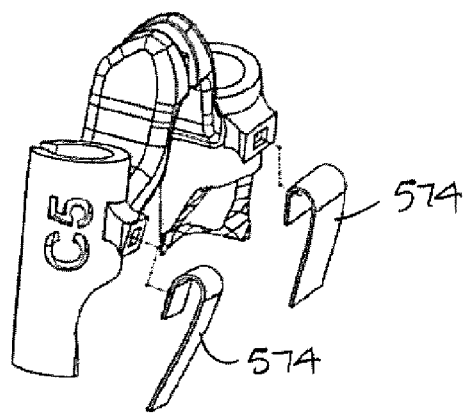
FIG. 60C

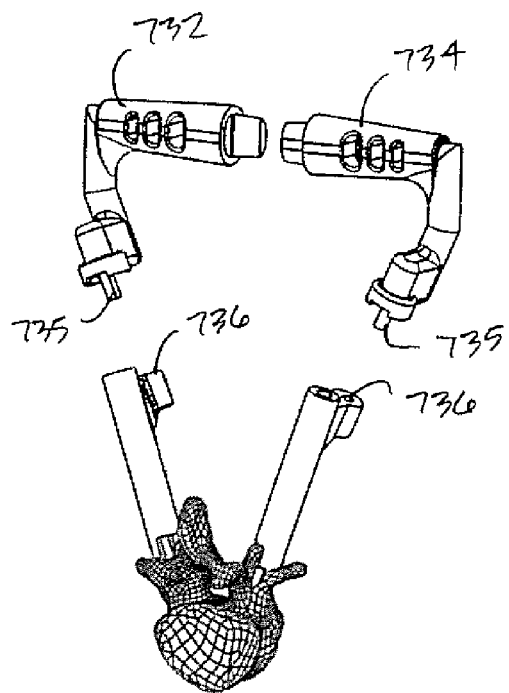
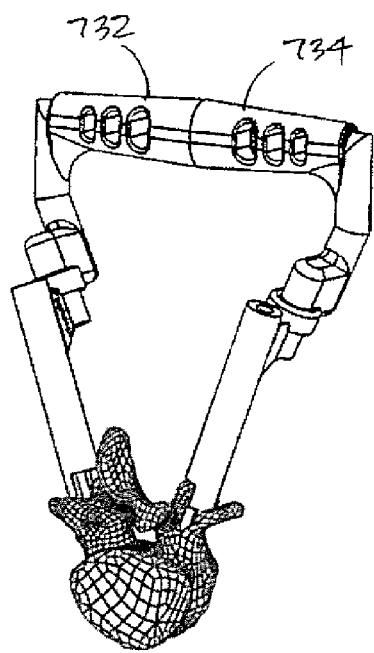
FIG. 76A      FIG. 76B
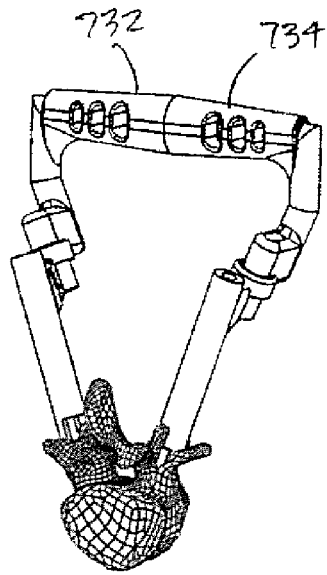
FIG. 76C

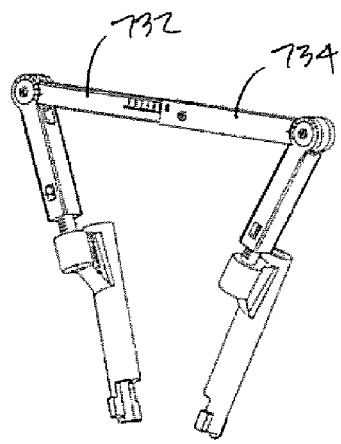
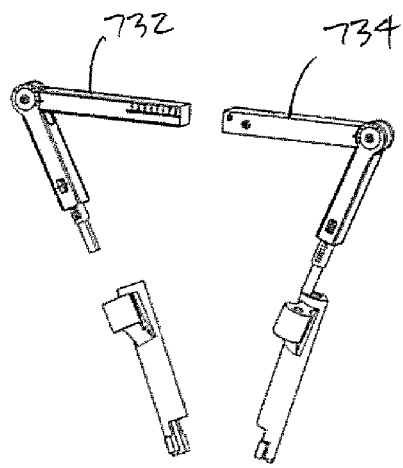
FIG. 77A   FIG. 77B
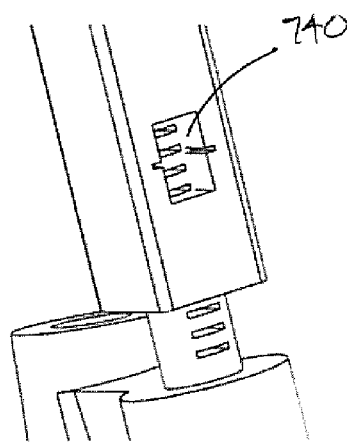
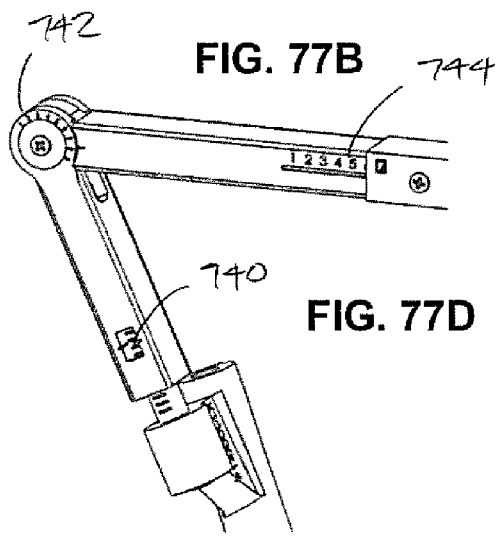
FIG. 77C   FIG. 77D
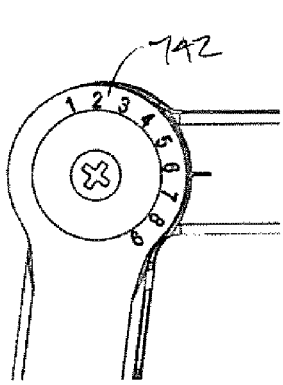
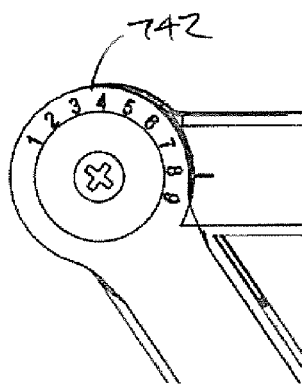
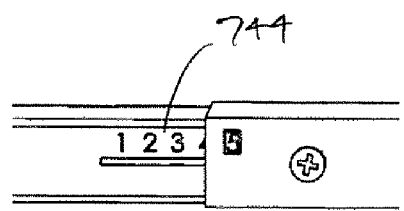
FIG. 77E   FIG. 77F   FIG. 77G

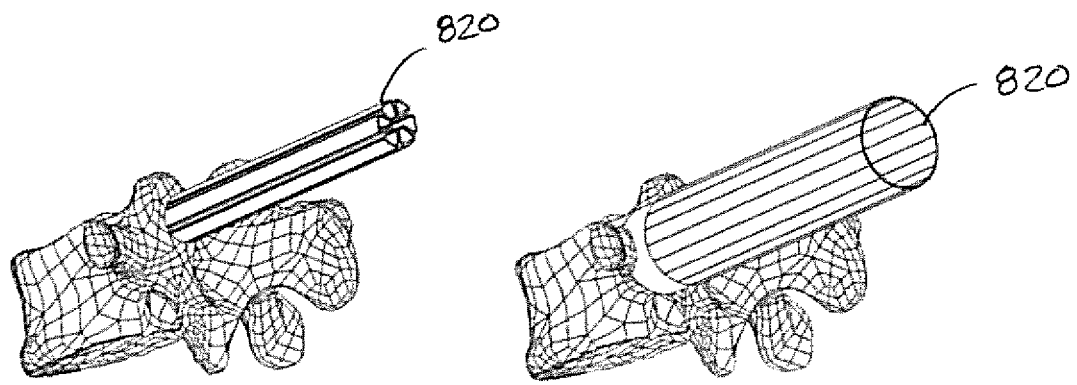
FIG. 84A       FIG. 84B
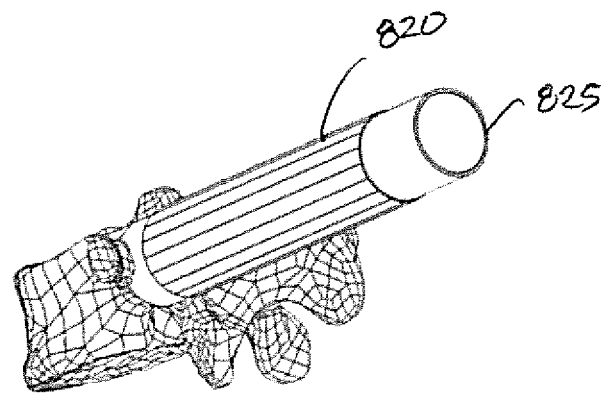
FIG. 84C

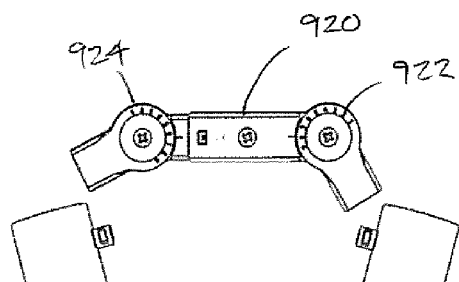
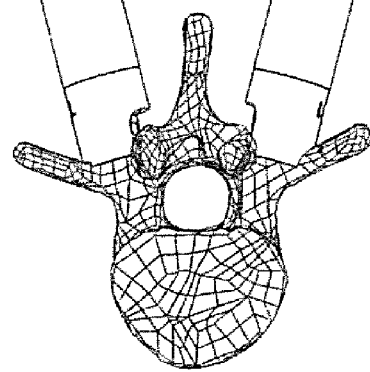
FIG. 91A
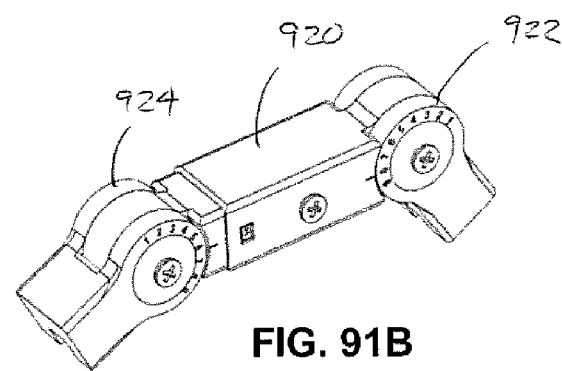
FIG. 91B
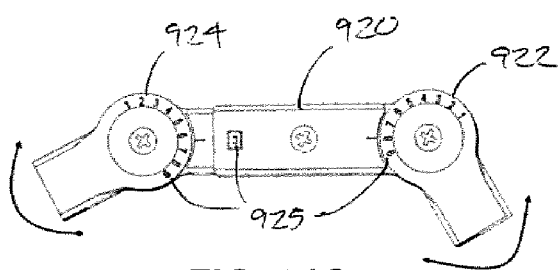
FIG. 91C
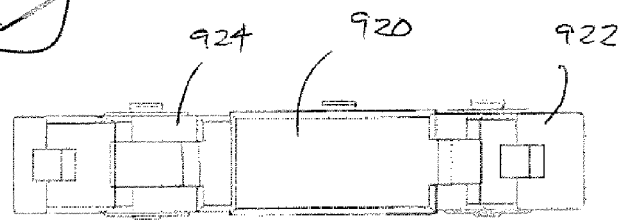
FIG. 91D

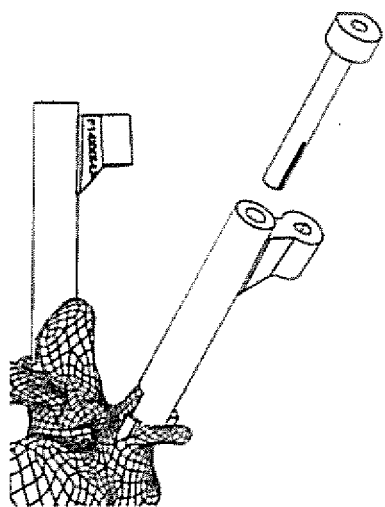
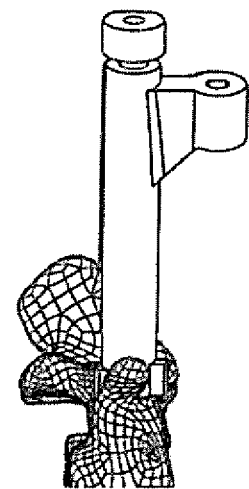
FIG. 98A    FIG. 98B
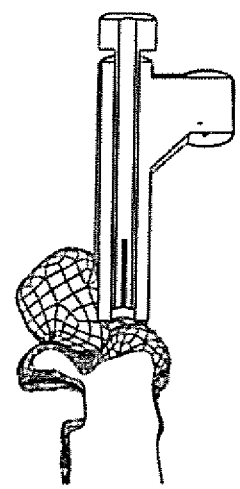
FIG. 98C

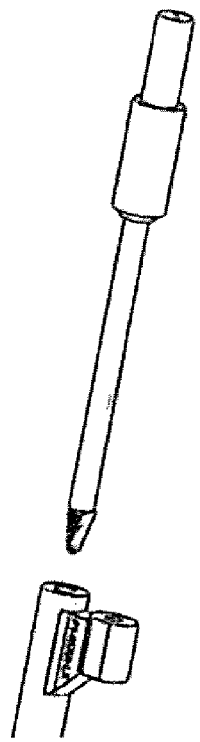
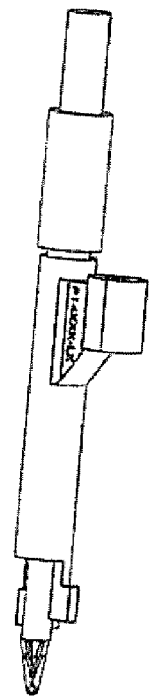
FIG. 100A
FIG. 100B
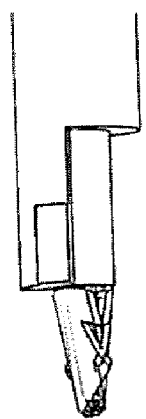
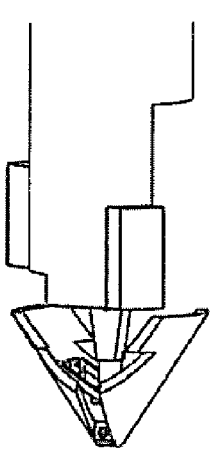
FIG. 100C
FIG. 100D

PATIENT-MATCHED APPARATUS AND METHODS FOR PERFORMING SURGICAL PROCEDURES

CROSS-REFERENCE TO RELATED APPLICATIONS

This application is a continuation-in-part of U.S. patent application Ser. No. 13/841,069, filed Mar. 15, 2013. This application also claims the priority to U.S. Provisional Patent Application Nos. 61/832,583 filed Jun. 7, 2013, 61/845,463 filed Jul. 12, 2013 and 61/877,837 filed Sep. 13, 2013. These applications are all incorporated by reference herein in their entireties.

FIELD OF THE INVENTION

The present disclosure relates to the field of medical devices and is generally directed toward apparatus configurable for use with a specific patient in a surgical setting based on the patient's unique anatomical features, and methods of manufacturing and using the same.

BACKGROUND OF THE INVENTION

Given the complexities of surgical procedures and the various tools, instruments, implants and other devices used in the procedures, as well as the varying anatomical differentiation between patients who receive those tools, instruments, implants and devices, it is often challenging to create a surgery plan that accounts for the unique and sometimes irregular anatomical features of a particular patient. For example, the implantation of pedicle screws in a vertebral body (as an adjunct or stand-alone stabilization mechanism) is well accepted amongst surgeons who treat various spine pathologies, and although the performance of various pedicle screw constructs have become predictable, there are still multiple challenges with the placement and insertion of the pedicle screws or other bone anchors. The challenges occur when a surgeon is unable to reference boney landmarks due to previous surgery or when the patient's anatomy is irregular in shape.

Surgeons now have the ability to readily convert magnetic resonance imaging (MRI) data or computed tomography (CT) data into a data set readable by computer-aided design (CAD) program and/or finite element modeling (FEM) program, which then may be used to create, for example, a custom implant based on the dynamic nature of the anatomical structures the custom implant is designed to associate with. This data, while currently used by surgeons in surgery planning, is largely unused for creating a customized set of instruments or other surgical devices that are designed to complement the patient's unique anatomy.

The prior art fails to teach a system for creating a suite of surgical apparatus based on the data set derived from the MRI or CT scan. For example, the use of the patient-specific data set for a vertebral body may allow a surgeon to accommodate for subtle variations in the position and orientation of a plate or other bone anchor to avoid particular boney anatomy or irregularities in the positioning and alignment of the adjoining vertebral bodies. As another example, the use of these data sets may also assist a surgeon in selecting a desired trajectory for an implantable device so as to avoid, for example, crossing the pedicle wall and violating the spinal canal during an actual procedure. The use of the data sets permit the surgeon to avoid these types of mistakes by creating customized tools and instruments, which may comprise orientation, end-stops or other safety related features to avoid over-torque and over-insertion of any implantable devices. The data sets also permit the surgeon to create a patient-contacting surface that is oriented to match one or more of the anatomical features represented by the data set, and thereby quickly and efficiently locate and place the patient-contacting surface(s) in the appropriate location and orientation.

It would therefore be advantageous to provide apparatus suitable for use with a surgical procedure that is adapted and/or configured and/or capable of conforming to a plurality of anatomical features of a particular patient and/or to one or more additional apparatus to assist the surgeon in completing the surgical procedure(s) safely and efficiently, and that otherwise significantly reduces, if not eliminates, the problems and risks noted above. Other advantages over the prior art will become known upon review of the Summary and Detailed Description of the Invention and the appended claims.

SUMMARY OF THE INVENTION

According to one aspect of the present disclosure, a novel system and method is described for developing customized apparatus for use in one or more surgical procedures. The system and method according to this embodiment uses a patient's unique morphology, which may be derived from capturing MRI data or CT or other data to derive one or more "Patient Matched" apparatus, which comprises complementary surfaces based on a plurality of data points from the MRI or CT data. Each "Patient Matched" apparatus is matched and oriented around the patient's own anatomy, the desired insertional trajectories (which may be verified in a pre-operative setting using 3D CAD software, such as the software disclosed in WO 2008027549, which is incorporated by reference herein in its entirety), and according to one embodiment described herein, other apparatus used during the surgical procedure.

By way of providing additional background, context, and to further satisfy the written description requirements of 35 U.S.C. §112, the following are incorporated by reference in their entireties for the express purpose of explaining the nature of minimal access, less invasive, or minimally invasive surgery ("MIS") procedures and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. patent application Ser. No. 2008/0255564 to Michelson.

Various surgical procedures may be performed through introduction of rods or plates, screws or other devices into adjacent boney anatomy to join various portions of, for example, a vertebra to a corresponding portion on an adjacent vertebra. MIS procedures are often performed in the sacroiliac, lumbar, thoracic, or cervical spine regions of a patient. MIS procedures performed in this area are often designed to stop and/or eliminate all motion in the spinal segment by destruction of some or all of the joints in that segment and further utilizing bone graft material and/or rigid implantable fixation devices for securing the adjacent vertebrae. By eliminating movement, back pain and further degenerative disc disease may be reduced or avoided. Fusion requires tools for accessing the vertebrae, such as surgical cannulae for MIS procedures, and other tools for implanting the desired implant, bioactive material, etc. Such procedures often require introduction of additional tools to prepare a site for implantation. These tools may include drills, drill guides, debridement tools, irrigation devices, vises, clamps, cannula, and other insertion/retraction tools.

Spinal and other surgeries may be performed by a number of different MIS procedures, as opposed to conventional surgical procedures and methods, which typically require cutting of muscles, removal of bone, and retraction of other natural elements. During a MIS procedure, a less destructive approach to the patient anatomy is carried out by using retractor tubes or portals, which take advantage of anatomy and current technology to limit the damage to intervening structures.

In a typical MIS procedure on the spine, skeletal landmarks are established fluoroscopically and a small incision is made over the landmark(s). According to various methods known in the prior art, a series of dilators are applied until one or more cannula is placed over the anatomic structure. In some procedures, a microscope is then placed over the operative site to provide illumination and magnification with a three dimensional view of the anatomical site to ensure that the surgeon is able to accurately locate the desired patient anatomy and properly position and orient any tool, instrument or other surgical device used during the MIS procedure. The microscope, however. is an expensive and unwieldy device requiring uncomfortable gyrations of the surgeon's back and neck in order to gain the necessary view, and is also a nuisance to drape (a large, sterile plastic bag has to be placed over the eight foot tall structure). The use of adequate illumination is also difficult to direct due to the size of the microscope.

A significant danger of performing MIS operations, and in particular accessing an intervertebral space during a MIS surgery on the spine, is that of inadvertently contacting or damaging the para-spinal nerves, including the exiting nerve roots, traversing nerves and the nerves of the cauda equina. The exact location of these para-spinal nerves cannot be precisely determined prior to the commencement of surgery, and therefore are dependent on a surgeon's ability to visually locate the same after the initial incision is made. Moreover, intervertebral spaces in the spine have other sensitive nerves disposed at locations which are not entirely predictable prior to insertion of the surgical tool into the intervertebral area. Accordingly, the danger of pinching or damaging spinal nerves when accessing an intervertebral space has proven to be quite limiting to the methods and devices used during minimally invasive spinal surgery. In addition, as cannula are received through the patient's back, such as when performing minimally invasive spinal surgery, minor blood vessels are ruptured, thereby blocking the surgeon's vision inside the intervertebral region after the cannula has been inserted. Other anatomical features at a particular patient may also destruct the surgeon's view or make it difficult to provide illumination within the cannula. Therefore, one particular shortcoming that is addressed by the present disclosure is to provide devices which are patient-matched to facilitate proper location and orientation without use of microscopes or other equipment and that otherwise eliminate the problems associated with prior art MIS procedures.

The customized and integrated matching aspects of this presently disclosed system provides an advantage over the prior art, in particular by providing a plurality of interlocking and/or matching points for each apparatus, which in turn reduces the likelihood of misalignment, misplacement and subsequent mistake during the surgical procedure(s).

Accordingly, one aspect of the present disclosure is to provide a method for preparing a customized surgical device or instrument, which in a preferred embodiment comprises the following steps:

obtaining data associated with a patient's anatomy;

converting the data obtained to a 3-dimensional data set(s);

determining at least one trajectory or path for facilitating a surgical procedure to be performed on the patient;

determining at least one surface associated with the patient's anatomy;

generating a 3-dimensional representation of the customized surgical device or instrument, which incorporates the at least one trajectory of path and a matching surface to the at least one surface associated with the patient's anatomy; and fabricating the customized surgical device or instrument using the 3-dimensional representation.

According to another aspect of the present disclosure, a system and method for facilitating a surgical procedure(s) comprises the following steps:

Obtaining data associated with the patient's anatomy by way of a MRI or CT scan;

Converting the MRI or CT scan data to a 3-Dimensional data set(s)

Determining one or more axes or planes of orientation of a device to be constructed for use in facilitating the surgical procedure(s) to be performed on the patient;

Modeling the device for use in facilitating the surgical procedure(s) using the determined axes and accounting for any other constraints derived from the converted data set(s);

Generating a prototype of the modeled device by, for example, use of rapid prototyping machinery; and Preparing the prototype for use during the surgical procedure(s).

According to this aspect described above, the method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc.

According to yet another aspect of the present disclosure, the system and method includes use of data obtained from a radiographic imaging machine, a fluoroscopy, an ultrasonic machine or a nuclear medicine scanning device.

In another aspect, the patient-matching features may be confirmed by one or more additional process, such as fluoroscopy or other processes known to those of skill in the art.

In one aspect of the present disclosure, the method comprises the use of bone density data obtained through a CT scan of the patient anatomy for use in planning the trajectory of a surgical guide and corresponding fixation device or instrument, such as a cutting/routing/drilling instrument intended to penetrate the boney anatomy. This data may be used in other manners contemplated and described herein to assist the surgeon in planning, visualizing or otherwise preparing for the surgical procedure for the patient.

In yet another alternative embodiment, the data obtained from one of the scanning devices described above may be supplemented or merged with data from a bone density scanner to fabricate a device that is designed to remain in the patient after the surgical procedure is completed. It is to be expressly understood that data from a bone density scanner is not necessary to practice the inventions described herein, but may supplement the data and assist a surgeon or other medical professional in determining the proper location, trajectory, orientation or alignment of the various apparatus described herein.

According to yet another aspect of the present disclosure, data may be supplemented or merged with data from a bone density scanner to achieve further control over the orientation of any desired axes, particularly where the surgical procedure involves insertion of one or more implantable devices.

According to yet another embodiment, the data obtained from the patient permits the apparatus to be manufactured with defined pathways through the apparatus, which are operatively associated with at least one tool, instrument, or implant, and which permit the at least one tool, instrument or implant to be inserted in the defined pathways in a consistent and reproducible manner. Examples of devices that are implanted or remain in the patient include anchoring devices such as screws, pins, clips, hooks, etc., and implantable devices such as spacers, replacement joints, replacement systems, cages, etc.

According to yet another aspect of the present disclosure, a preconfigured surgical template is disclosed, which comprises one or more guides for receiving at least one tool. According to this embodiment, the one or more guides further comprise patient-contacting surfaces formed to be substantially congruent with the anatomical features of a patient. The preconfigured surgical template is configured such that the patient-contacting surfaces are configured to contact the plurality of anatomical features in a mating engagement, to ensure proper alignment and mounting of the guide or template, and the guides of the preconfigured surgical template are oriented in a direction selected prior to manufacturing of the preconfigured surgical template to achieve desired positioning, aligning or advancing of a tool within the one or more guides.

According to yet another aspect of the present disclosure, a method for creating a template for use in a surgical operation is disclosed, comprising the steps of:

collecting data from the patient corresponding to the patient's unique anatomy;

creating a model of the template from the data collected, the model comprising a plurality of matching surfaces to the patient's unique anatomy;

providing data associated with model to fabrication machinery;

rapidly generating the template to comprise the plurality of matching surfaces and further comprising at least one additional matching surface corresponding to at least one tool or instrument used in the surgical operation; and generating a permanent device based on the template for use in the surgical operation.

In one embodiment of the present disclosure the model is a digital model. In another embodiment of the present disclosure the model is a physical model.

According to yet another aspect of the present disclosure, a system for performing a surgical procedure on a patient is disclosed, comprising:

a surgical guide;

the surgical guide comprising a plurality of surfaces determined from data scanned from the patient, the plurality of surfaces configured to match the patient's boney anatomy;

the surgical guide further comprising at least one trajectory or path determined from the patient's boney anatomy for facilitating the surgical procedure;

the surgical guide further comprising at least one sleeve, the sleeve comprised of a conductive material and having a first end and a second end;

an instrument comprising at least a first portion comprised of a conductive material and adapted to be received within the at least one sleeve by inserting the at least a first portion in the first end of the at least one sleeve and contact the conductive material of the at least one sleeve;

wherein the at least a first portion of the instrument is adapted to pass through the at least one sleeve and exit the second end of the at least one sleeve; and wherein the surgical guide may be subject to an electrical current for providing intra-operative monitoring (IOM) of the instrument during contact with the surgical guide and with the patient anatomy.

Further aspects of the present disclosure are directed to the system described above and further comprising a surgical guide which is subject to an electrical current by providing at least one electrode on the conductive material of the surgical guide and providing electrical current to the at least one electrode.

Further aspects of the present disclosure provide a method for manufacturing a surgical guide at an off-site manufacturing location, an on-site manufacturing location, a clinic, a surgery center, a surgeon's offices, a public hospital or at a private hospital.

Still further aspects of the present disclosure include a surgical guide manufactured using one of the methods described herein, wherein the guide is manufactured by a process selected from the group consisting of a rapid prototyping machine, a stereolithography (SLA) machine, a selective laser sintering (SLS) machine, a selective heat sintering (SHM) machine, a fused deposition modeling (FDM) machine, a direct metal laser sintering (DMLS) machine, a powder bed printing (PP) machine, a digital light processing (DLP) machine, an inkjet photo resin machine, and an electron beam melting (EBM) machine.

Incorporated by reference in their entireties are the following U.S. patents and patent applications directed generally to methods and apparatus related to surgical procedures, thus providing written description support for various aspects of the present disclosure. The U.S. patents and pending applications incorporated by reference are as follows: U.S. Pat. Nos. 7,957,824, 7,844,356 and 7,658,610, and U.S. Pat. Pub. Nos. 2010/0217336, 2009/0138020, 2009/0087276 and 2008/0114370.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the devices described herein, including, for example, width, length and thickness, and the size of the surgical apparatus.

Embodiments of the present disclosure present several advantages over the prior art including, for example, the speed and efficacy of the procedure, the minimally invasive aspects of the procedure, the disposability of the prototype devices, the ability to introduce customized implements or tools to the surgical site with minimal risk and damage to the surrounding tissue, lower risk of infection, more optimally placed and/or oriented guides and implantable devices, a more stable and controlled method of placing and inserting of apparatus associated with the surgical procedure further reducing the likelihood of the apparatus becoming misaligned or dislodged, and fewer and/or less expensive tools and instruments in a surgical site, among other advantages. For example, the embodiments reduce the number and need for multiple trays, instruments and different size devices used in a particular surgery, thereby reducing the cost of the equipment necessary to complete the surgery. The embodiments also reduce the cumulative radiation exposure to both the surgeon and medical professionals in the operating environment and the patient.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials rubber, latex, synthetic rubber, synthetic materials, polymers, and natural materials.

One having skill in the art will appreciate that embodiments of the present disclosure may be used in conjunction devices that employ automated or semi-automated manipulation. Embodiments of the present disclosure may be designed such that the apparatus may be formed and verified, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators. It is expressly understood for purposes of this disclosure that other types of machinery other than rapid prototyping machinery may be employed in the systems and methods described herein, for example, by computerized numerical control (CNC) machinery.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the claims set forth herein below define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

In the drawings:

FIG. 1 is a perspective view of a three-dimensional model of a unique grouping of anatomical features from which a set of data points may be derived according to one embodiment of the present disclosure;

FIG. 2 is a flow chart diagram showing the various steps of performing a method of manufacturing and using an apparatus for facilitating a surgical procedure according to one embodiment of the present disclosure;

FIG. 3 is a side elevation view of a particular apparatus for facilitating a surgical procedure according to one embodiment of the present disclosure;

FIG. 4 is rear elevation view of the apparatus shown in FIG. 3;

FIG. 5 is a top plan view of the apparatus shown in FIG. 3, relative to a unique grouping of anatomical features, and according to one embodiment of the present disclosure;

FIG. 6 is a perspective view of the apparatus and unique grouping of anatomical features shown in FIG. 5;

FIG. 7 is another perspective view of the apparatus shown in FIG. 3 demonstrating the customized patient-matching surfaces of the apparatus;

FIG. 8 is a perspective view of an apparatus according to an alternative embodiment of the present disclosure;

FIG. 9 is a perspective view of an apparatus according to yet another alternative embodiment of the present disclosure.

FIG. 10 is another perspective view of the apparatus shown in FIG. 3 along with a custom fabricated instrument for use during a particular surgical procedure;

Figure 11A:
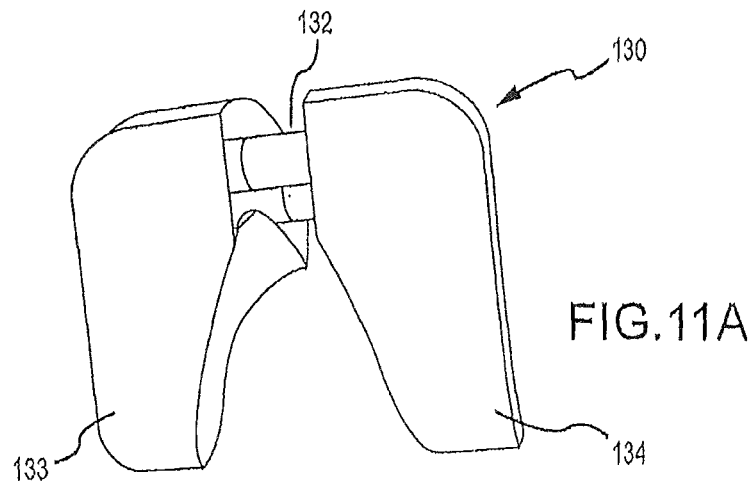
Figure 11B:
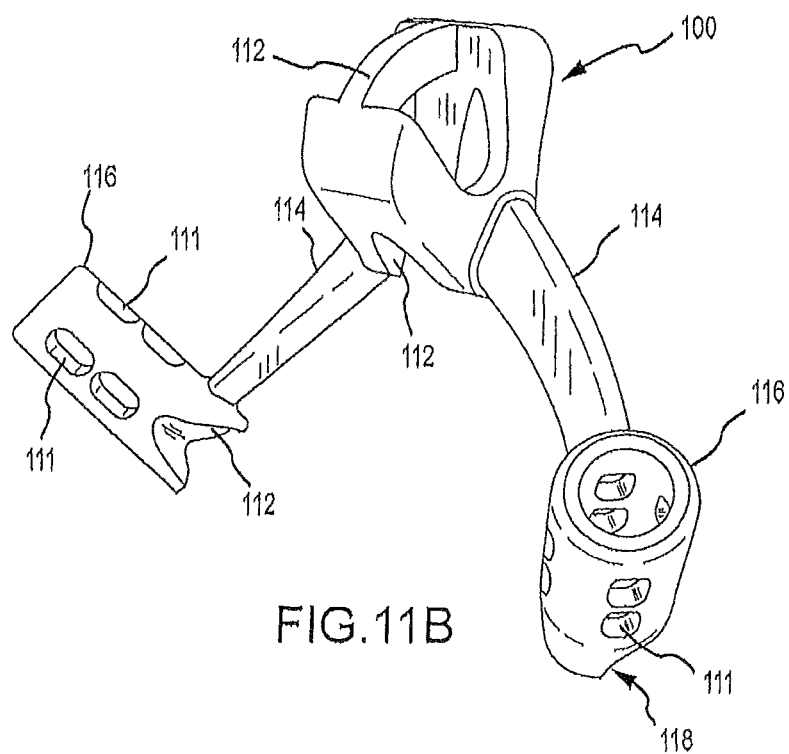
Figure 12:
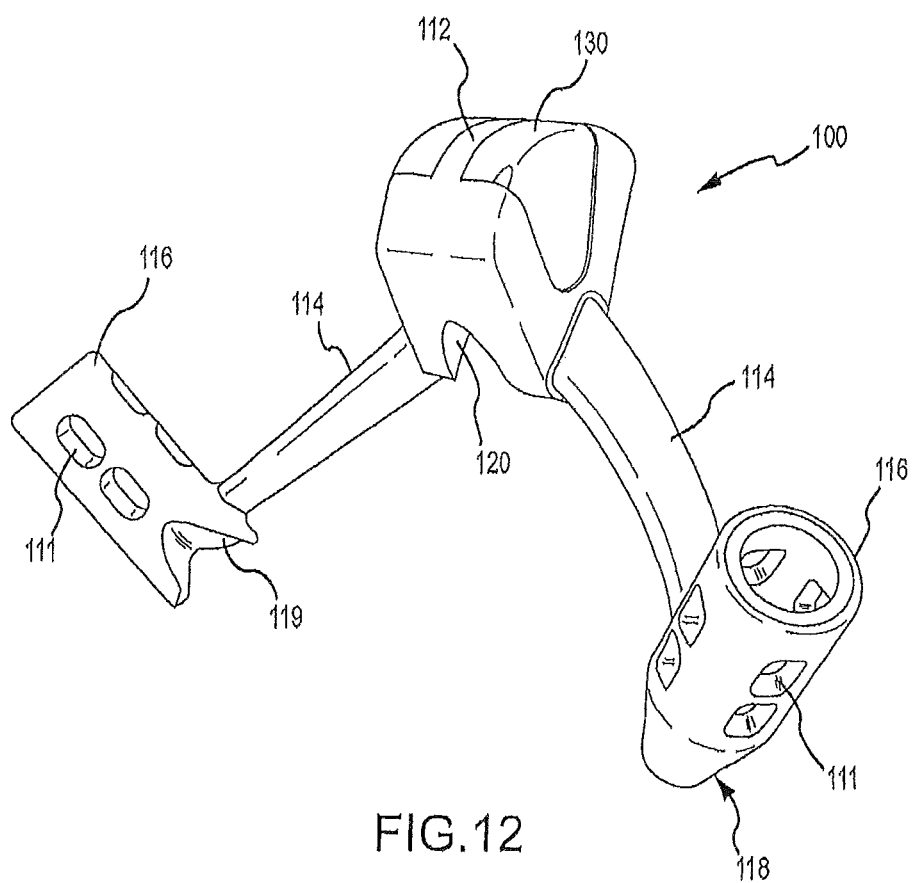
Figure 13:
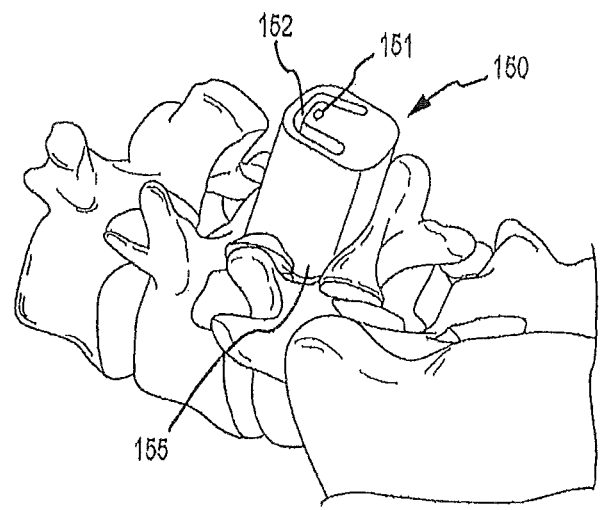
Figure 14:
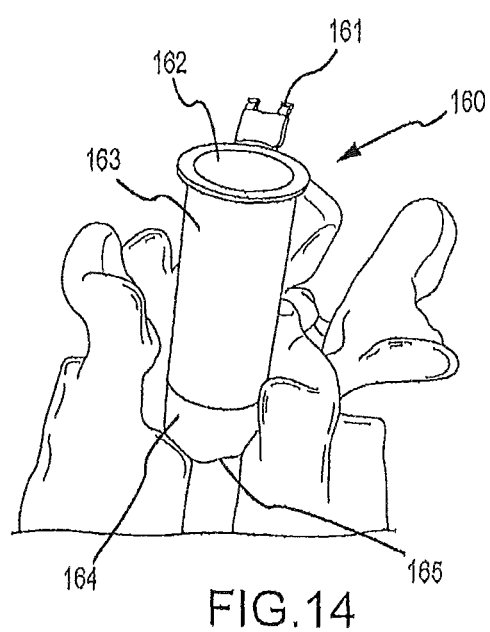
Figure 15:
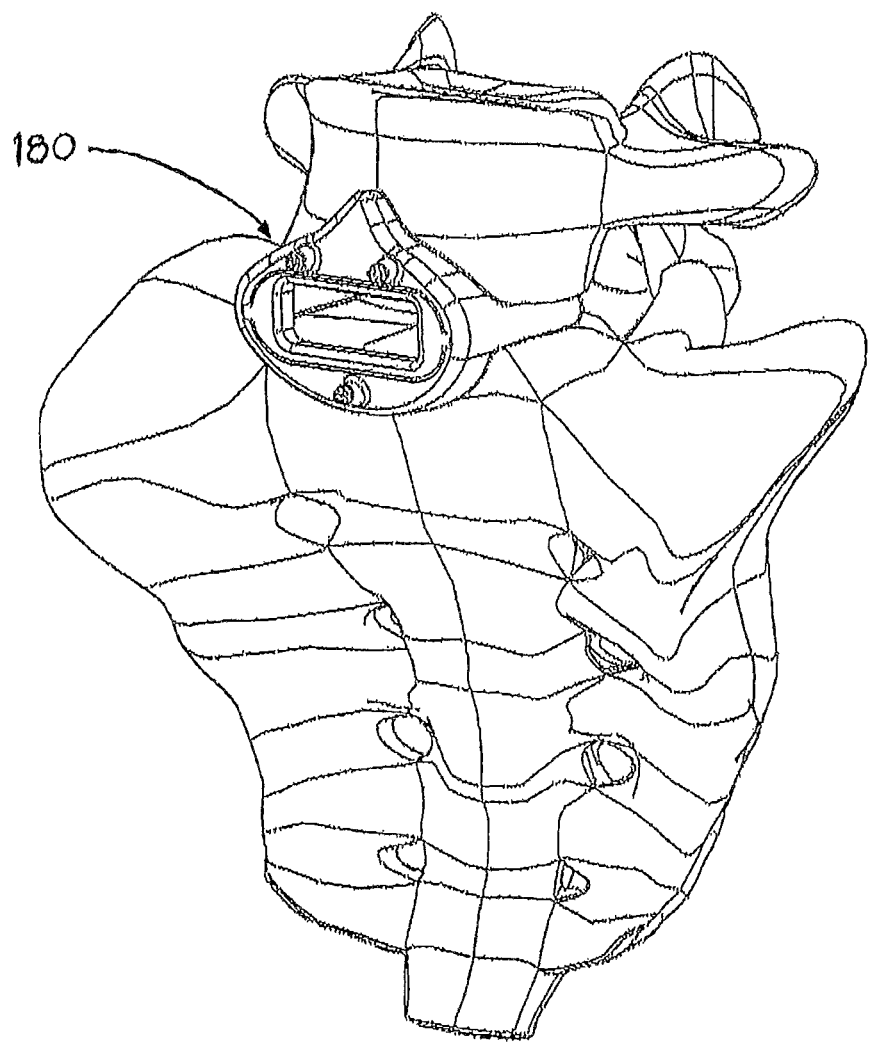
Figure 16:
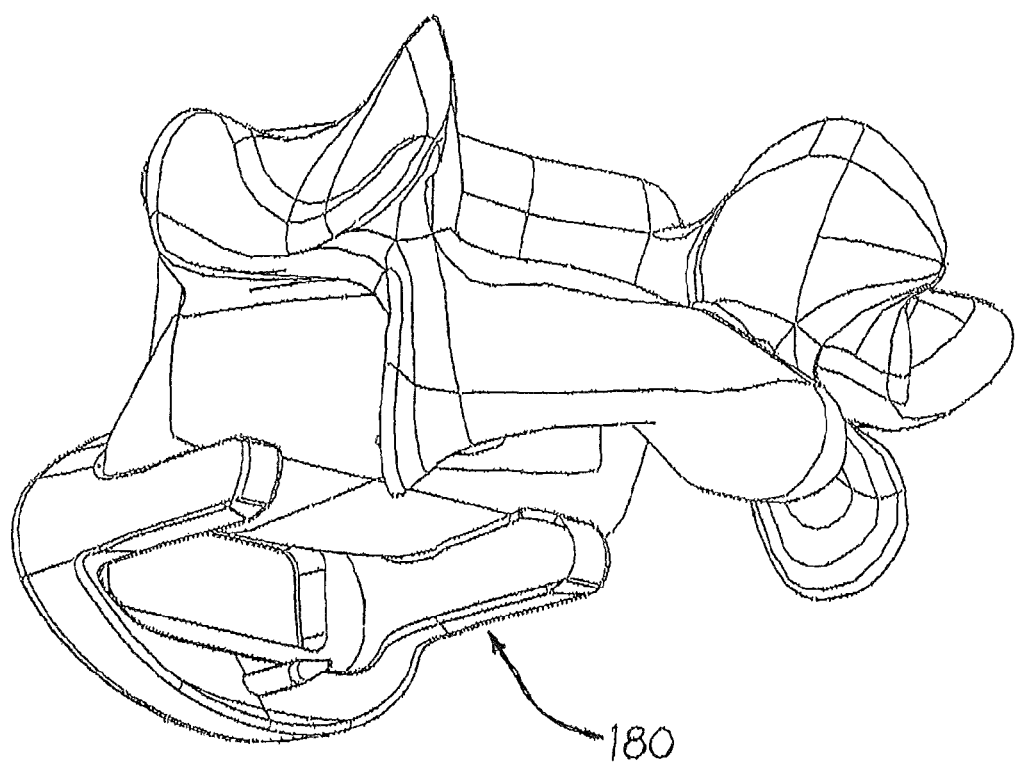
Figure 17:
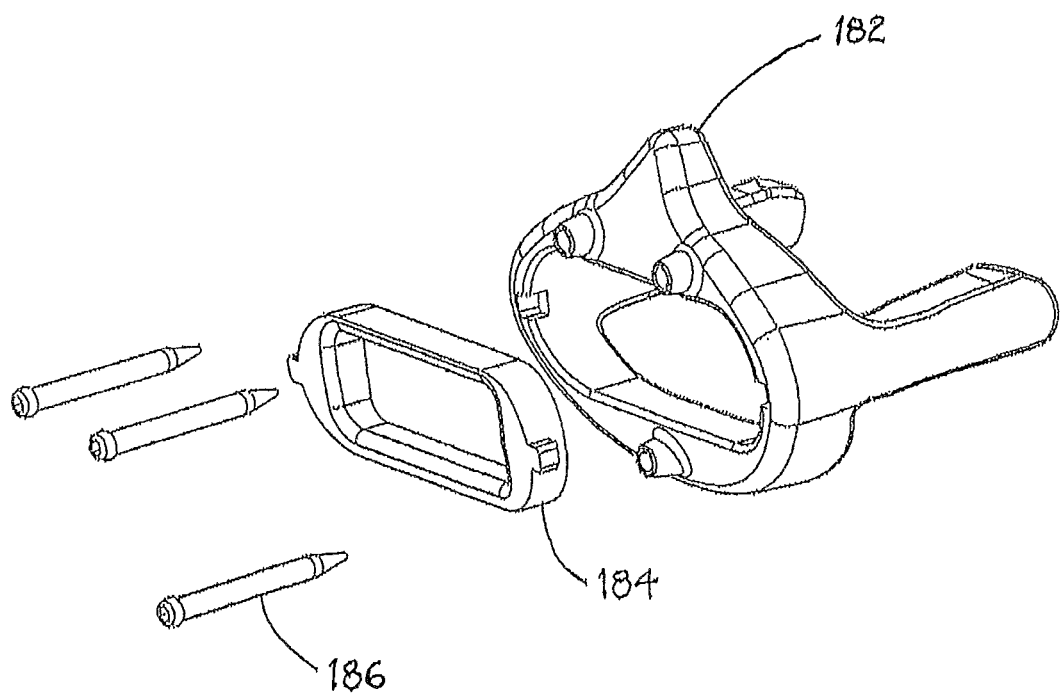

FIGS. 11A-B are perspective views of an apparatus according to another alternative embodiment of the present disclosure;

FIG. 12 is a perspective view of the apparatus shown in FIGS. 11A-B in an assembled state;

FIG. 13 is a perspective view of an apparatus according to yet another alternative embodiment of the present disclosure;

FIG. 14 is a perspective view of an apparatus according to yet another alternative embodiment of the present disclosure;

FIG. 15 is a perspective view according to yet another alternative embodiment of the present disclosure;

FIG. 16 is a different perspective view of the apparatus shown in FIG. 15;

FIG. 17 is an exploded perspective view of the apparatus shown in FIG. 15.

Figures 18, 19:
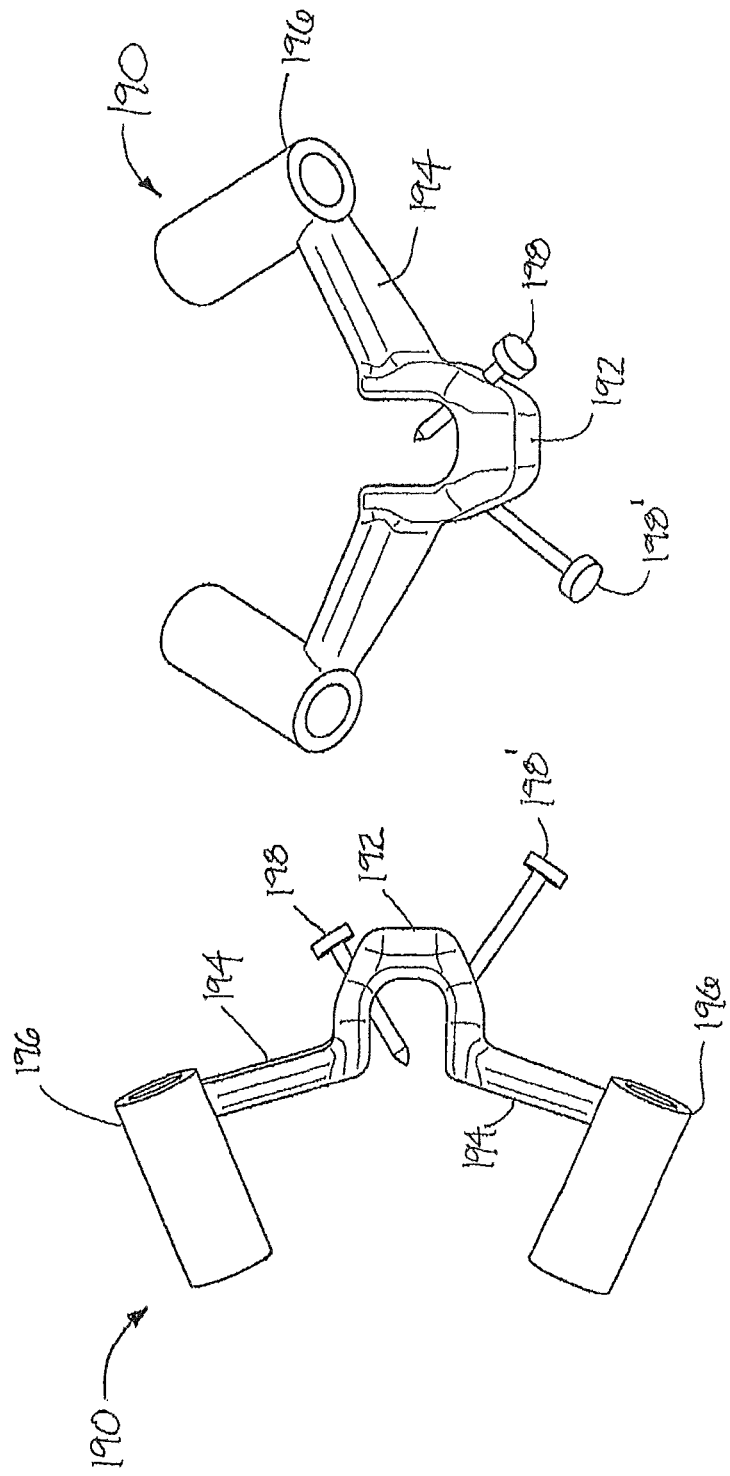
Figure 20:
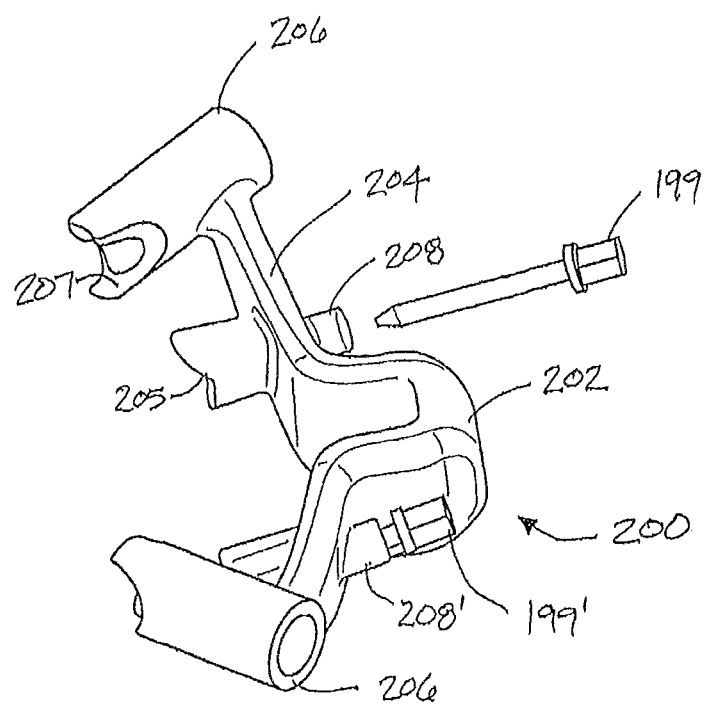
Figure 21:
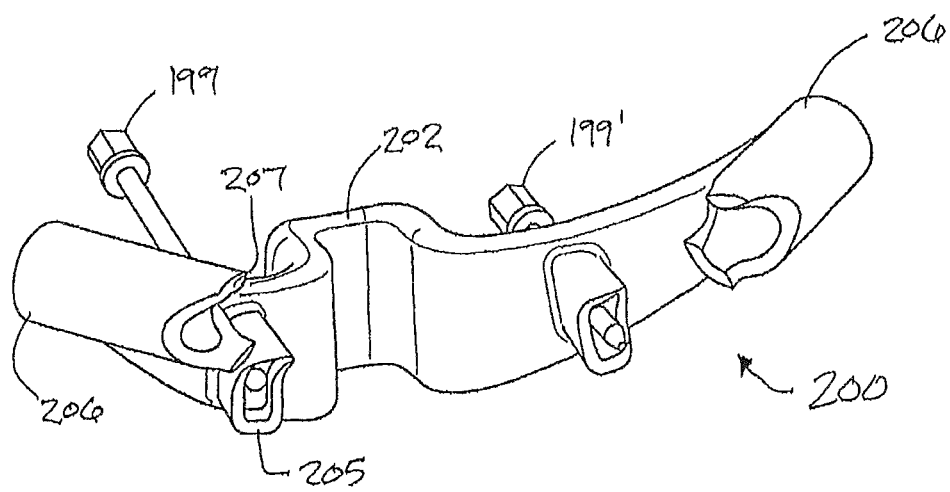
Figure 22:
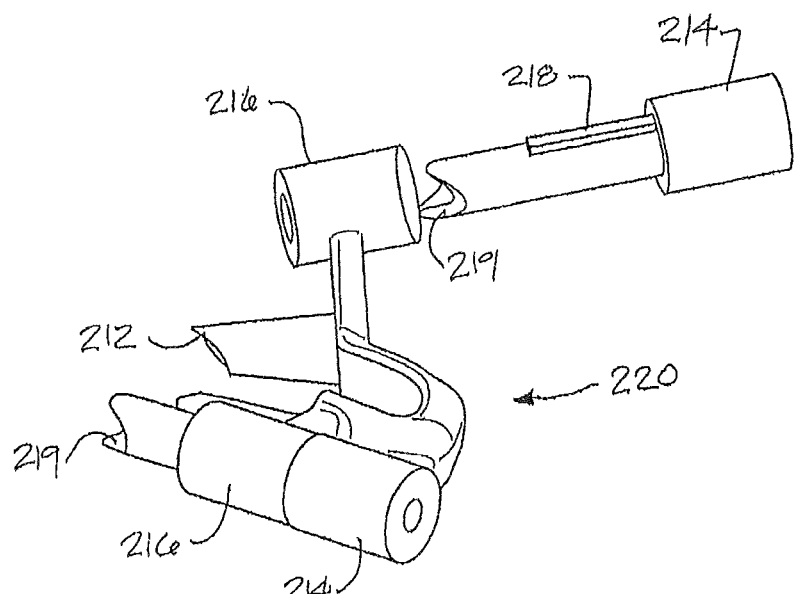
Figure 23:
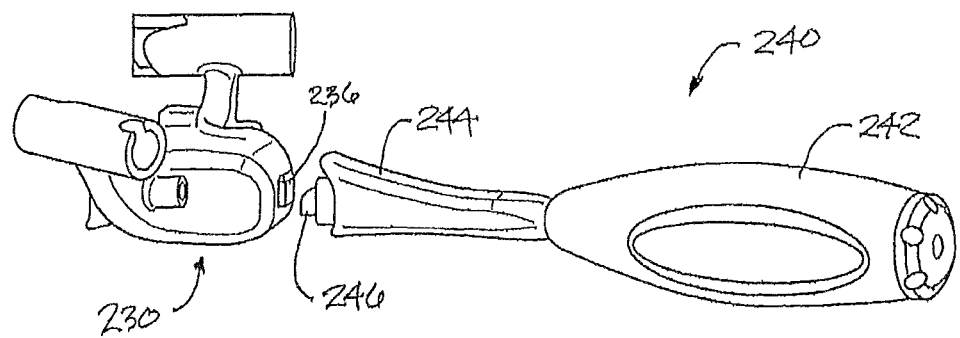
Figure 24:
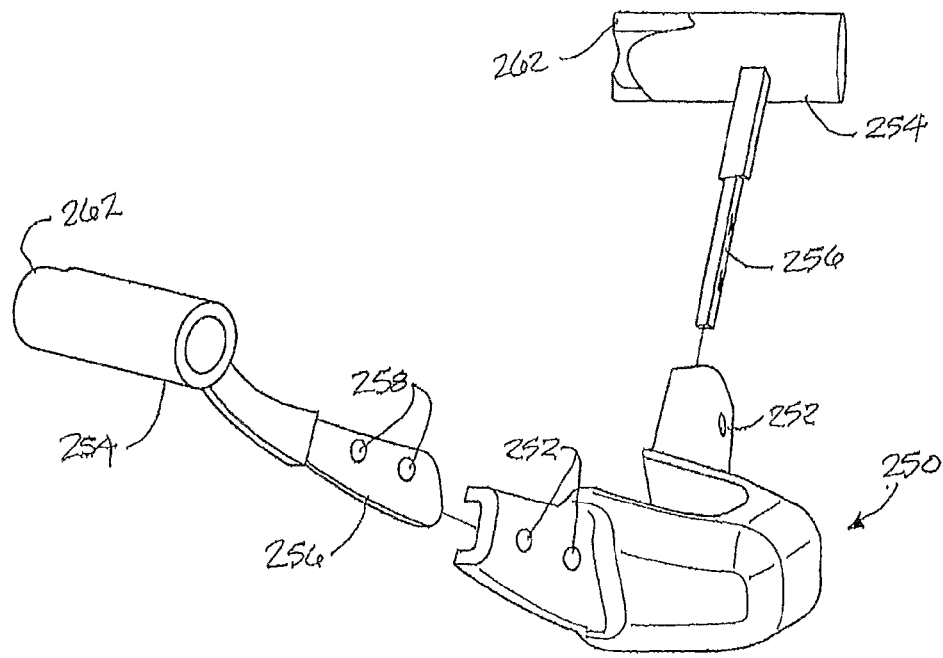
Figure 25:
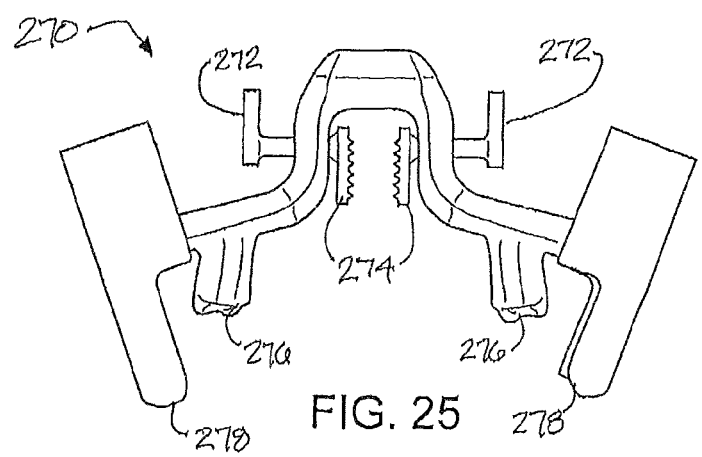
Figures 26A, 26B:
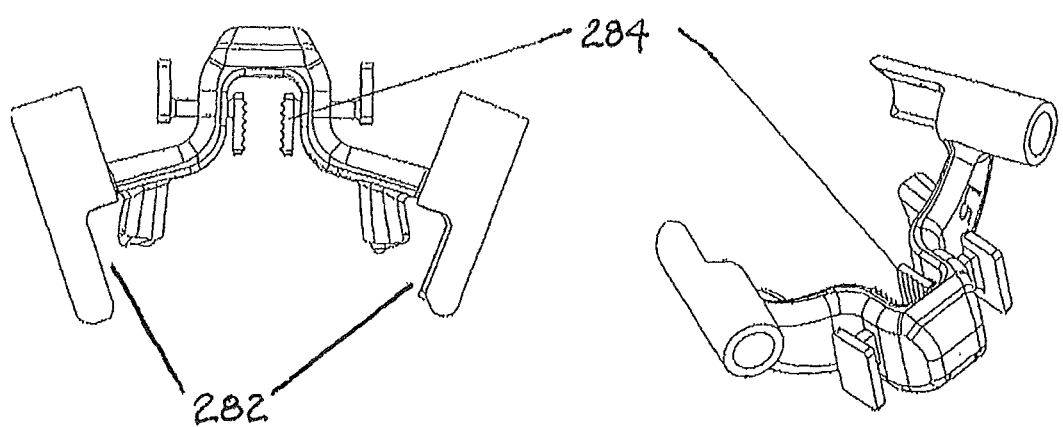
Figures 27A, 27B:
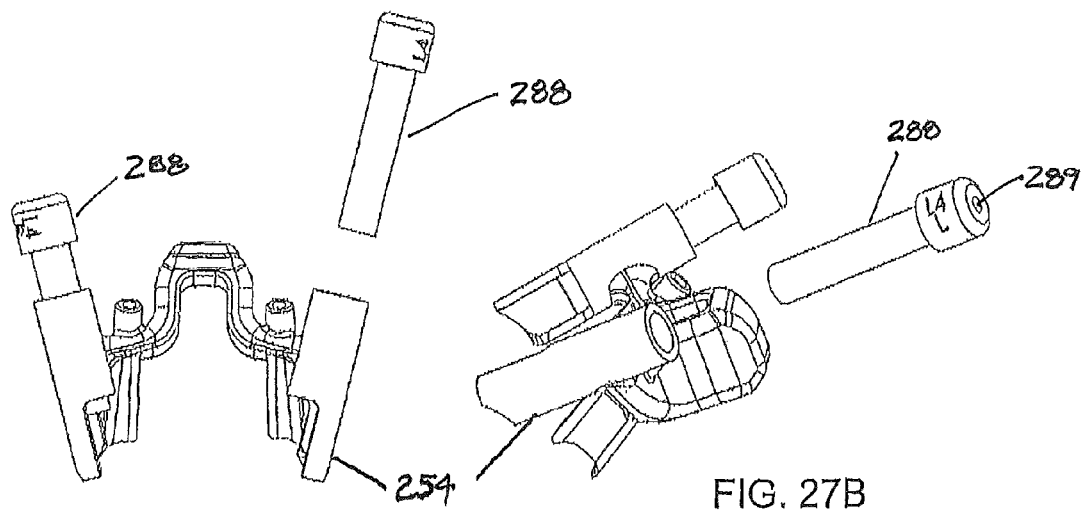
Figure 28:
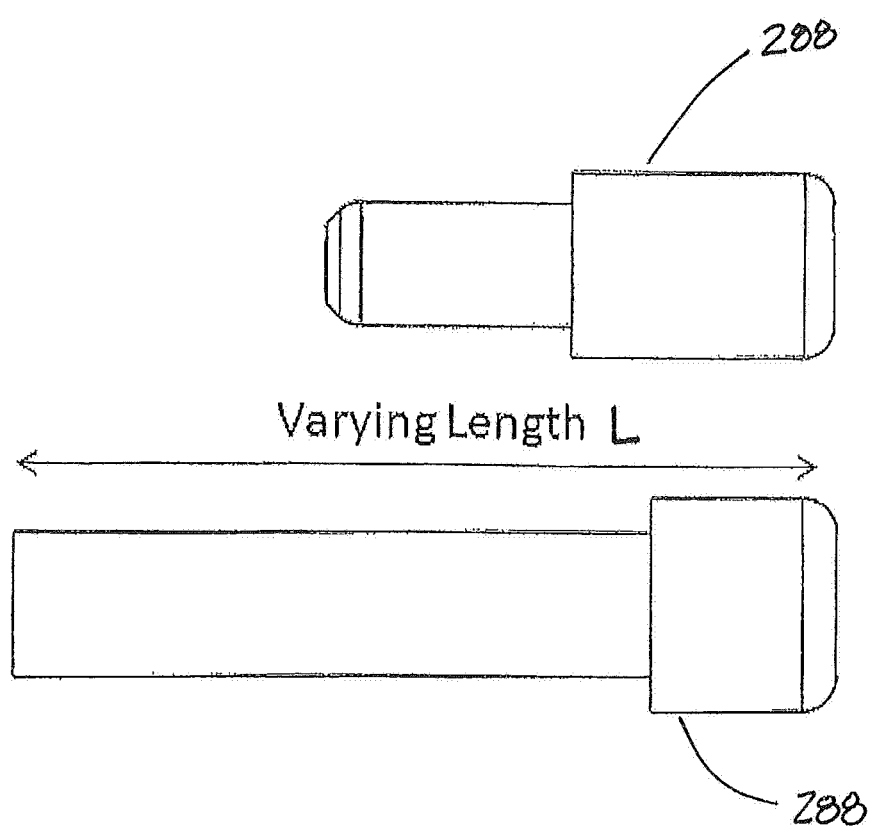
Figure 29A:
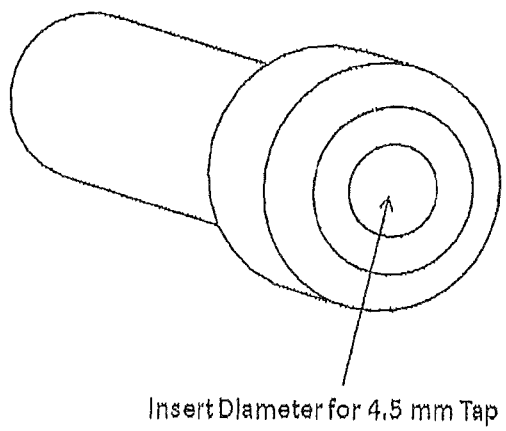
Figure 29B:
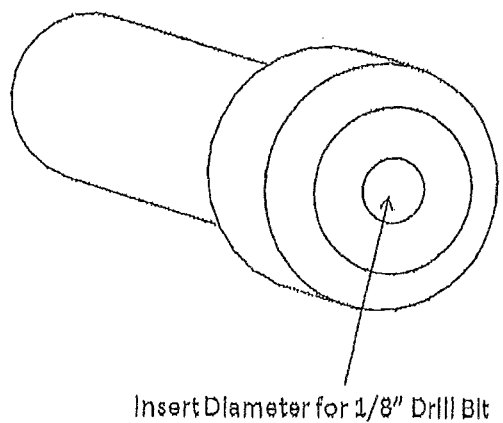
Figure 30:
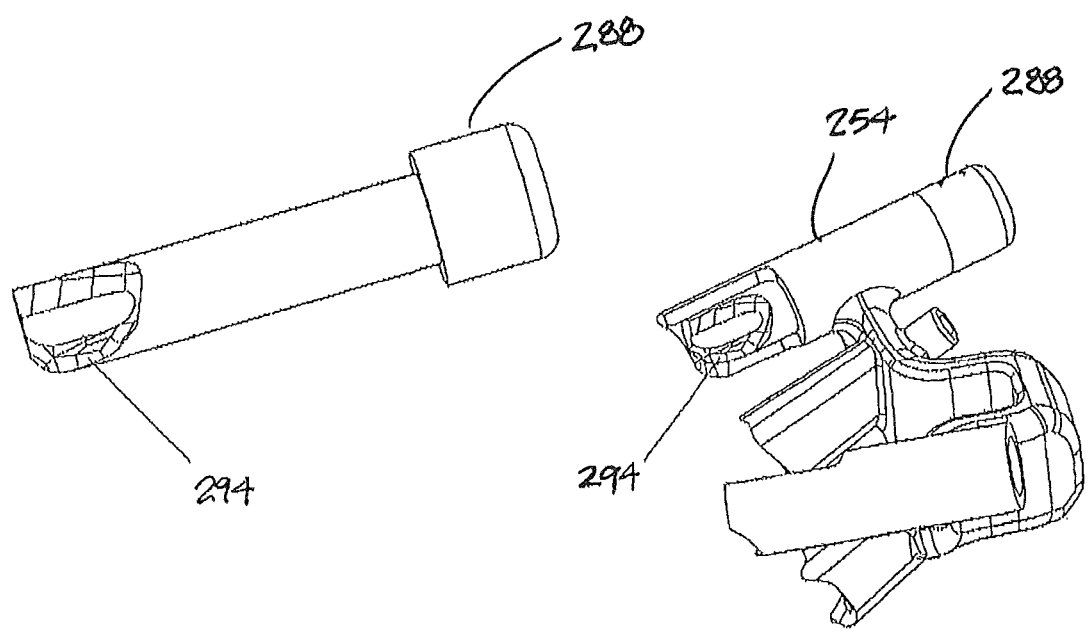
Figure 31:
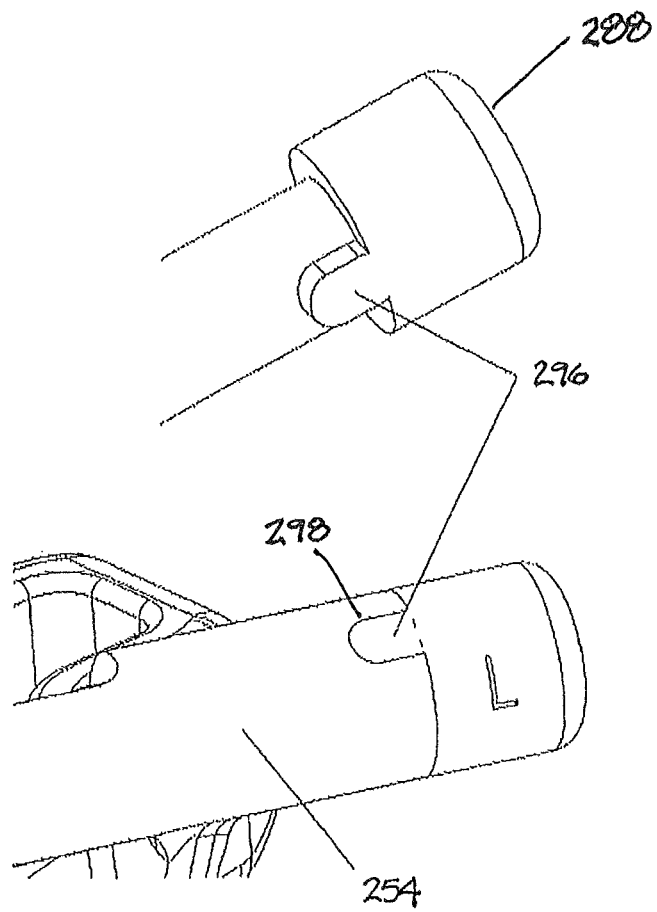
Figure 32A:
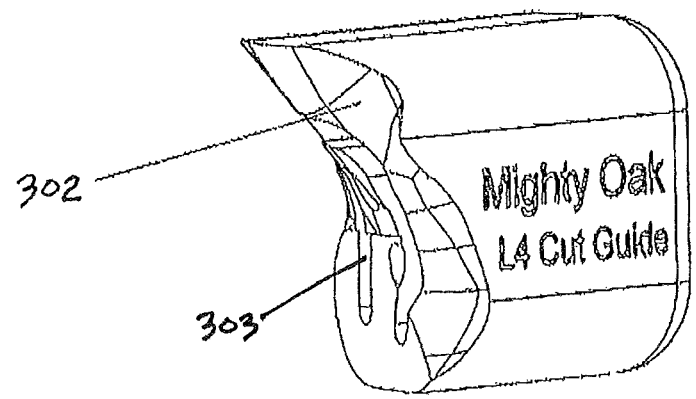
Figure 32B:
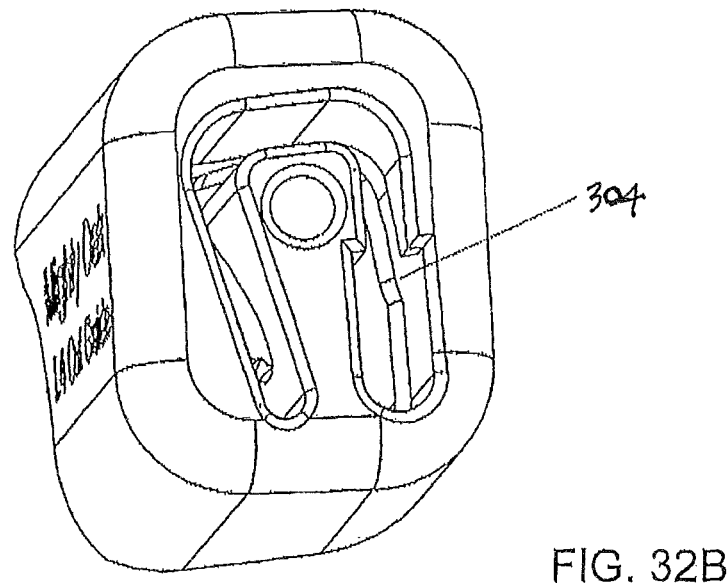
Figure 34A:
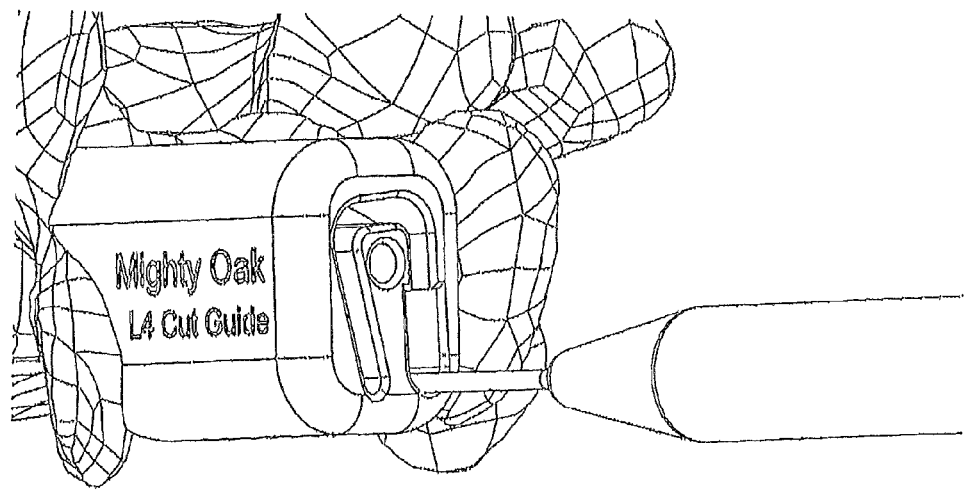
Figure 34B:
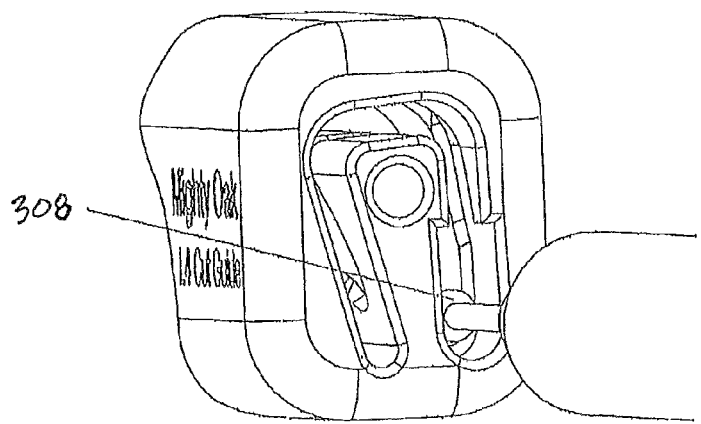
Figure 35:
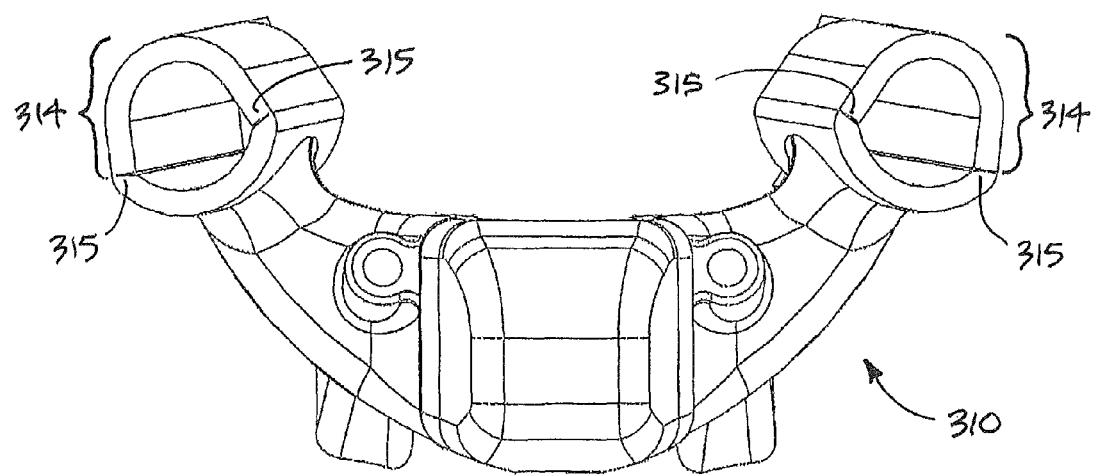
Figure 36:
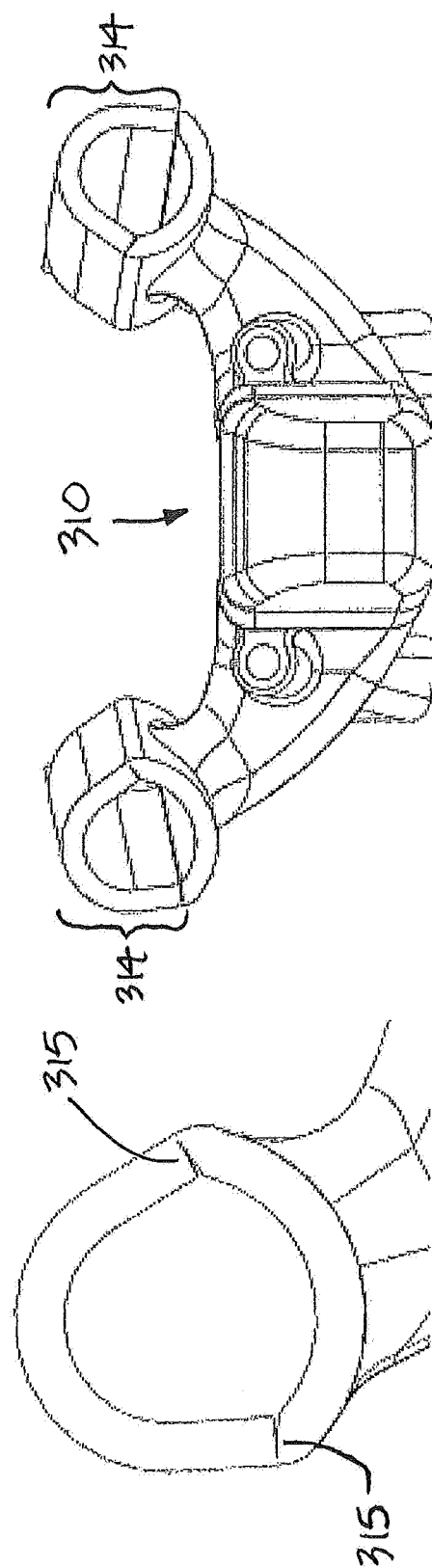
Figure 37:
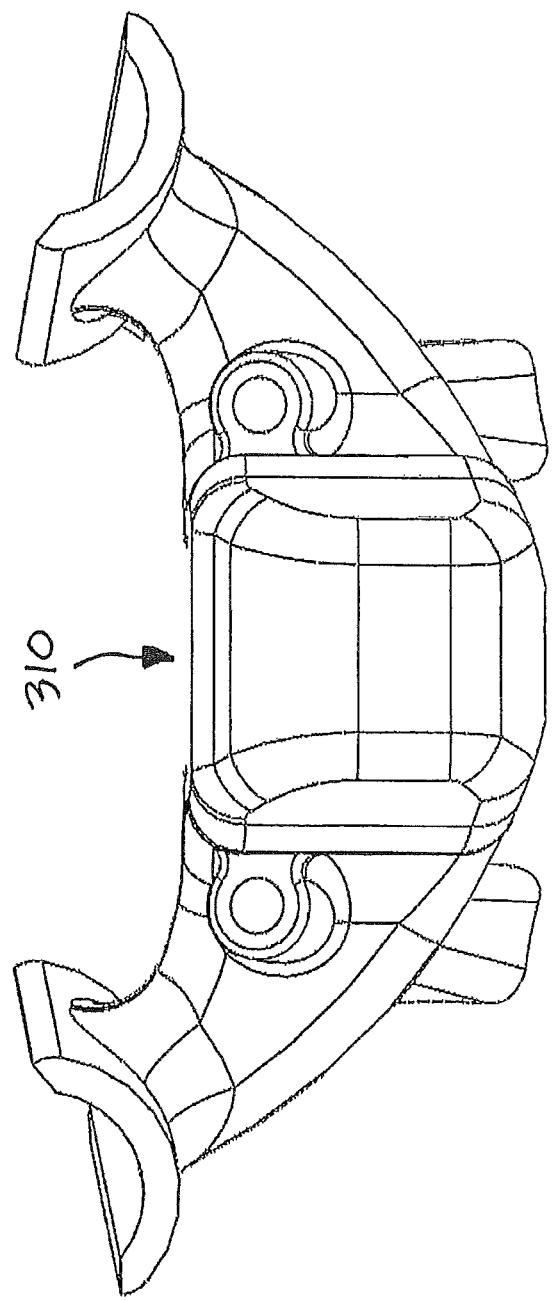
Figure 38:
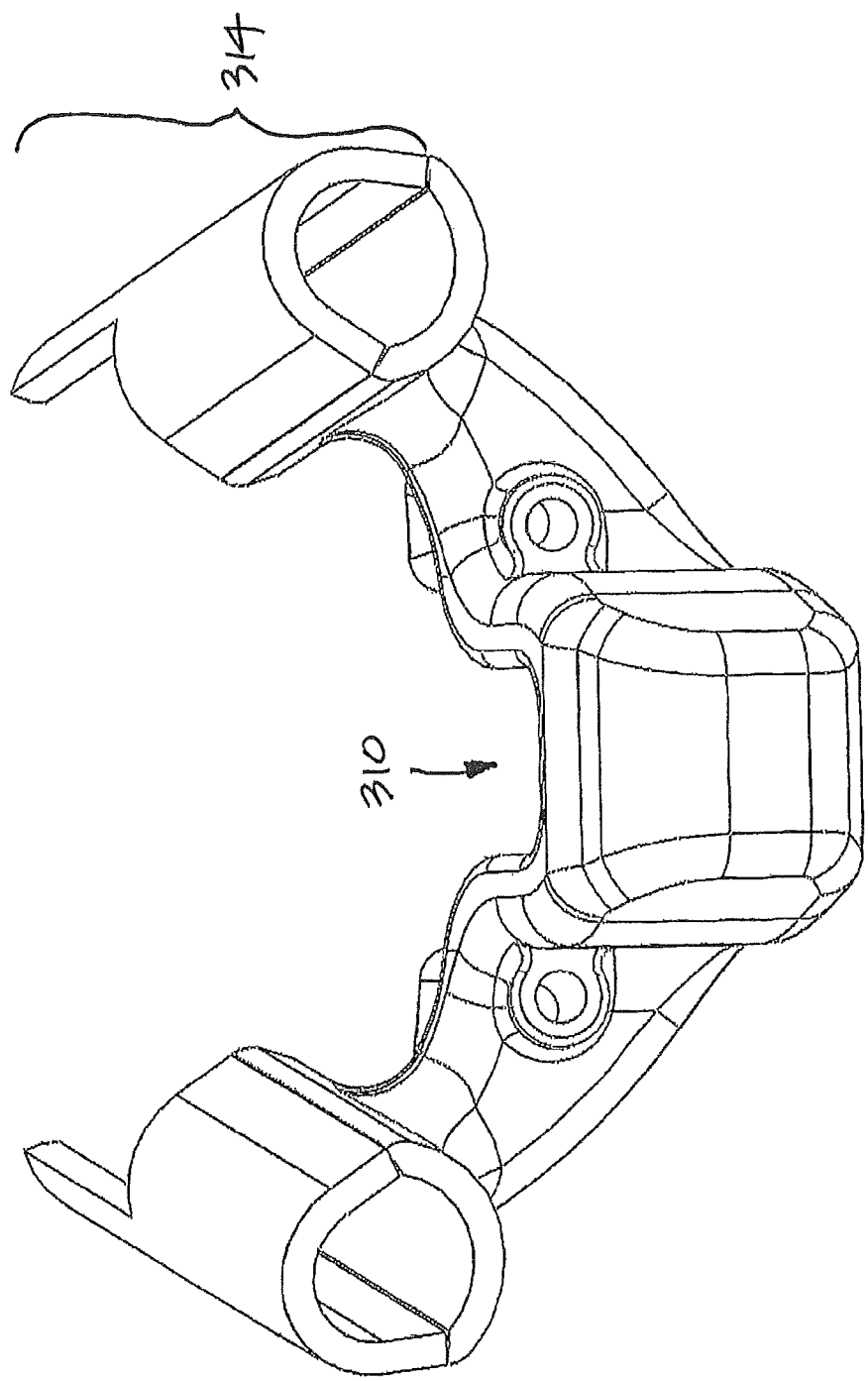
Figure 39:
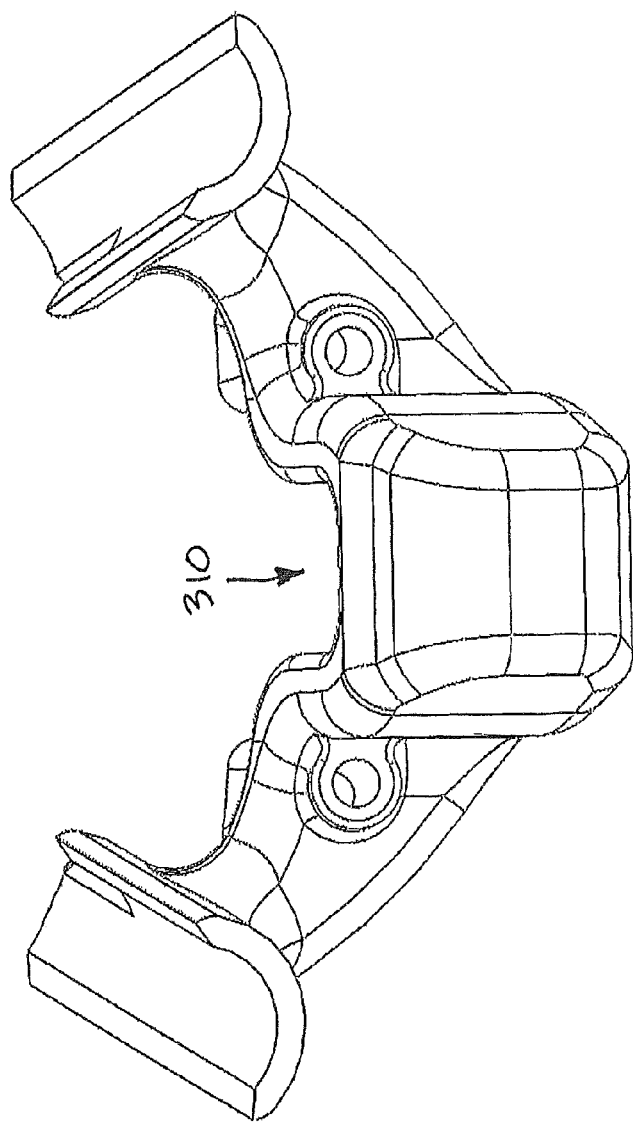
Figure 40:
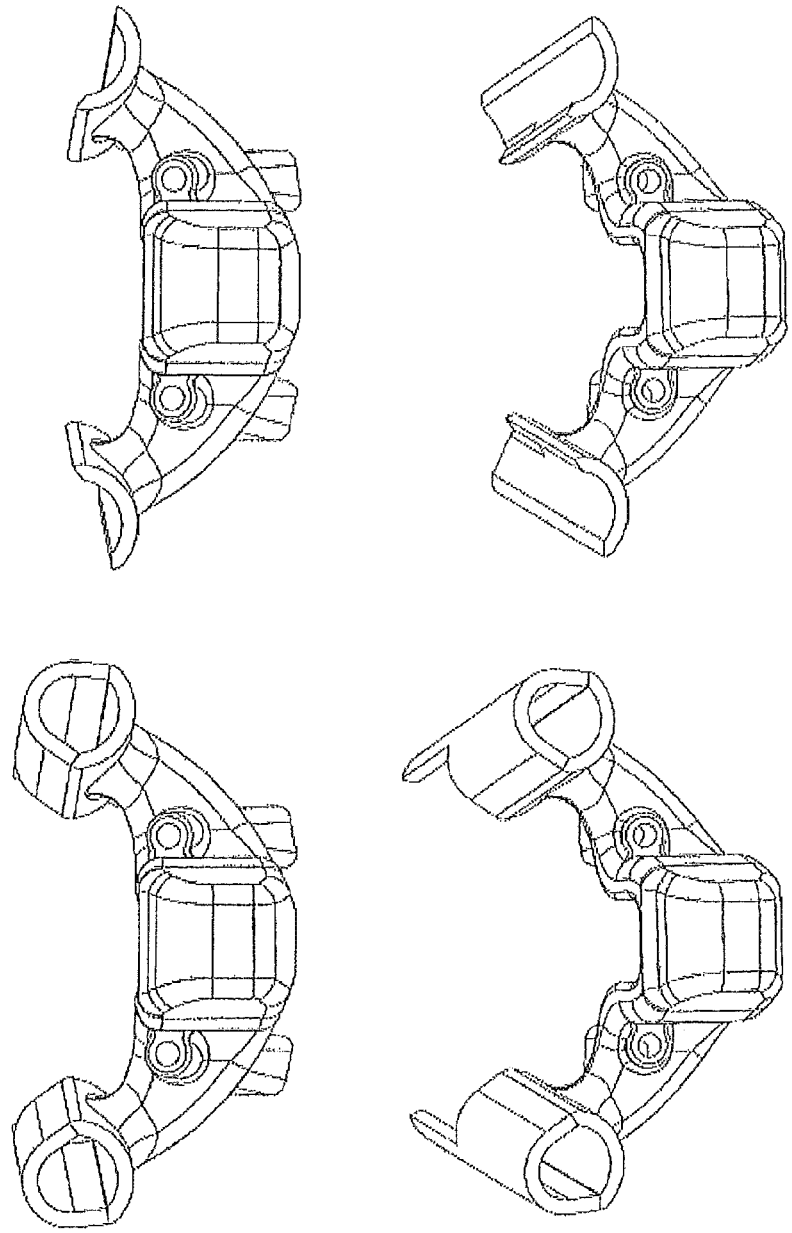
Figure 41:
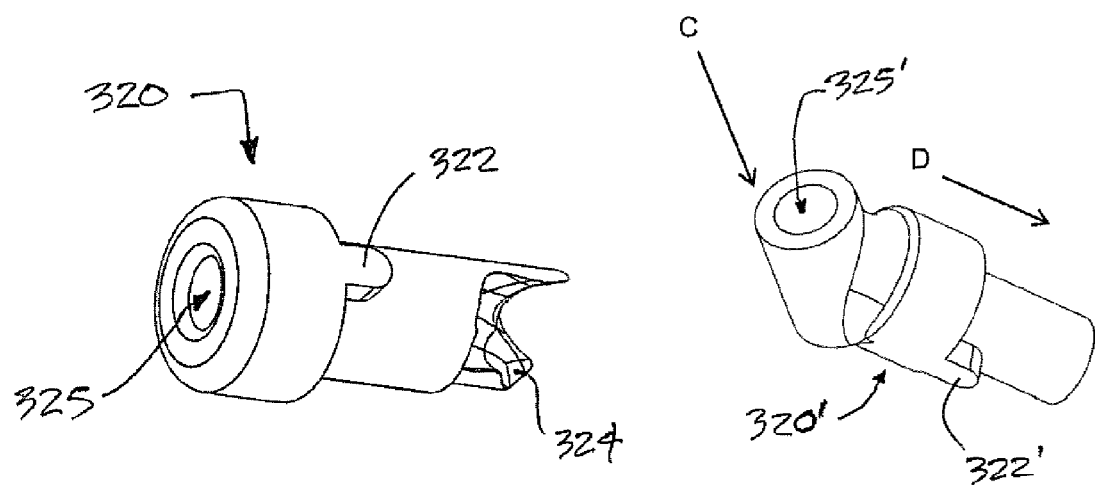
Figure 42A:
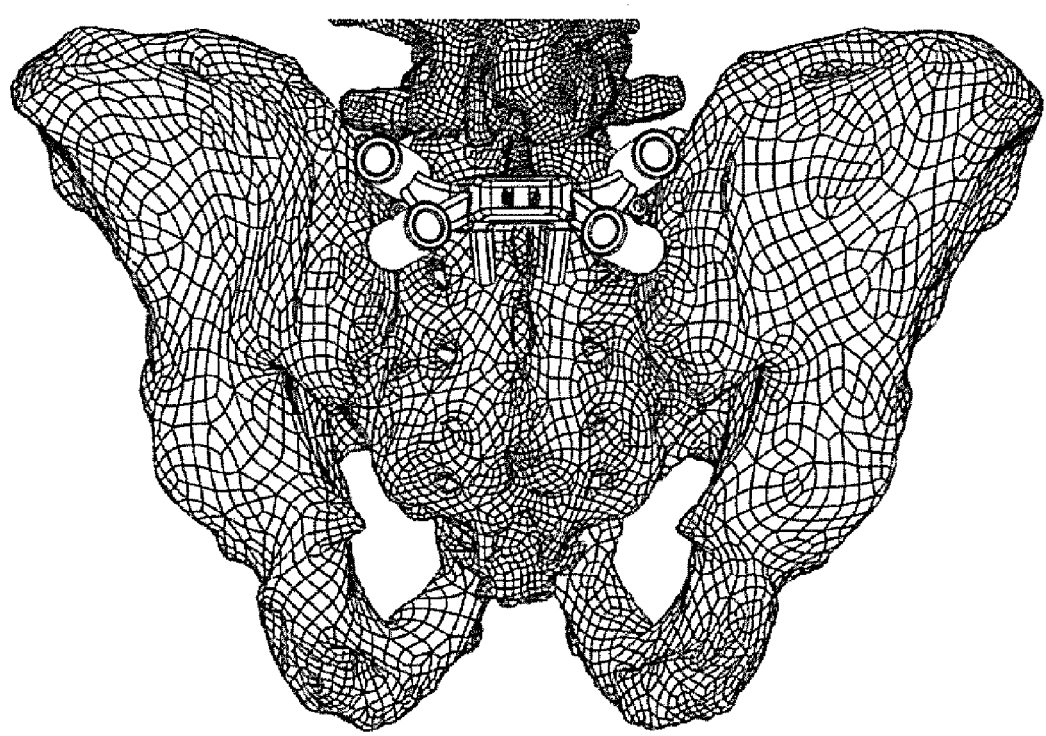
Figure 42B:
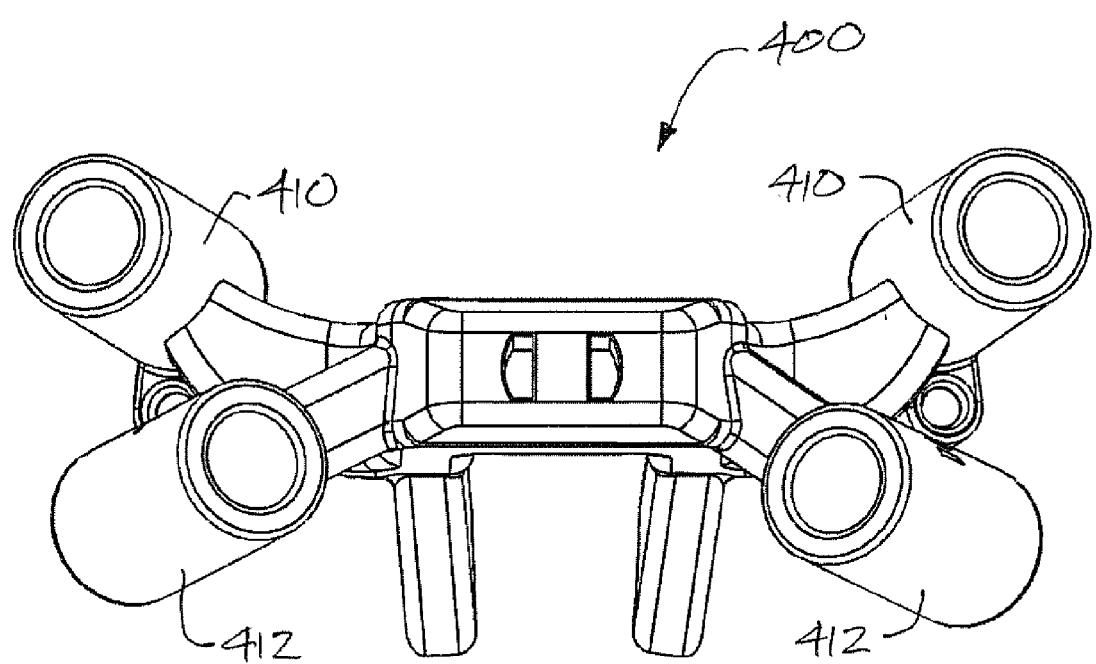
Figure 43A:
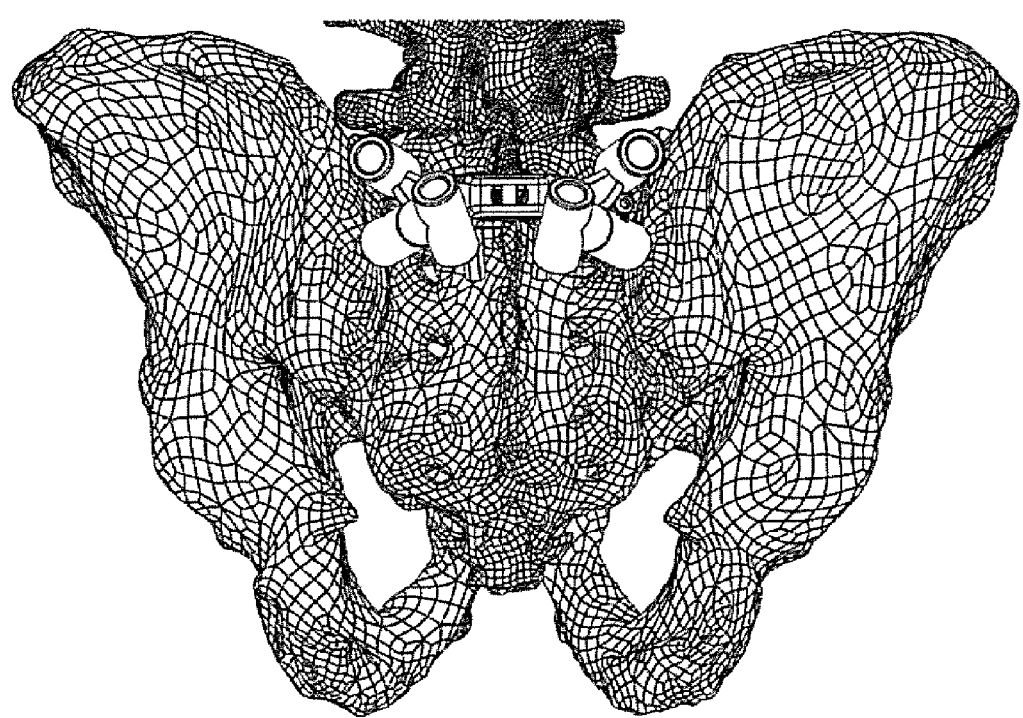
Figure 43B:
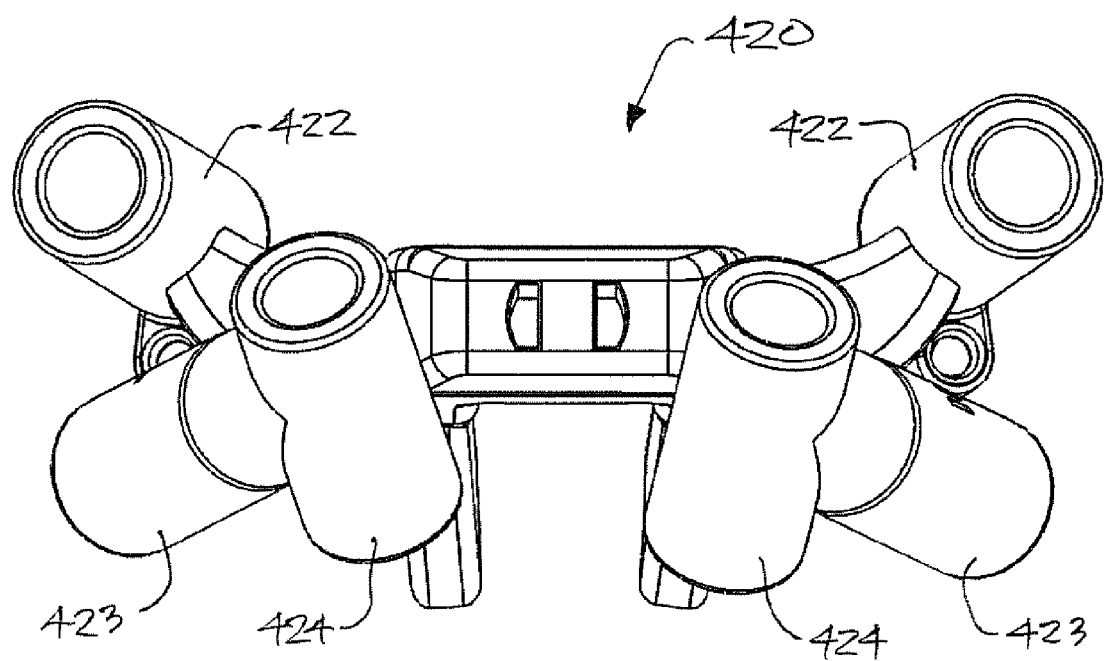
Figure 44A:
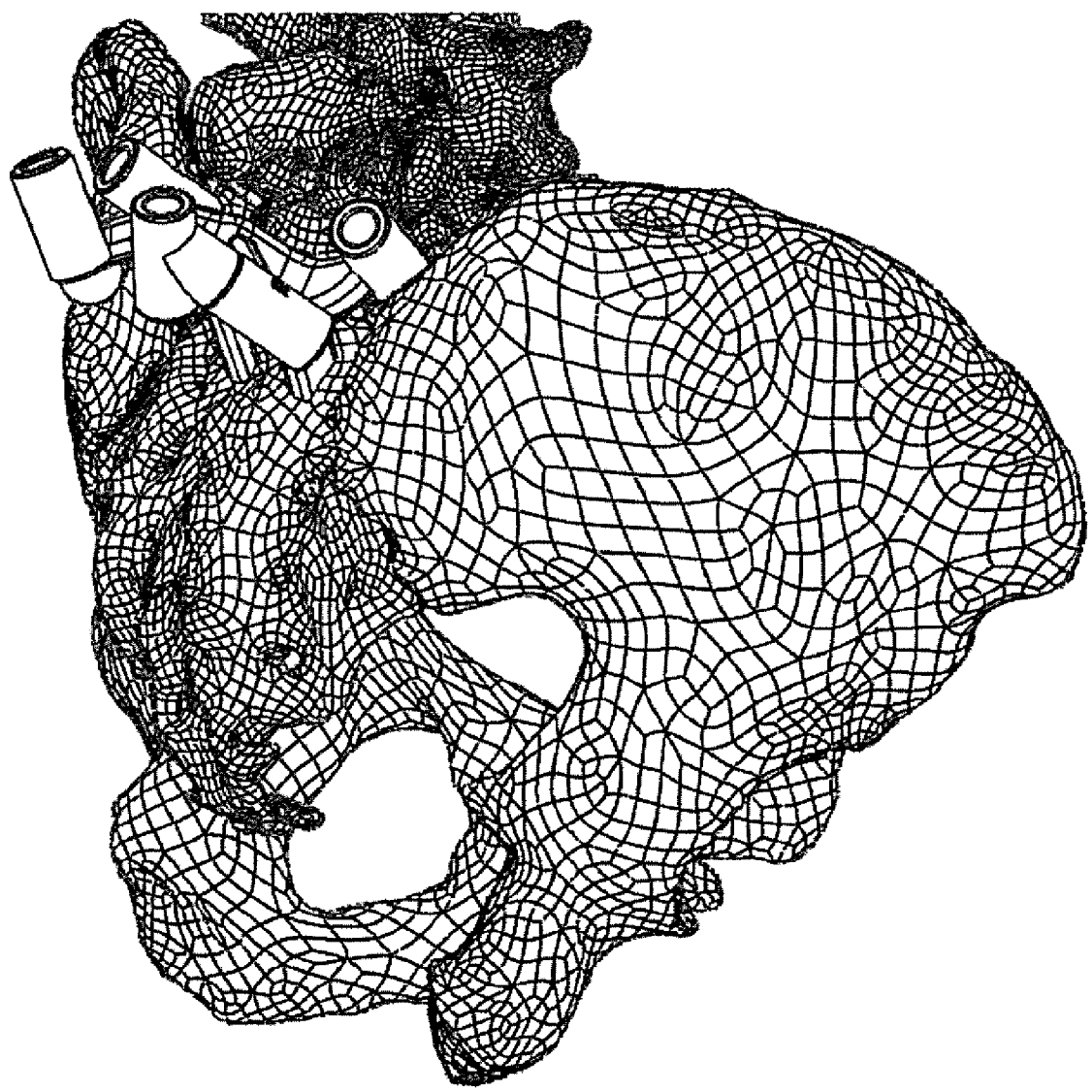
Figure 44B:
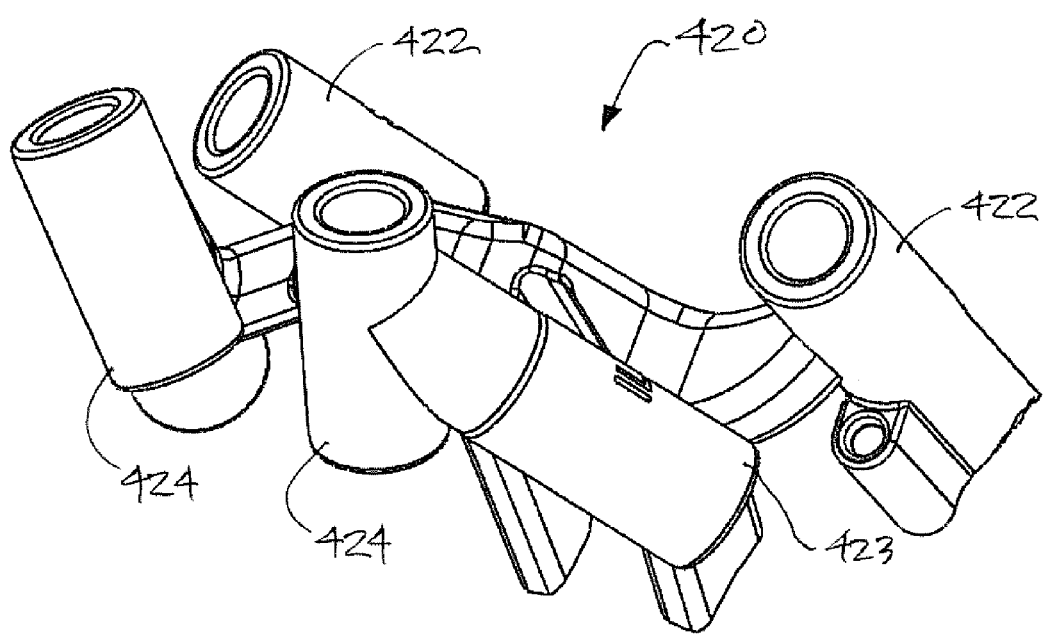
Figure 45:
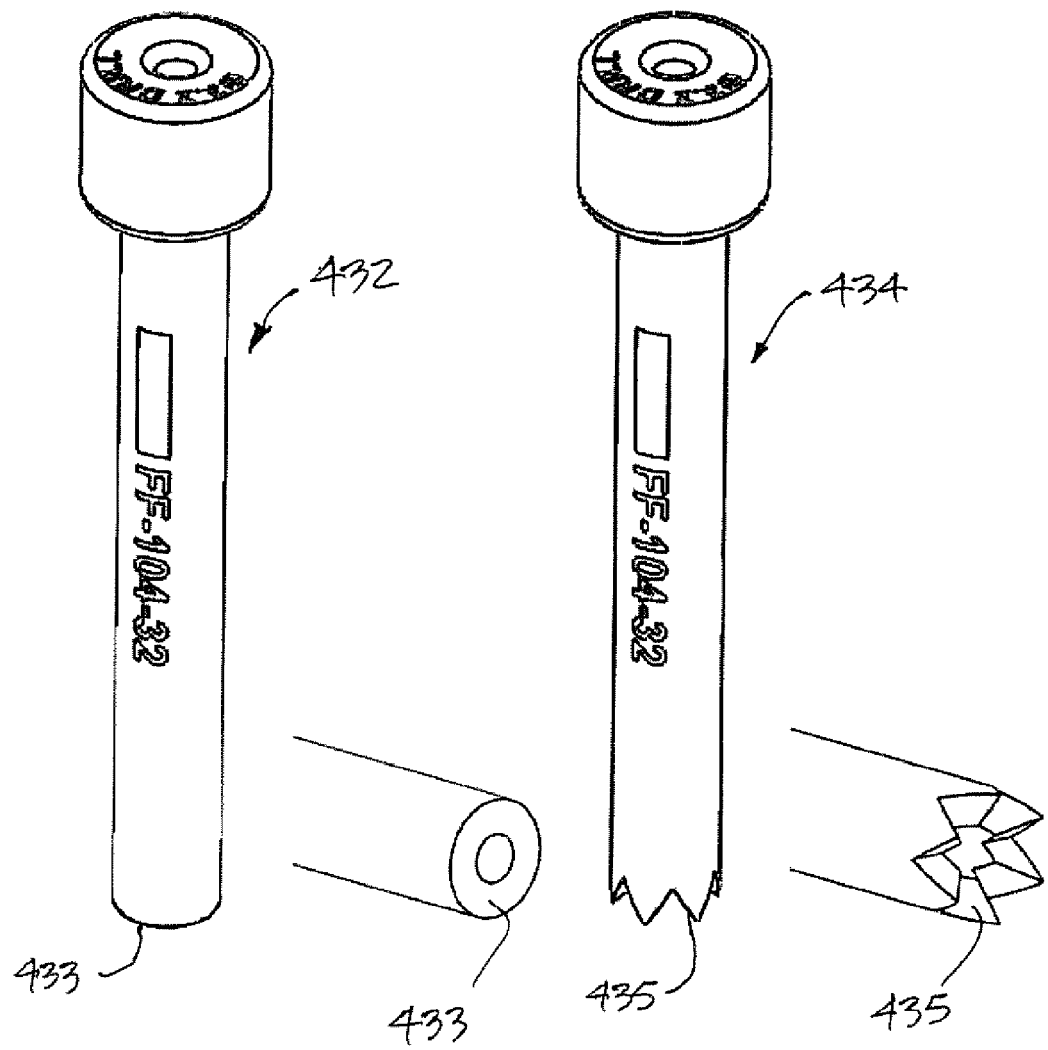
Figure 46:
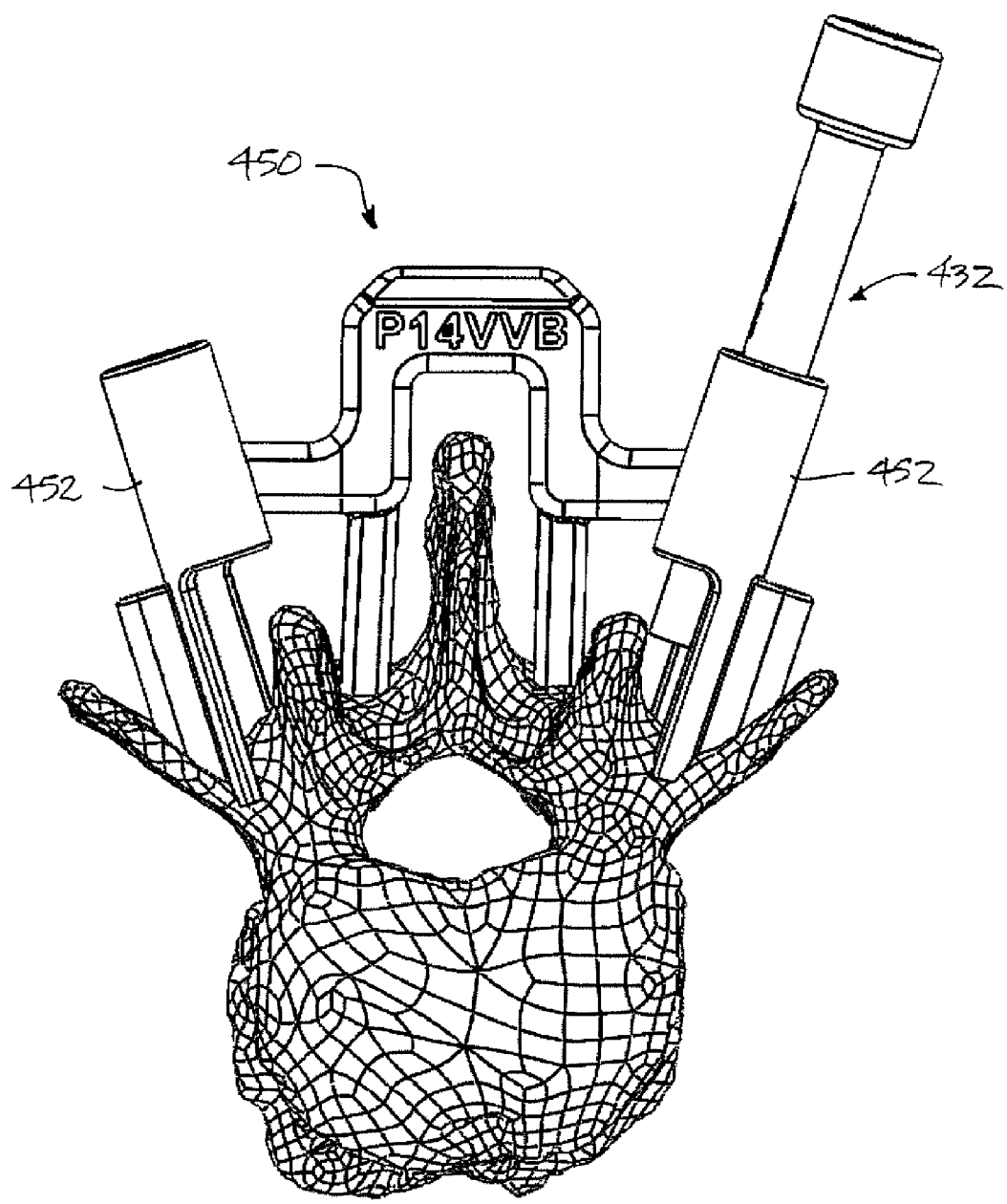
Figure 47A:
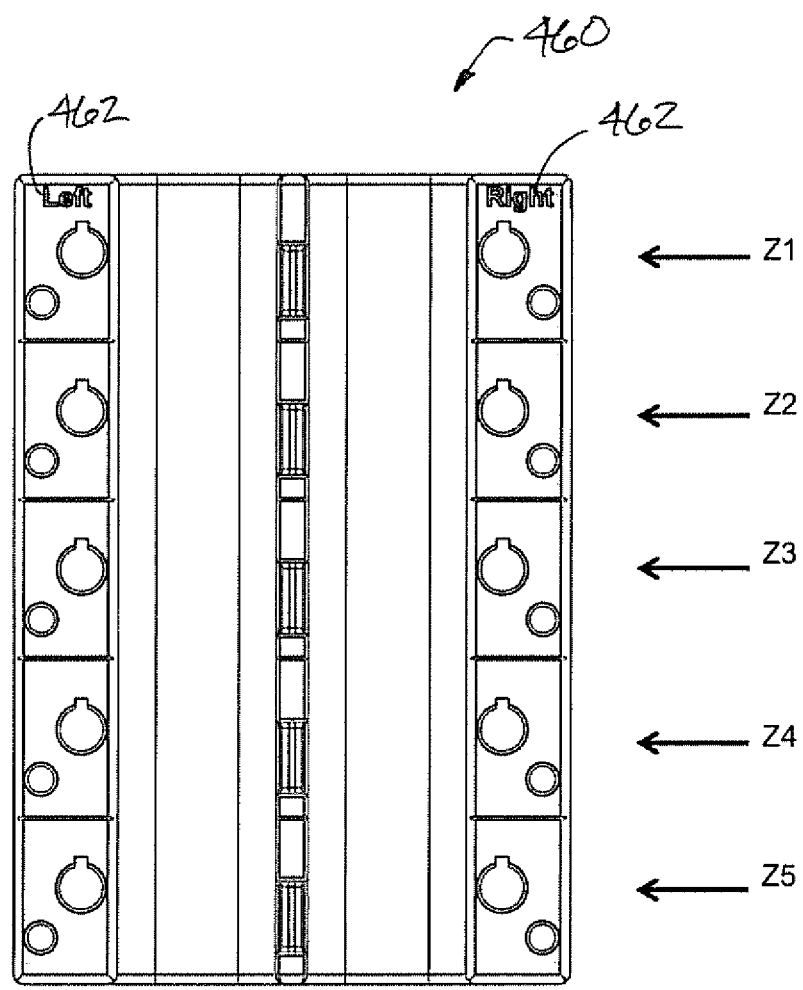
Figure 47B:
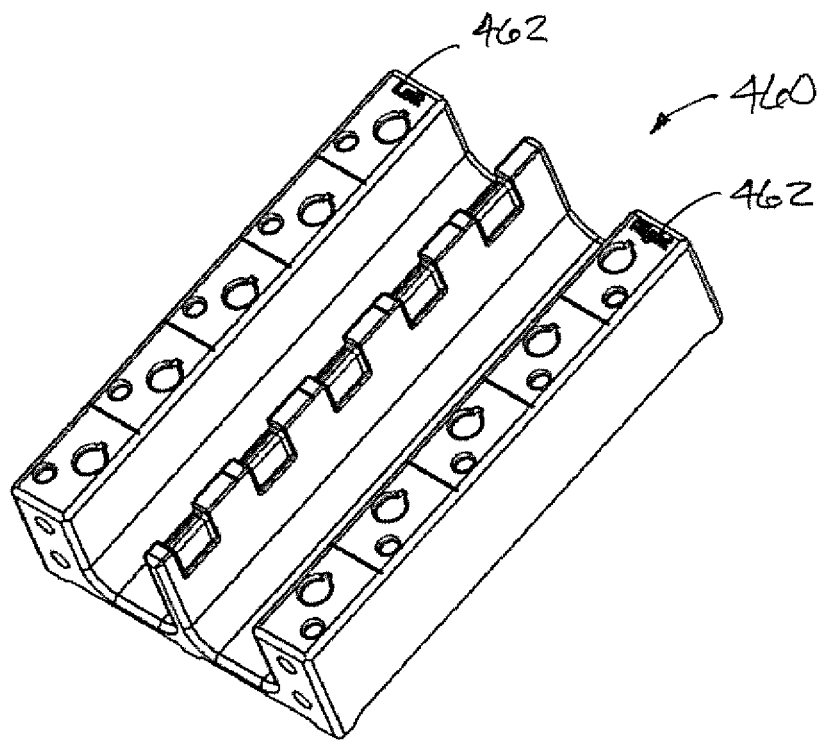
Figure 47C:
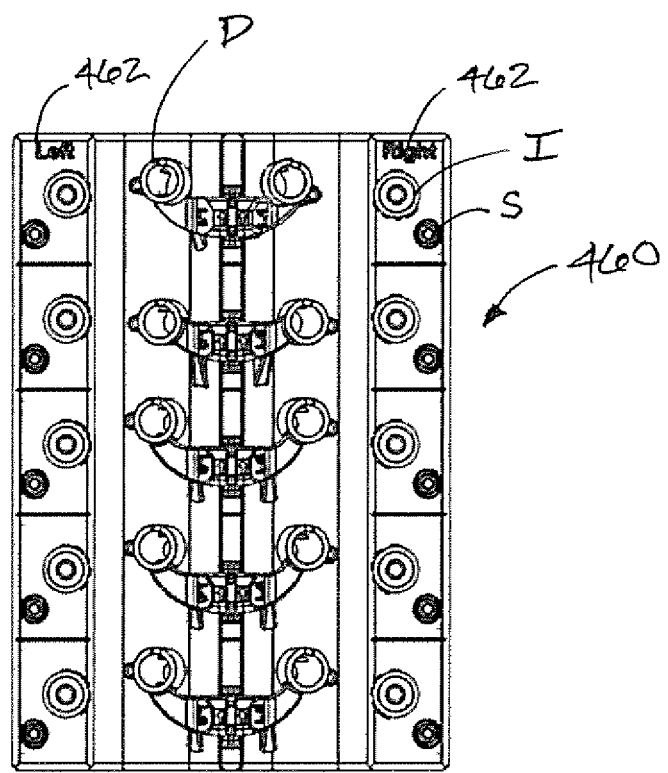
Figure 47D:
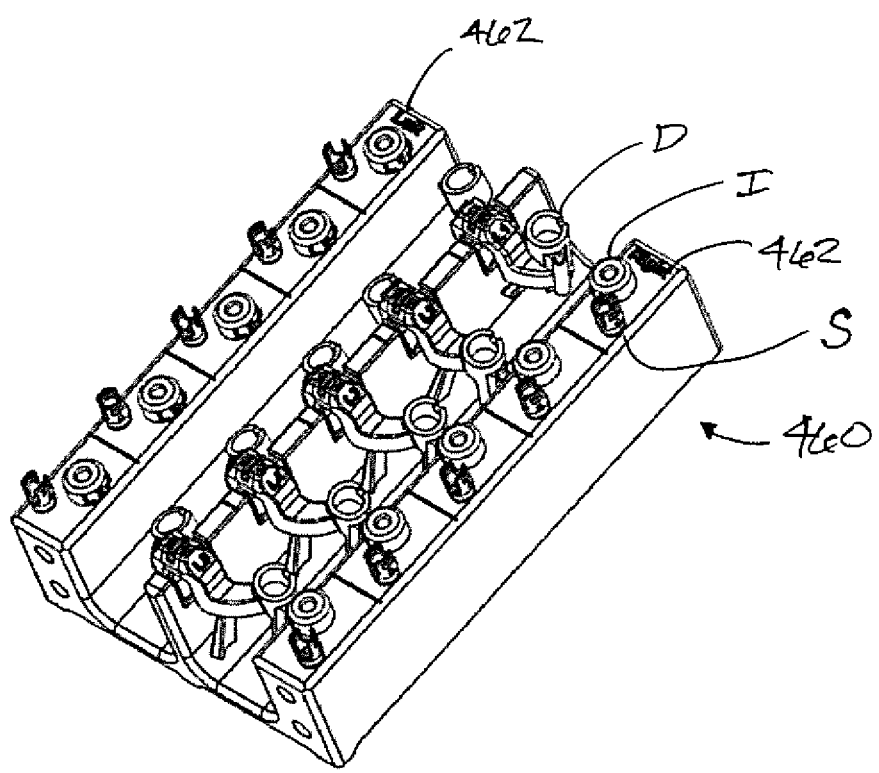
Figure 48A:
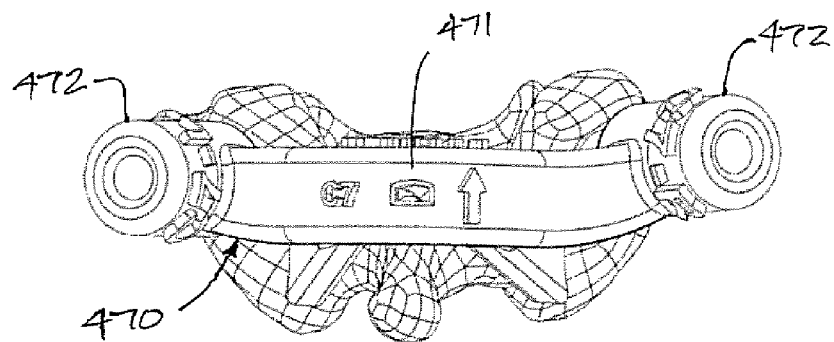
Figure 48B:
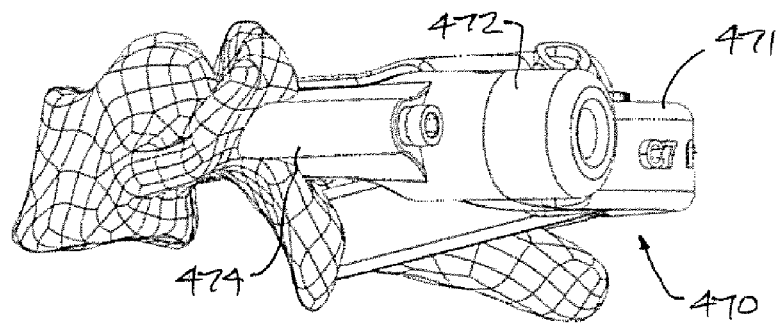
Figure 48C:
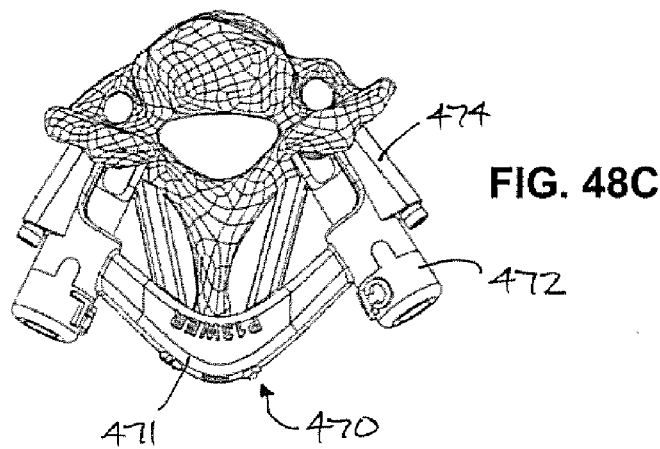
Figure 49A:
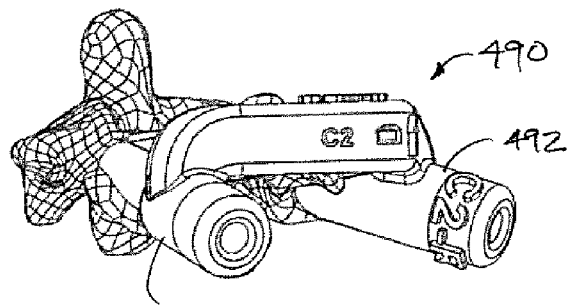
Figure 49B:
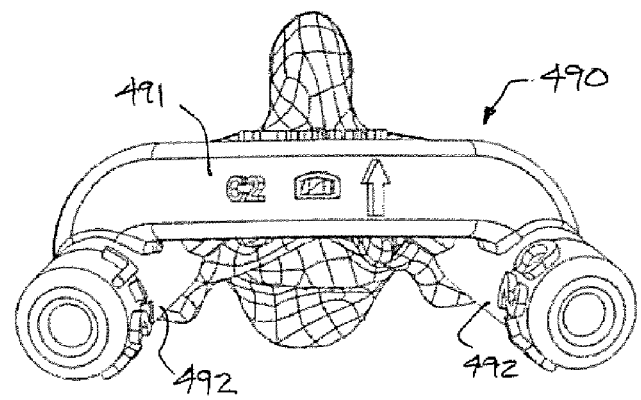
Figure 49C:
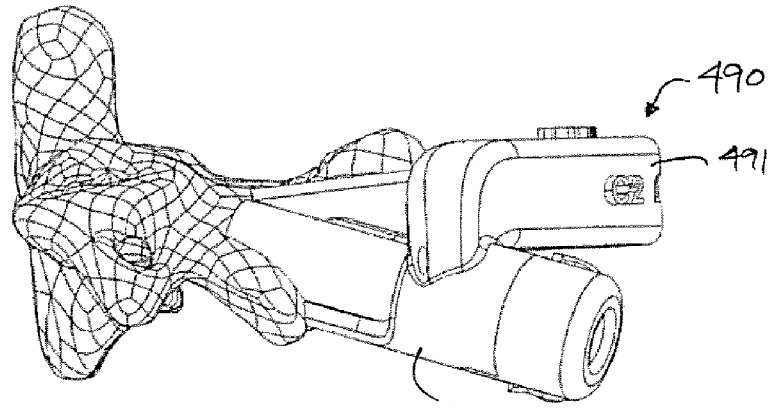
Figures 50A, 50B:
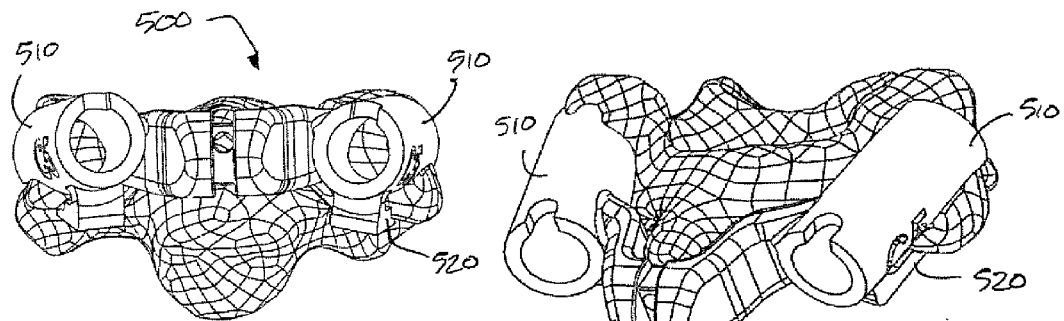
Figures 50C, 50D:
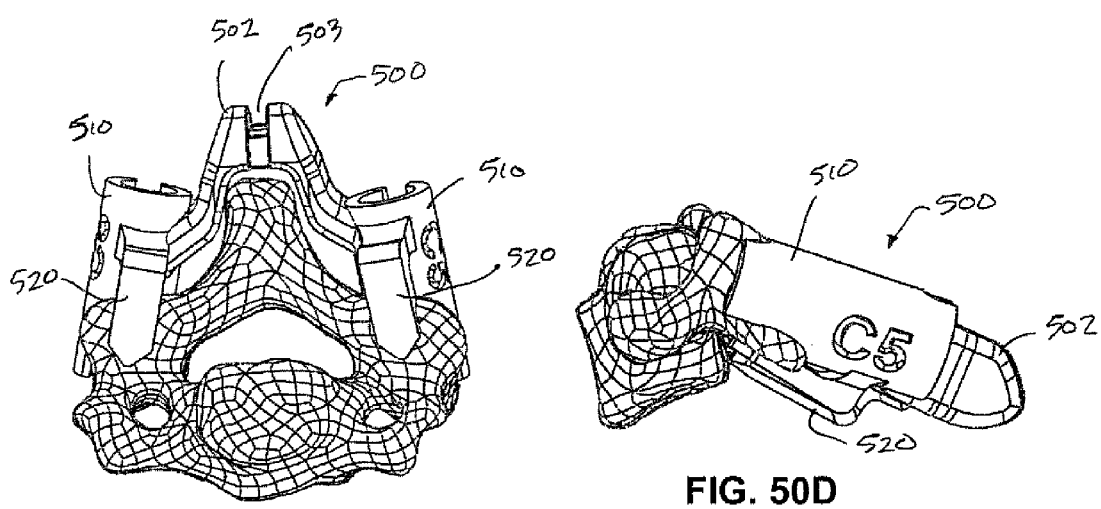
Figure 52A:
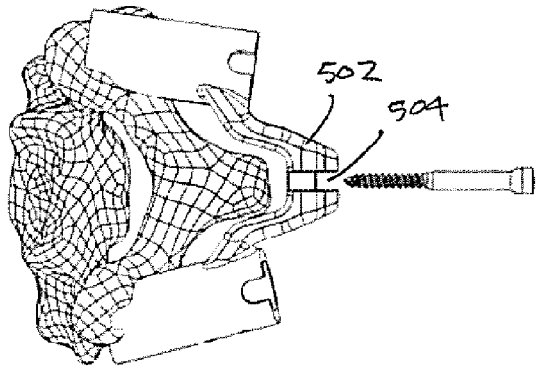
Figure 52B:
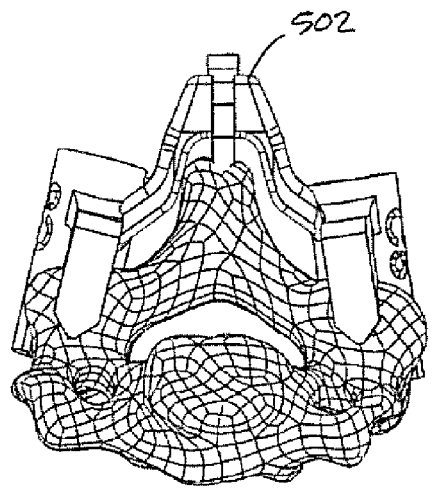
Figure 52C:
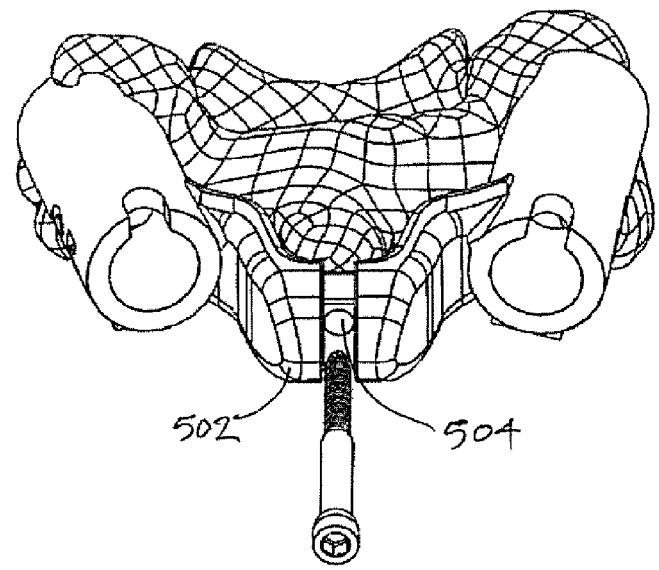
Figure 54A:
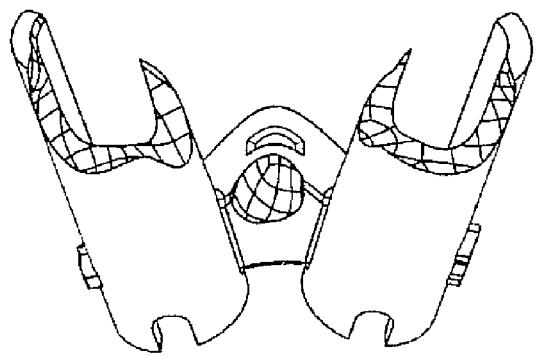
Figure 54B:
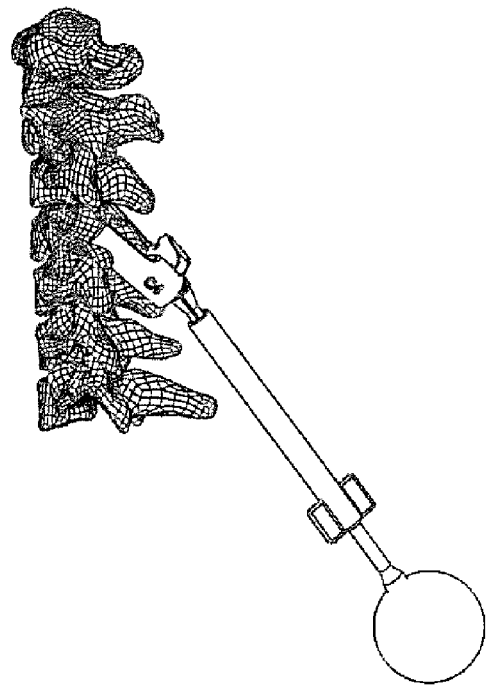
Figure 54C:
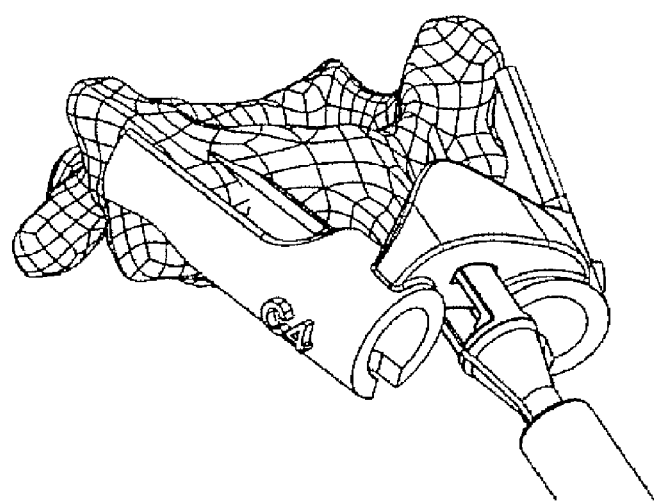
Figure 56A:
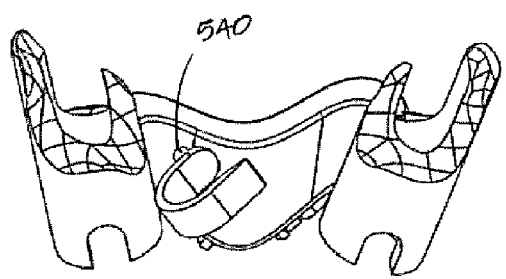
Figure 56B:
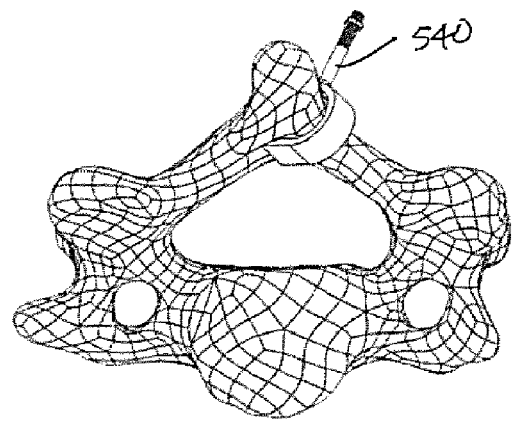
Figure 56C:
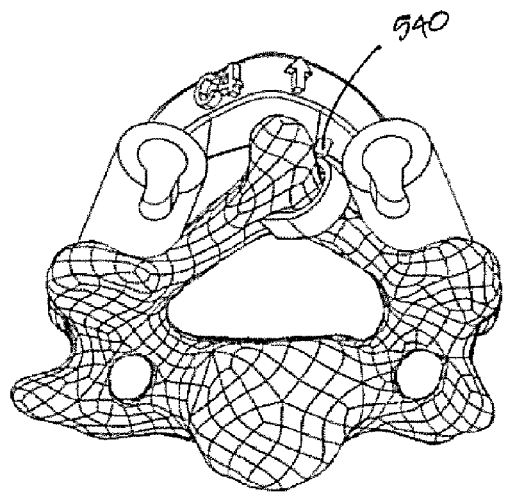
Figure 56D:
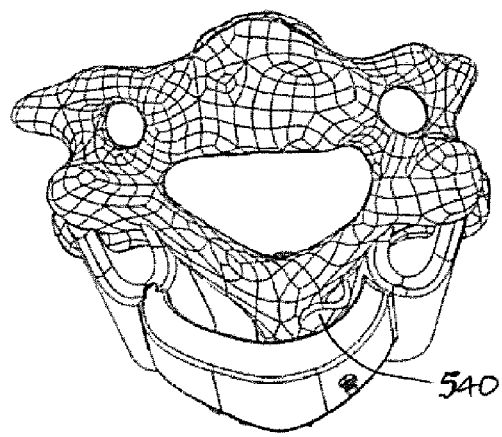
Figure 57:
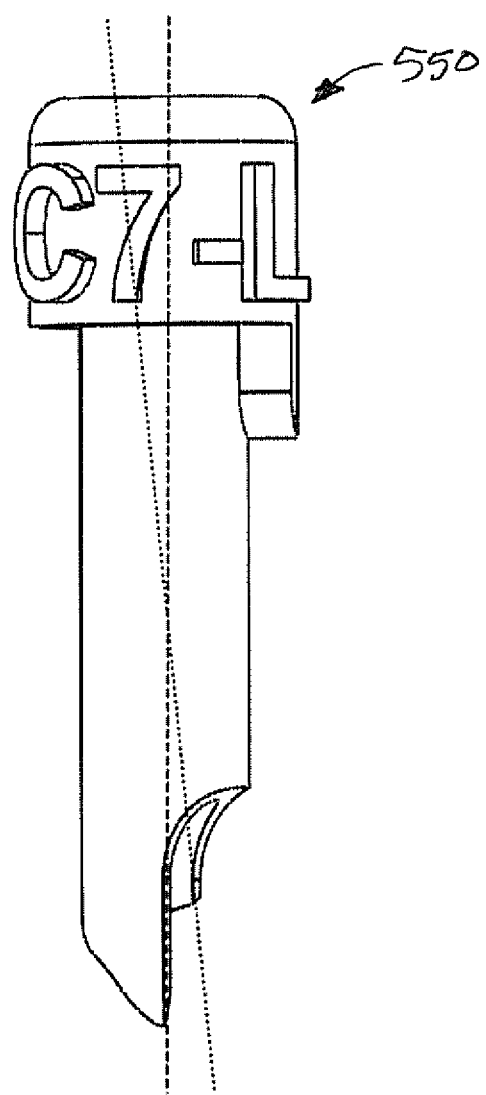
Figure 58A:
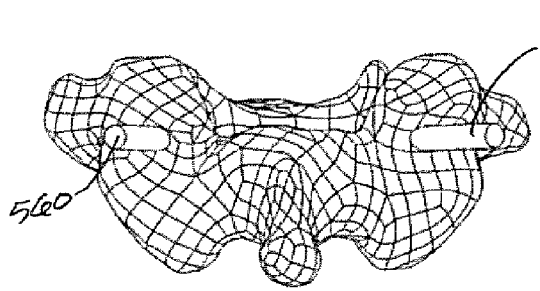
Figure 58B:
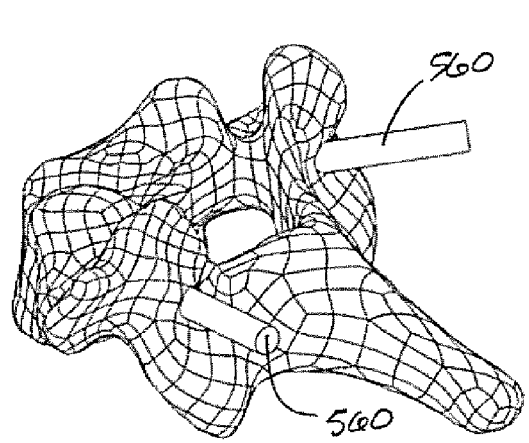
Figure 58C:
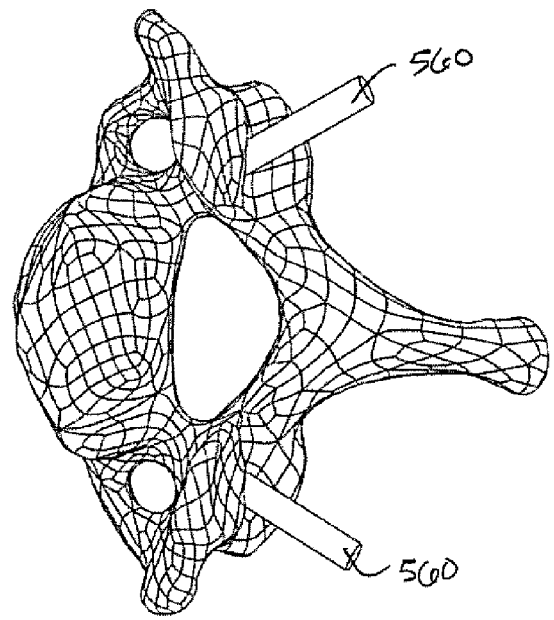
Figure 61A:
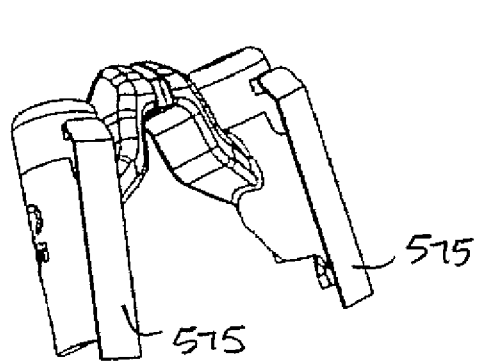
Figure 61B:
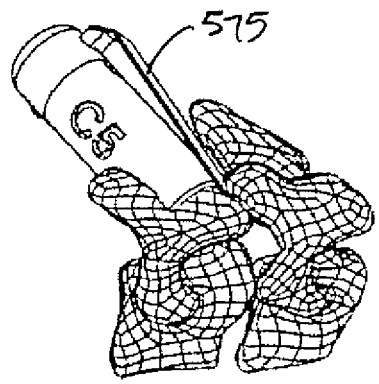
Figure 61C:
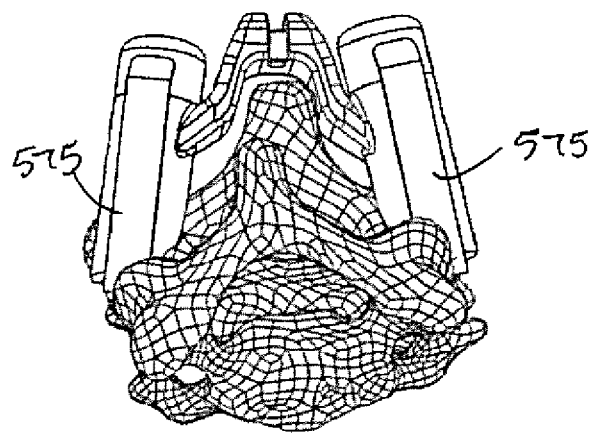
Figure 64:
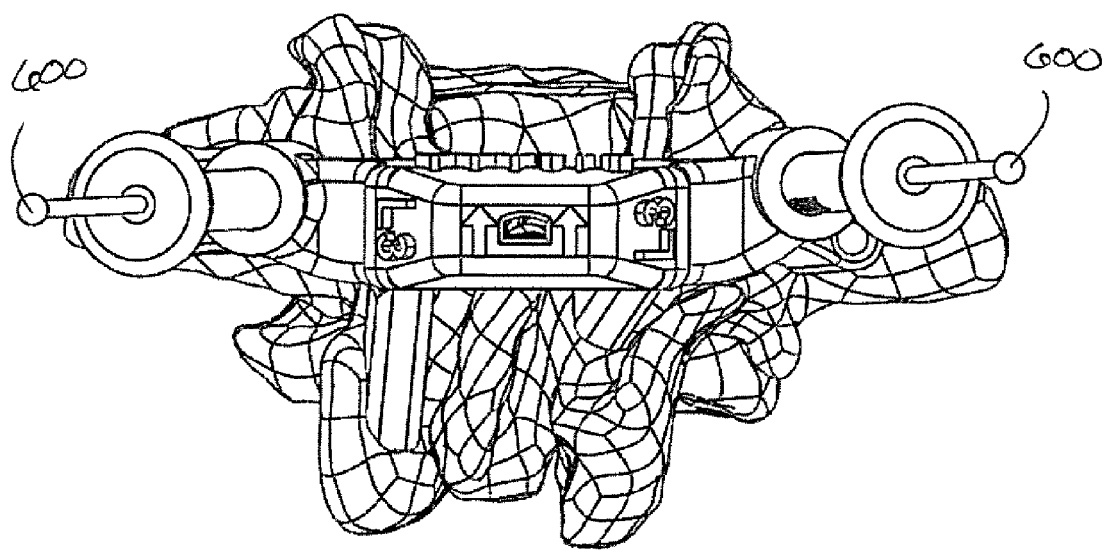
Figure 65:
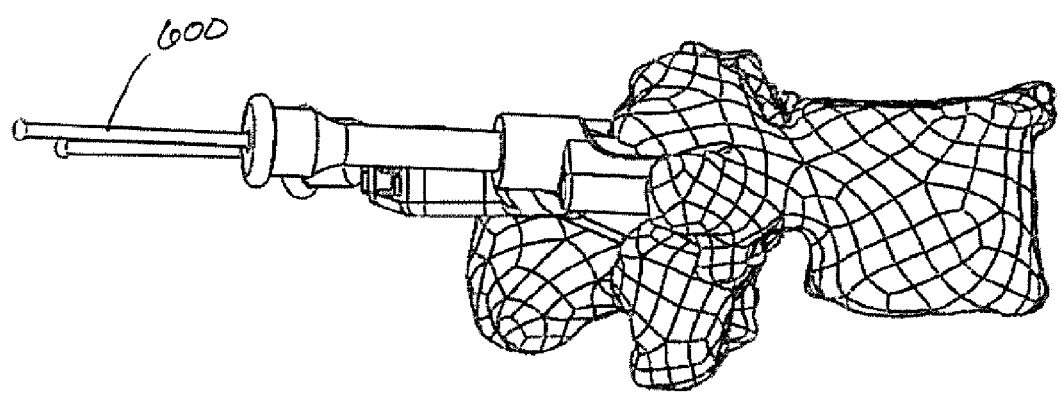
Figure 66:
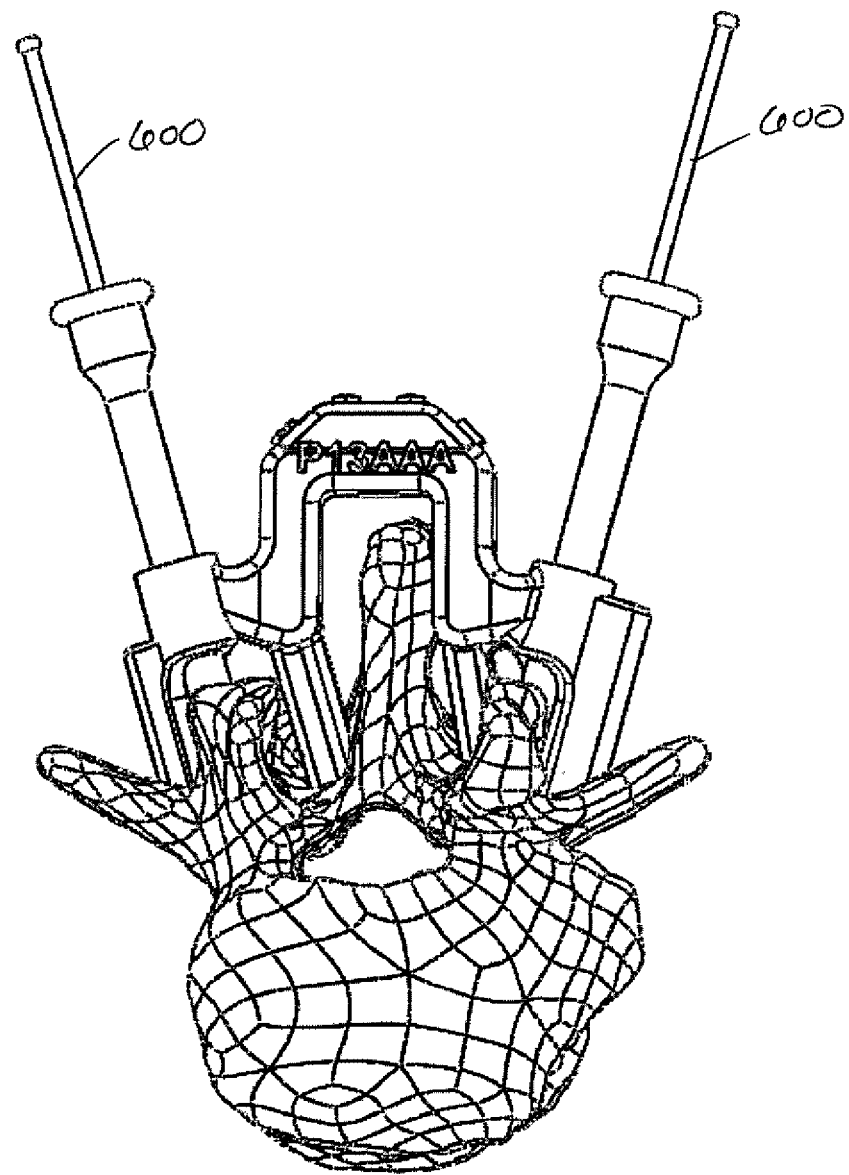
Figure 67:
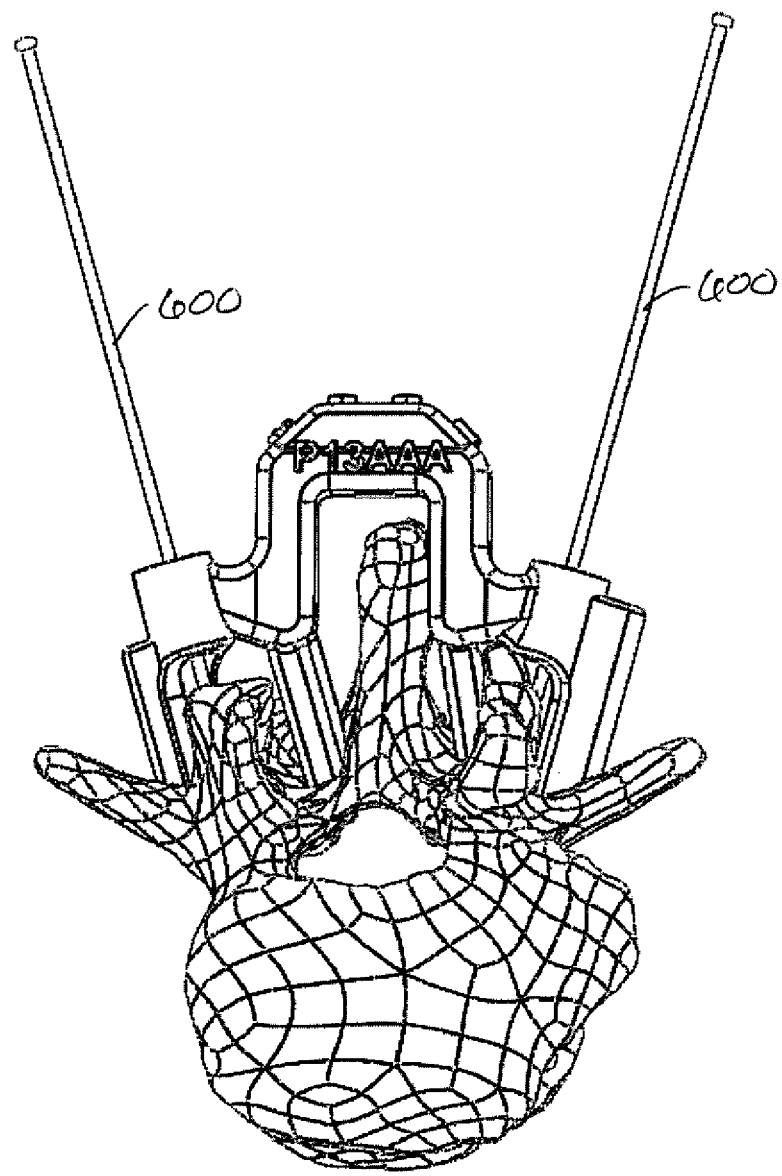
Figure 68:
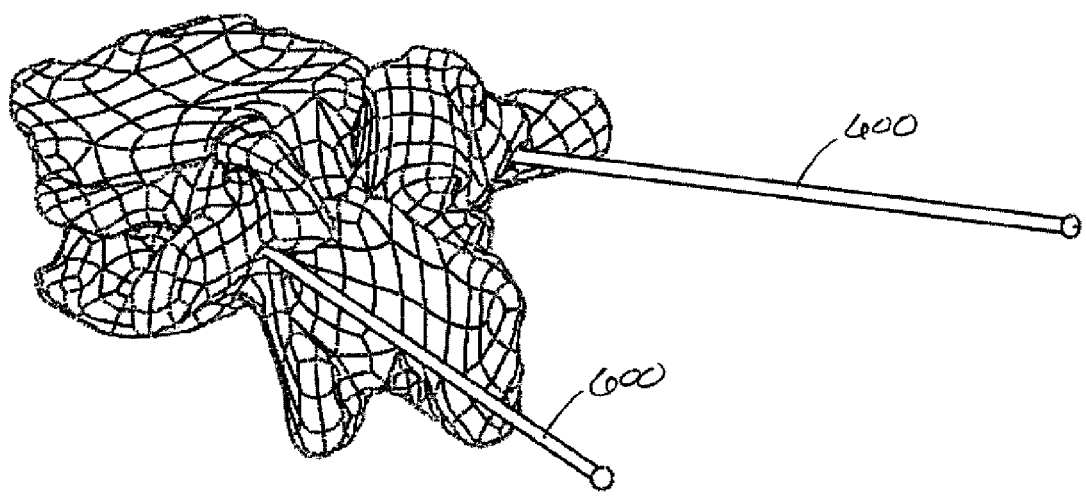

FIGS. 18-19 are perspective views according to yet another alternative embodiment of the present disclosure;

FIGS. 20-21 are perspective views according to yet another alternative embodiment of the present disclosure;

FIG. 22 is a perspective view according to yet another alternative embodiment of the present disclosure;

FIG. 23 is a perspective view according to yet another alternative embodiment of the present disclosure;

FIG. 24 is a perspective view according to yet another alternative embodiment of the present disclosure;

FIG. 25 is a perspective view according to yet another alternative embodiment of the present disclosure;

FIG. 26A is a perspective view according to yet another alternative embodiment of the present disclosure;

FIG. 26B is a perspective view according to the embodiment shown in FIG. 26A;

FIG. 27A is a front elevation view according to yet another alternative embodiment of the present disclosure;

FIG. 27B is a perspective view according to the embodiment shown in FIG. 27A;

FIG. 28 is an elevation view according to yet another alternative embodiment of the present disclosure;

FIG. 29A is a perspective view according to yet another alternative embodiment of the present disclosure;

FIG. 29B is a perspective view according to yet another alternative embodiment of the present disclosure;

FIG. 30 is a perspective view according to yet another alternative embodiment of the present disclosure;

FIG. 31 is a perspective view according to yet another alternative embodiment of the present disclosure;

FIG. 32A is a perspective view according to yet another alternative embodiment of the present disclosure;

FIG. 32B is a perspective view according to the embodiment shown in FIG. 32A;

FIG. 33A is a perspective view according to yet another alternative embodiment of the present disclosure;

FIG. 33B is a perspective view according to the embodiment shown in FIG. 33A;

FIG. 33C is another perspective view according to the embodiment shown in FIG. 33A depicted with the cutting guide of FIG. 32A;

FIG. 34A is a perspective view according to yet another alternative embodiment of the present disclosure;

FIG. 34B is a perspective view according to yet another alternative embodiment of the present disclosure;

FIG. 35 is a top plan view according to yet another alternative embodiment of the present disclosure;

FIG. 36 is a detailed view of the device according to the embodiment shown in FIG. 35;

FIG. 37 is another top plan view of the device according to the embodiment shown in FIG. 35;

FIG. 38 is a top plan view according to yet another alternative embodiment of the present disclosure;

FIG. 39 is another top plan view of the device according to the embodiment shown in FIG. 38;

FIGS. 40A-D are additional top plan views of the devices according to the embodiments shown in FIGS. 35-39;

FIG. 41 includes side elevation views of devices according to another alternative embodiment of the present disclosure;

FIGS. 42A-B are top plan views of a device according to another alternative embodiment of the present disclosure;

FIGS. 43A-B are additional top plan views of a device according to yet another alternative embodiment of the present disclosure;

FIGS. 44A-B are perspective views of the devices shown in FIGS. 43A-B;

FIG. 45 includes side elevation views of drill sleeve devices according to another alternative embodiment of the present disclosure;

FIG. 46 is a front elevation view according to another alternative embodiment of the present disclosure;

FIGS. 47A-D are views of an assembly tray and arrangement device according to another alternative embodiment of the present disclosure;

FIGS. 48A-C are views of a device for providing patient-specific contacting surfaces and trajectories in a patient's cervical spine;

FIGS. 49A-C are views of another device for providing patient-specific contacting surfaces and trajectories in a patient's cervical spine;

FIGS. 50A-D and 51A-C are views of yet another device for providing patient-specific contacting surfaces and trajectories in a patient's cervical spine;

FIGS. 52A-C are views of yet another device for providing patient-specific contacting surfaces and trajectories in a patient's cervical spine;

FIGS. 53A-E are views of an unassembled and assembled device for providing patient-specific contacting surfaces and trajectories in a patient's cervical spine;

FIGS. 54A-C are views of a device for providing patient-specific contacting surfaces and trajectories along with an instrument for positioning the same;

FIGS. 55A-C are views of yet another device for providing patient-specific contacting surfaces and trajectories in a patient's cervical spine;

FIGS. 56A-D are views of yet another device for providing patient-specific contacting surfaces and trajectories in a patient's cervical spine;

FIG. 57 is a side elevation view of a patient-specific insert for use with the devices shown in FIGS. 48A-56D referenced above;

FIGS. 58A-C are views of a modeling device for creating a patient-specific or generic guide with predetermined trajectories;

FIGS. 59A-D are views of yet another embodiment of a guide for use in a patient's cervical spine;

FIGS. 60A-C are additional views of a guide for use in a patient's cervical spine;

FIGS. 61A-C show views of yet another embodiment of a guide for use in a patient's cervical spine;

FIGS. 62A-E show views of yet another embodiment of a guide for use in a patient's cervical spine;

FIGS. 63A-H show various views of additional embodiments of a guide and related apparatus for use in a patient's cervical spine;

FIGS. 64-66 are views of a device having custom inserts for inserting guide wires;

FIG. 67 is the device shown in FIGS. 64-66 with the inserts removed;

FIG. 68 shows FIG. 67 with the device removed but with the wires remaining; and

Figure 74:
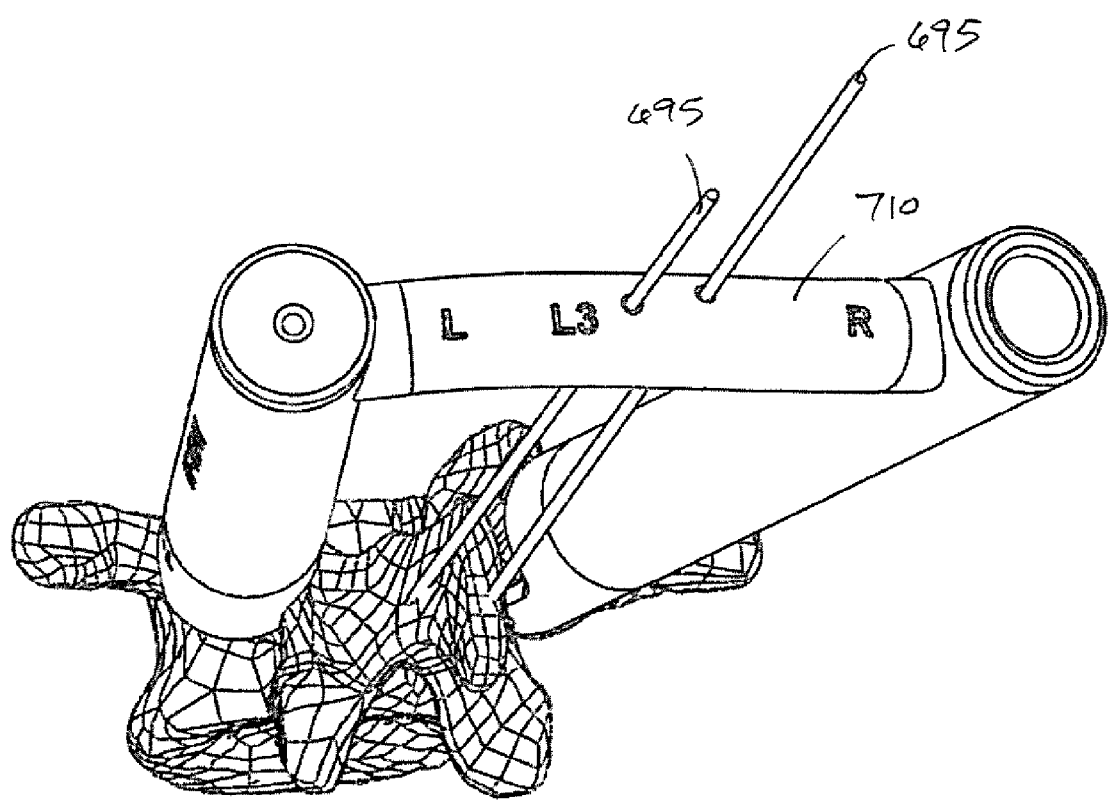
Figure 75:
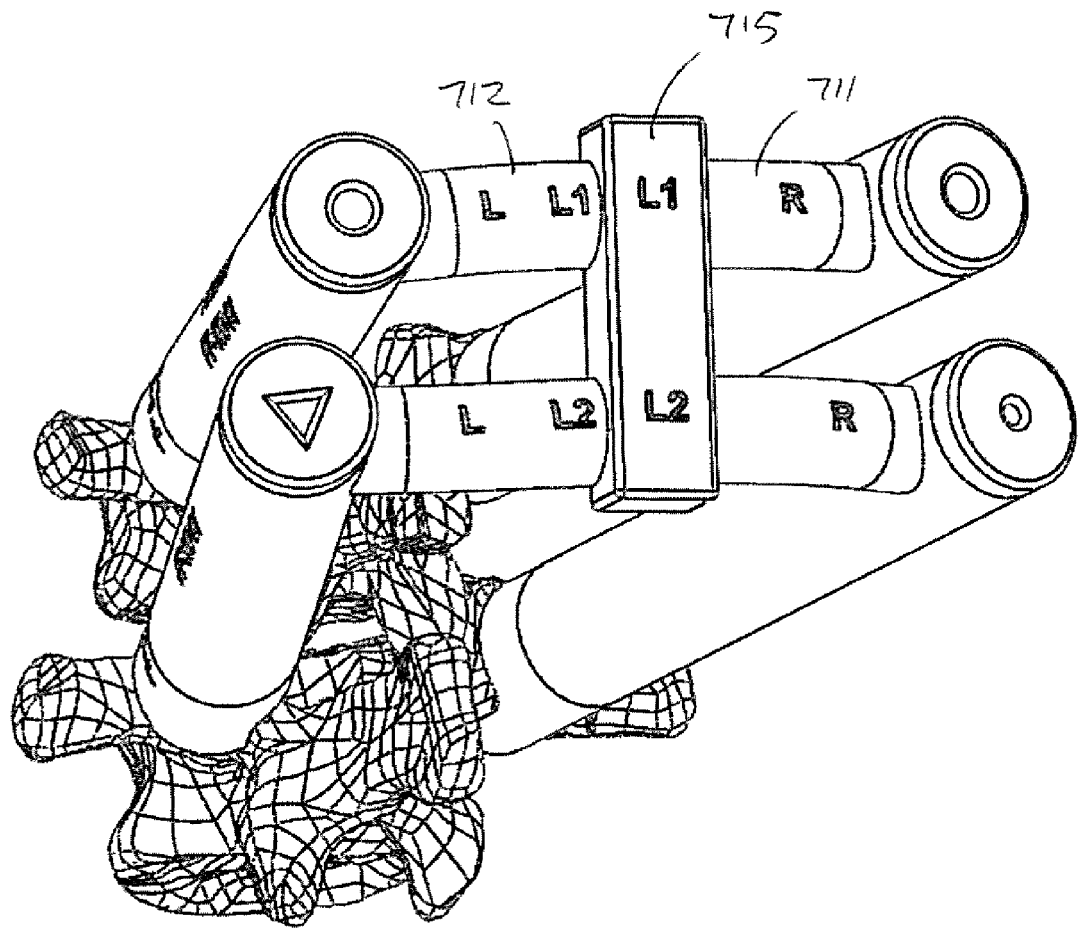
Figure 78A:
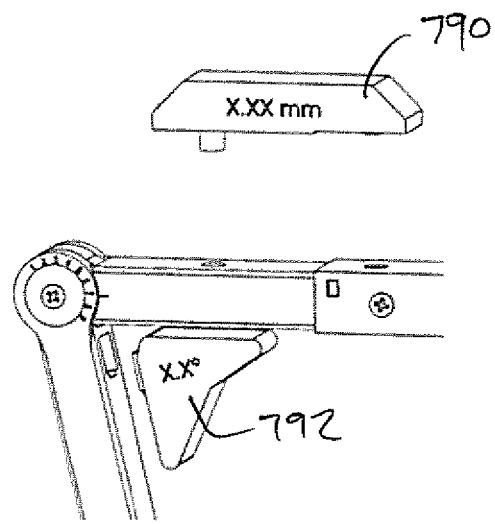
Figure 78B:
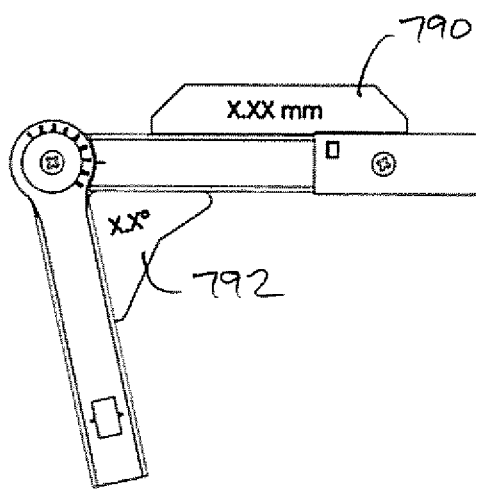
Figure 79A:
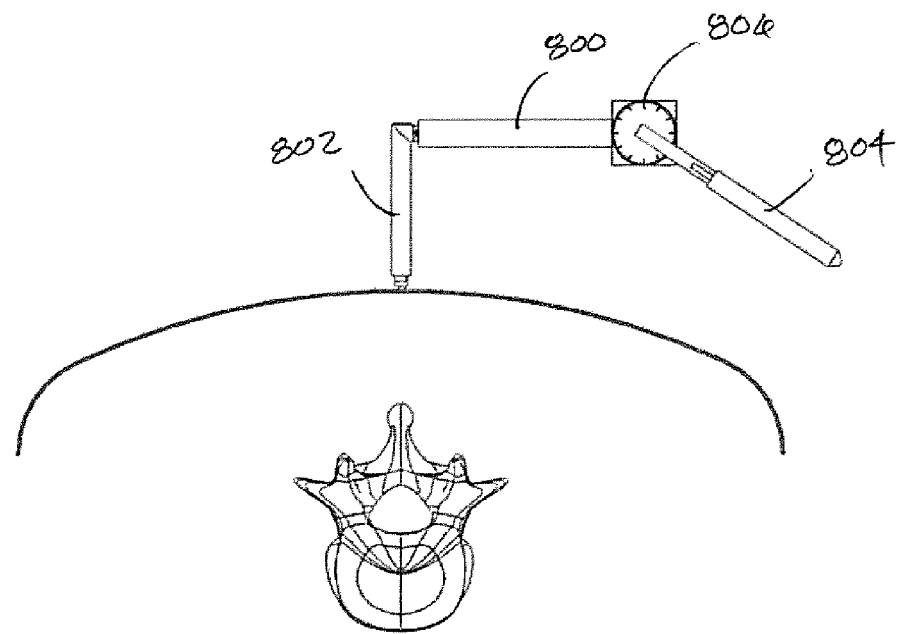
Figure 79B:
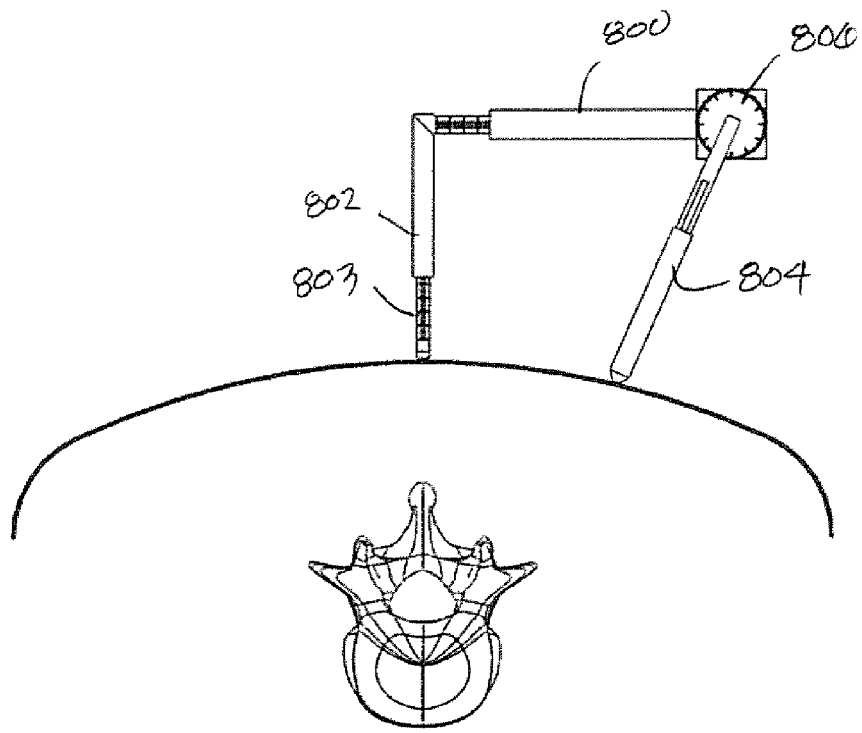
Figure 80:
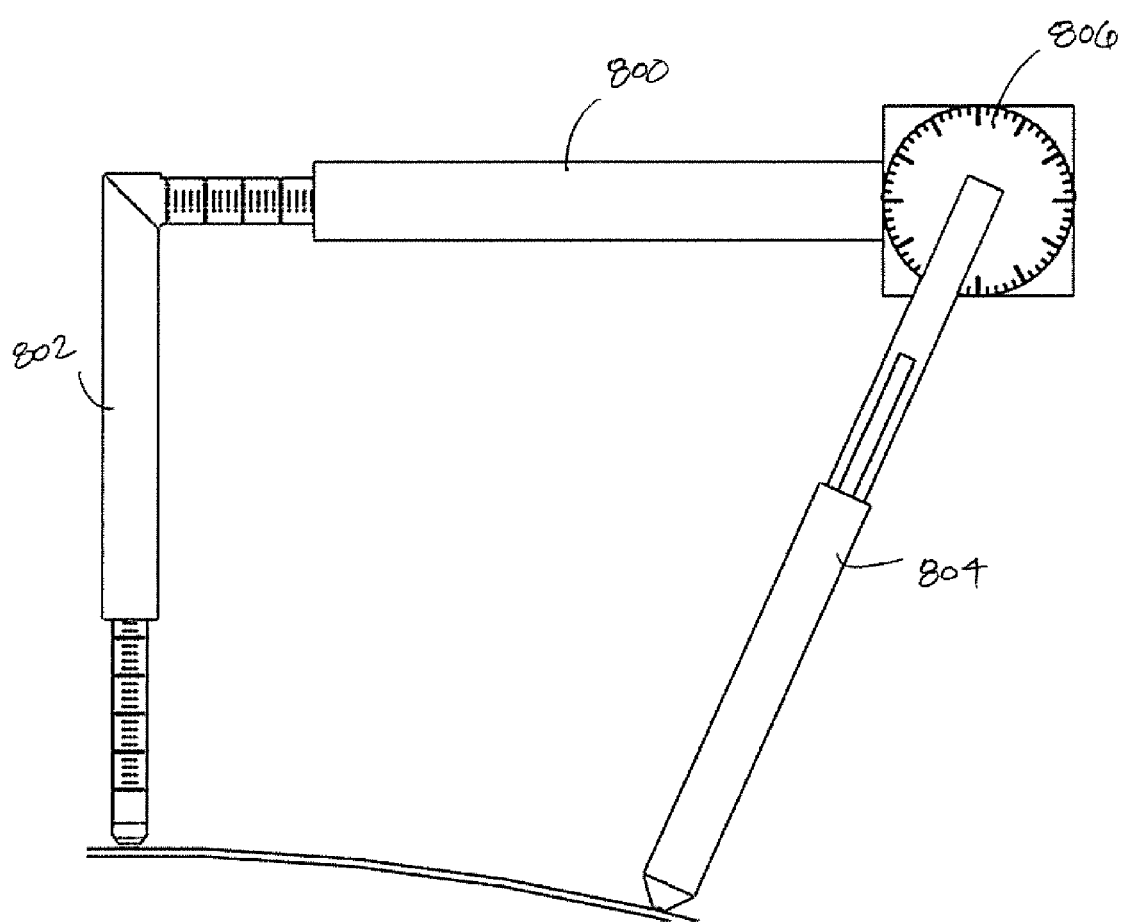
Figure 81A:
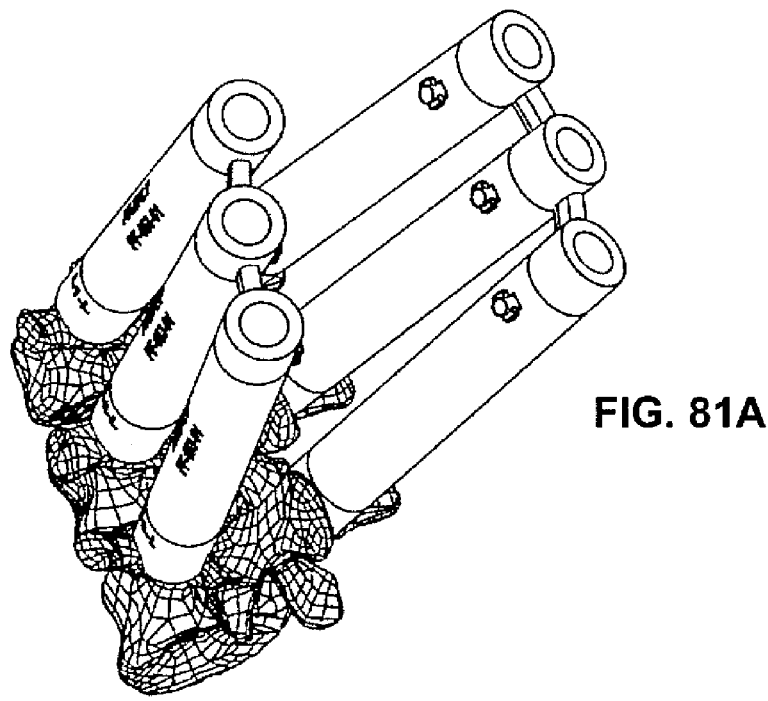
Figure 81B:
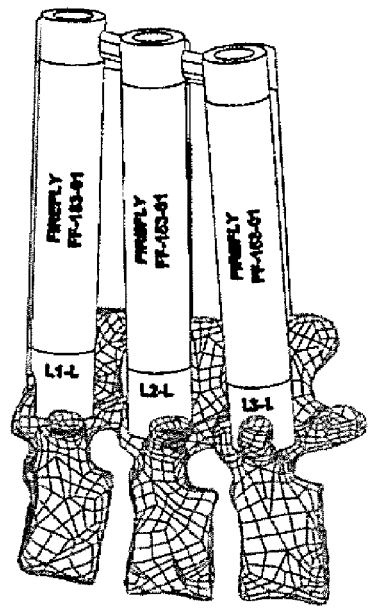
Figure 81C:
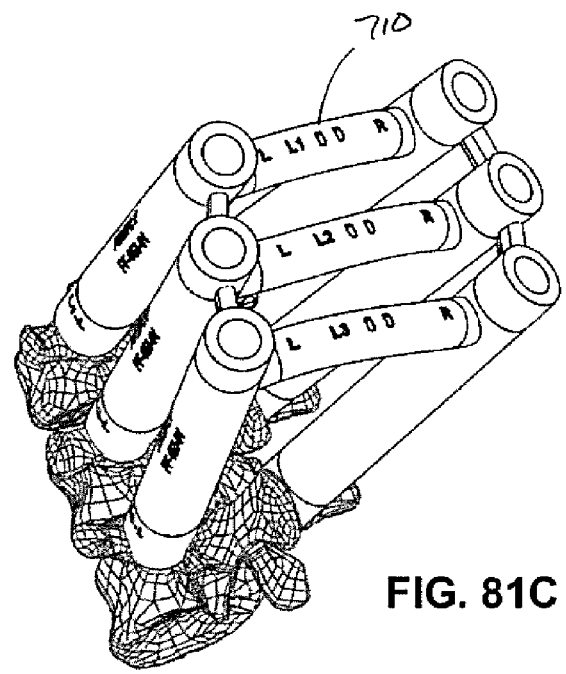
Figure 82A:
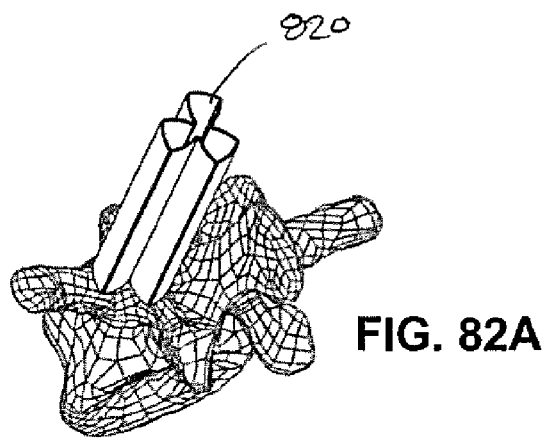
Figure 82B:
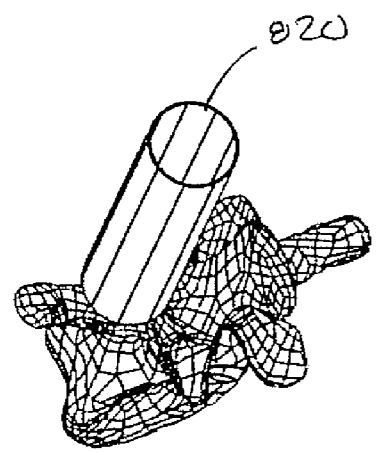
Figure 82C:
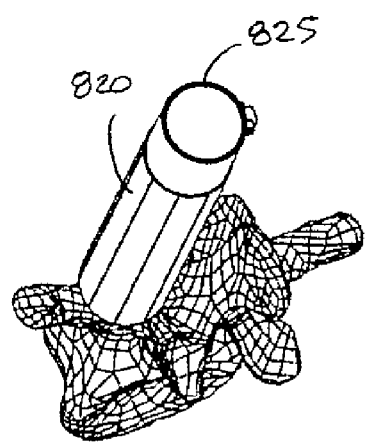
Figure 83A:
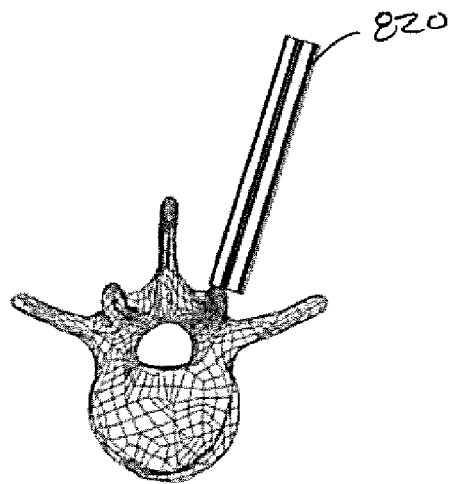
Figure 83B:
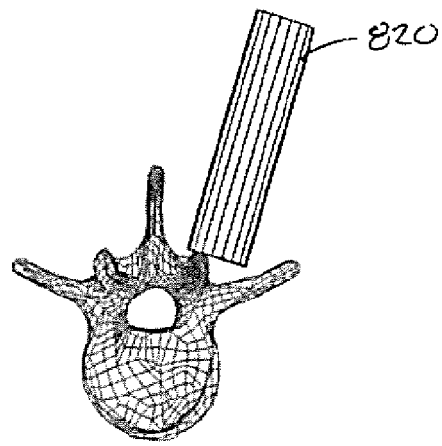
Figure 83C:
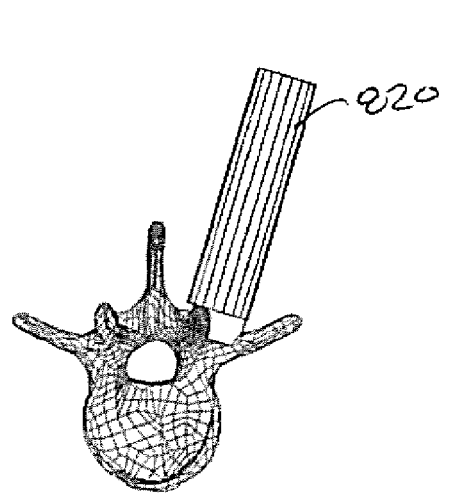
Figure 83D:
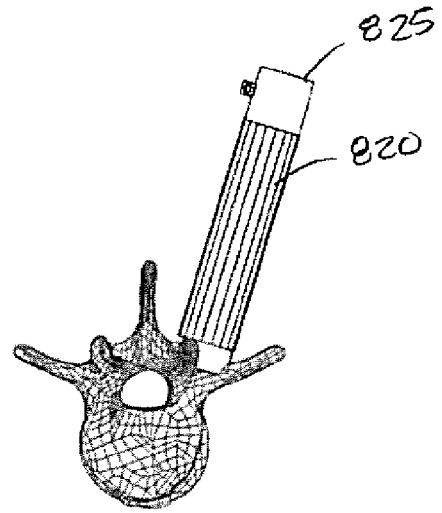
Figure 85:
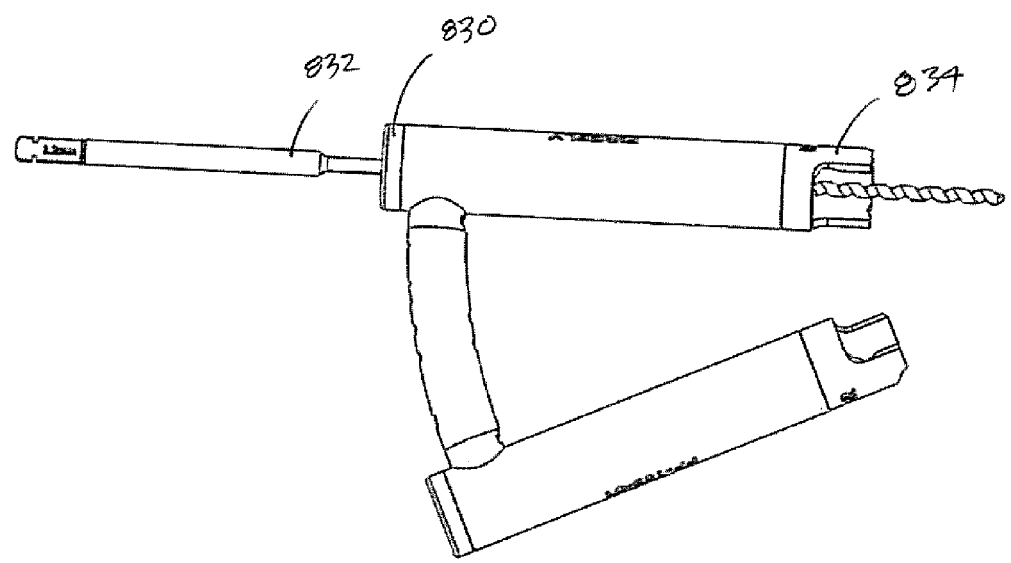
Figure 86A:
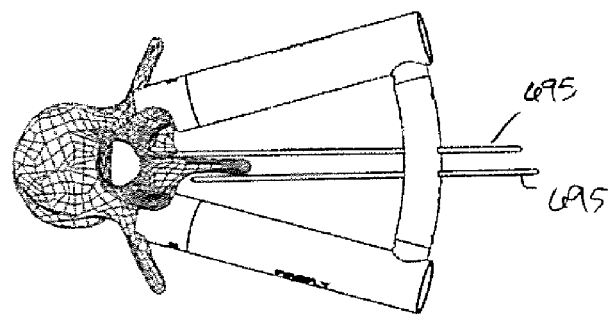
Figure 86B:
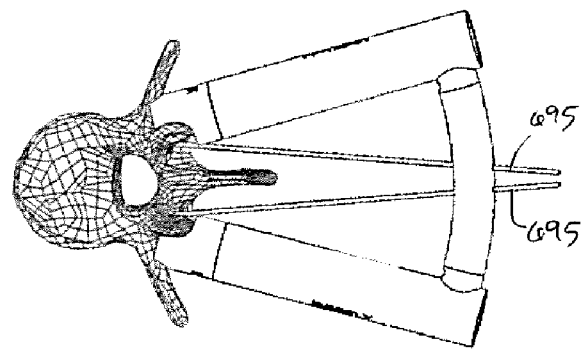
Figure 86C:
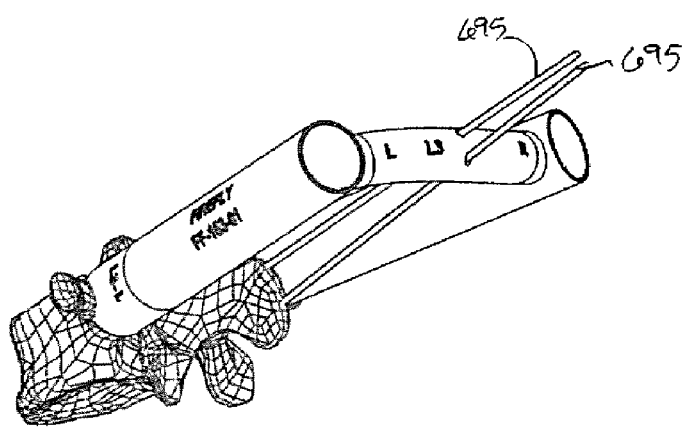
Figure 87A:
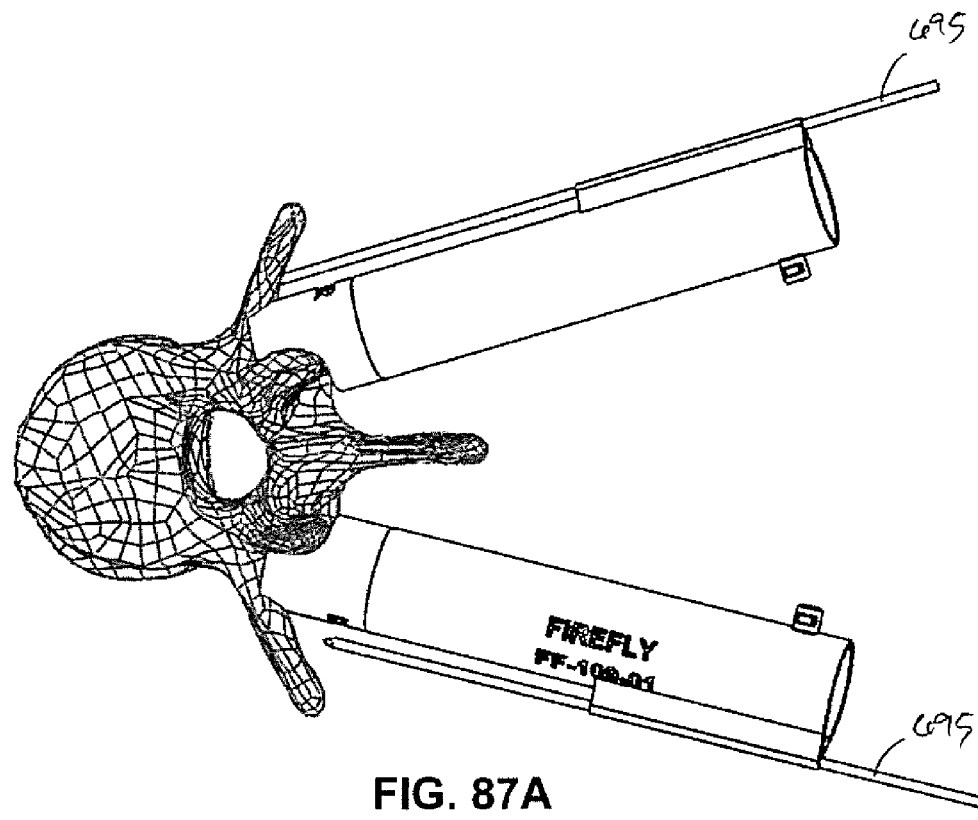
Figure 87B:
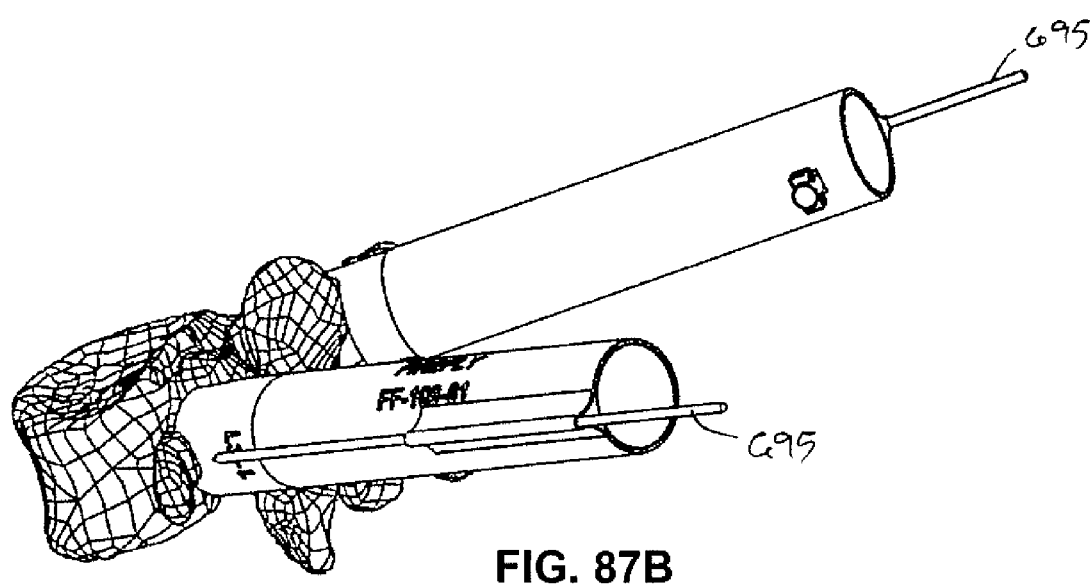
Figure 88A:
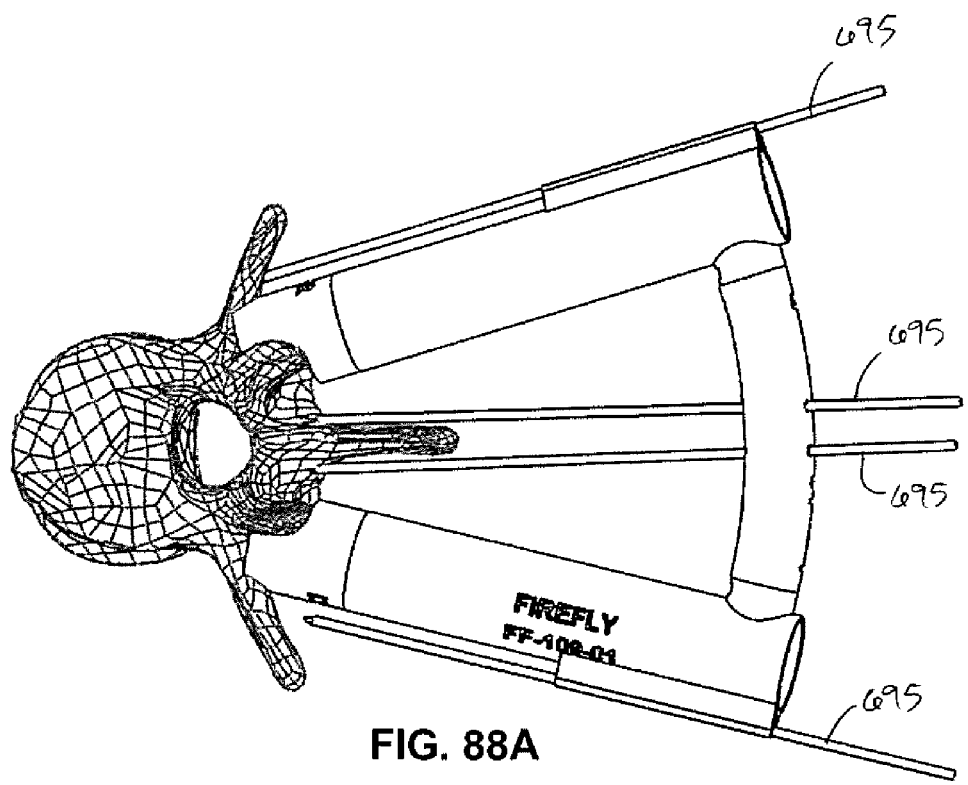
Figure 88B:
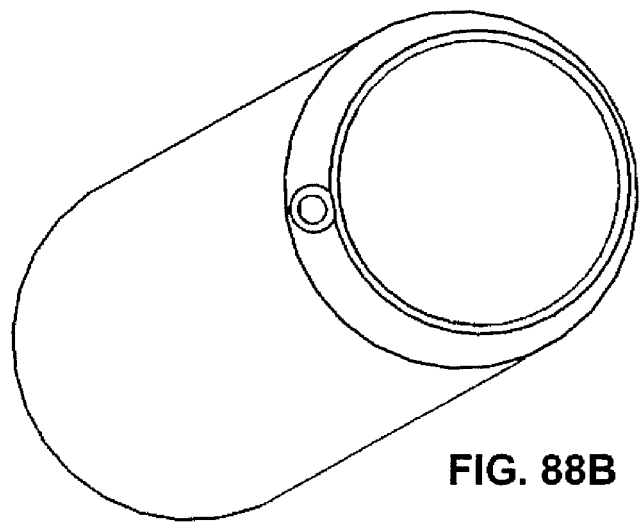
Figure 89A:
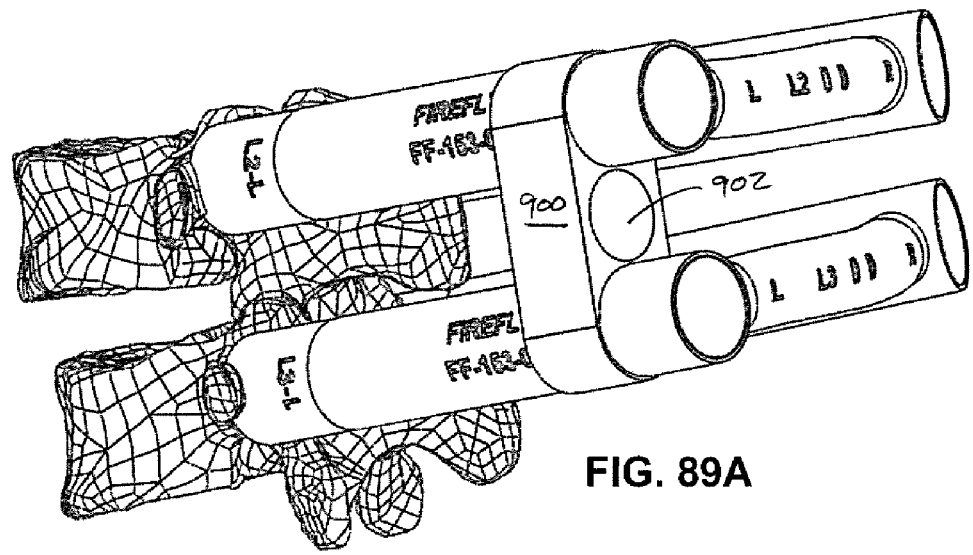
Figure 89B:
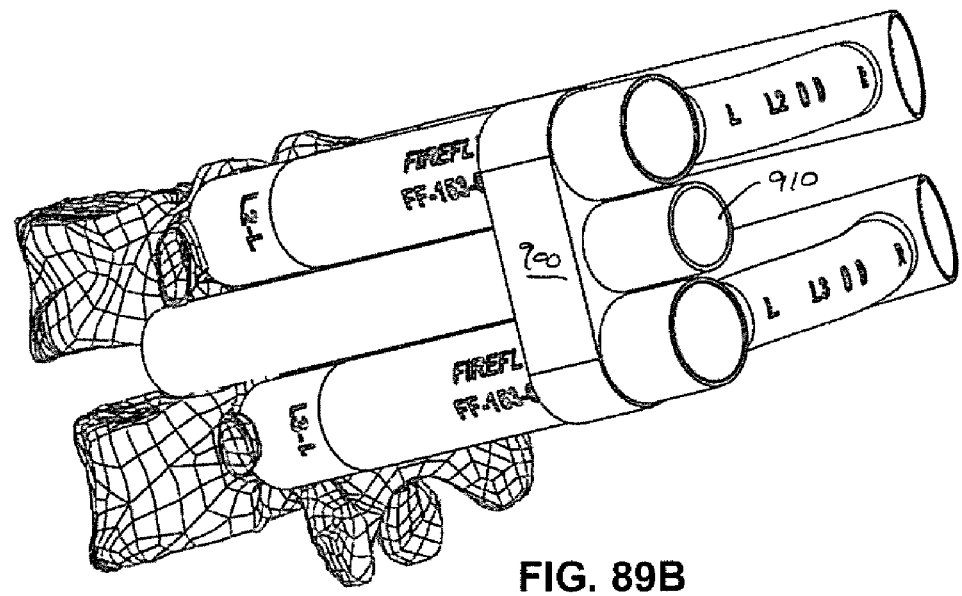
Figure 90A:
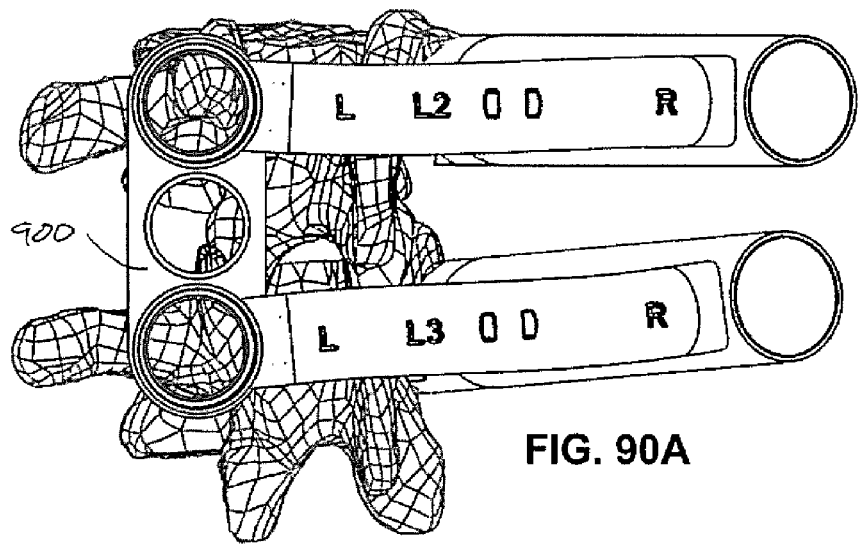
Figure 90B:
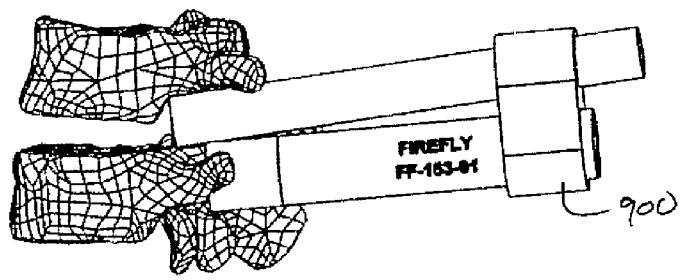
Figure 90C:
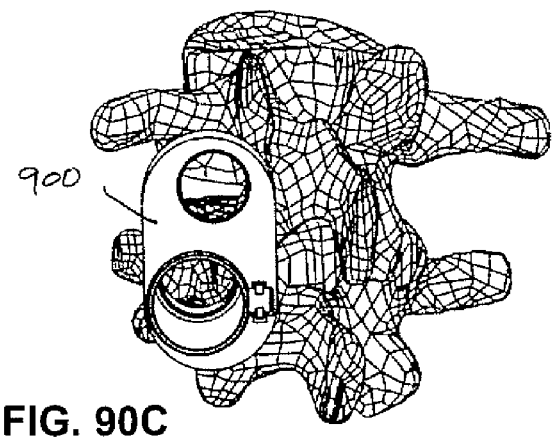
Figure 92A:
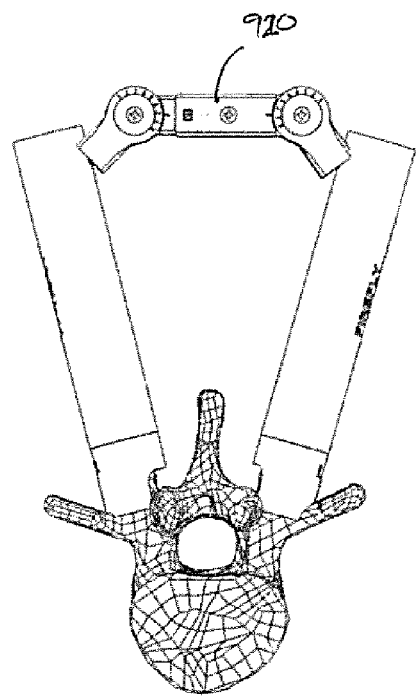
Figure 92B:
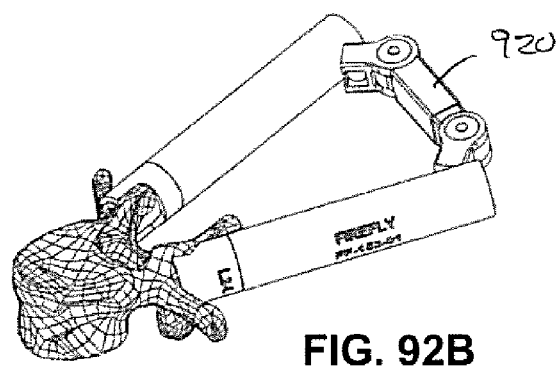
Figure 92C:
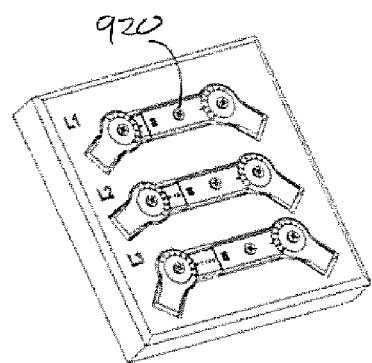
Figure 92D:
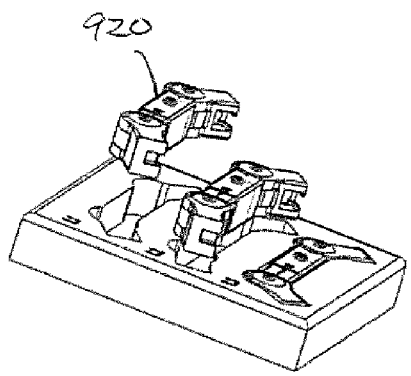
Figure 94A:
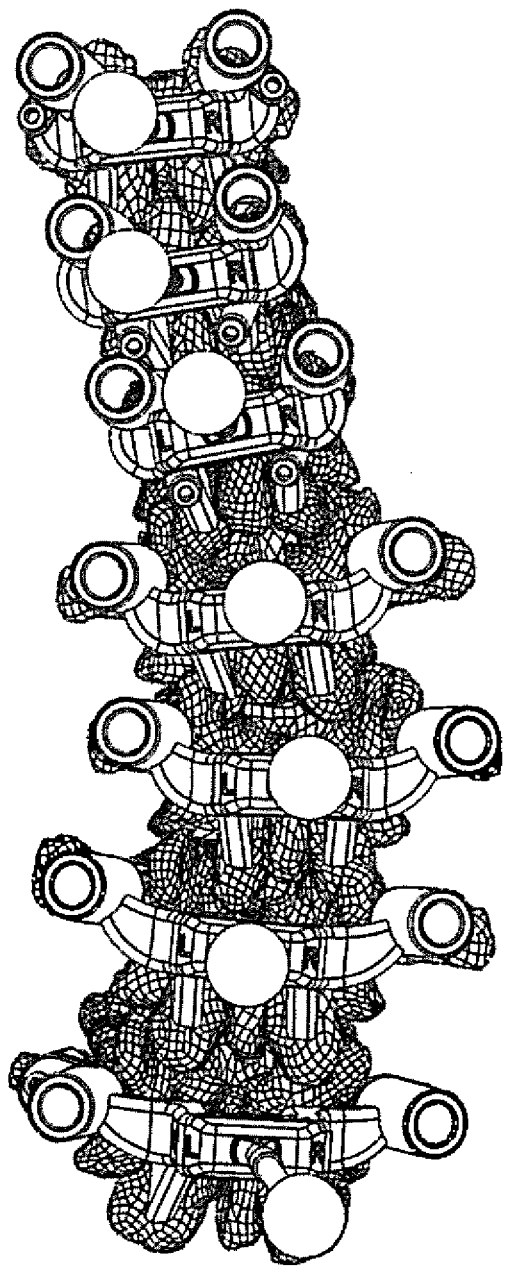
Figure 94B:
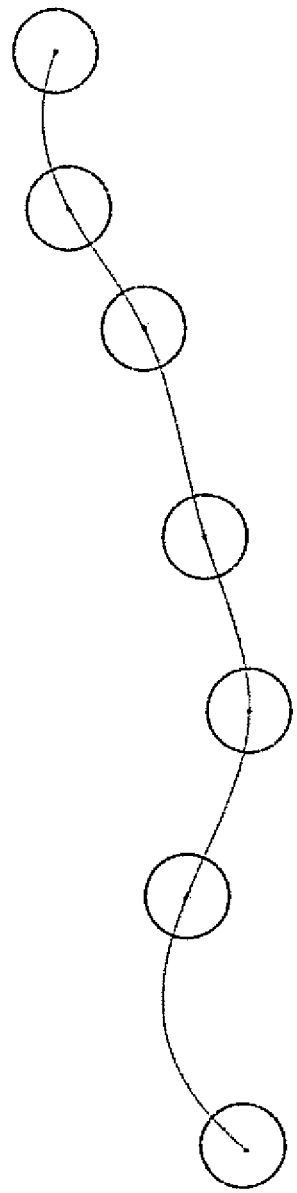
Figure 94C:
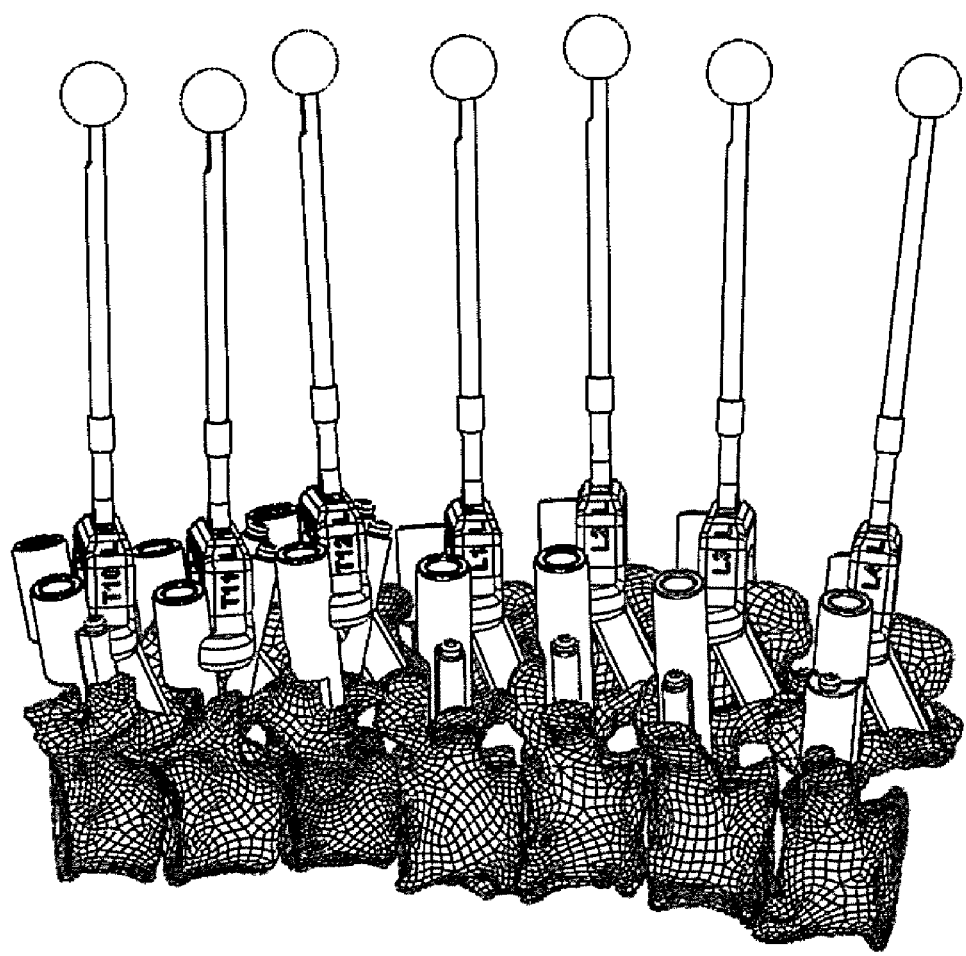
Figure 95A:
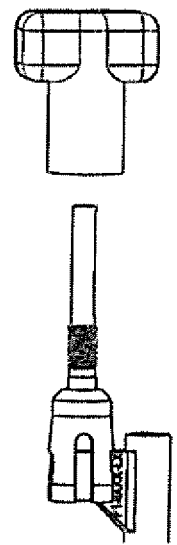
Figure 95B:
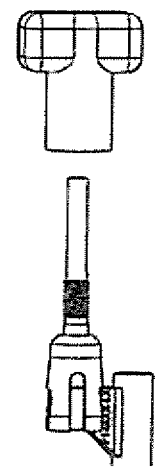
Figure 95C:
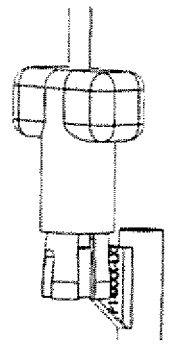
Figure 96A:
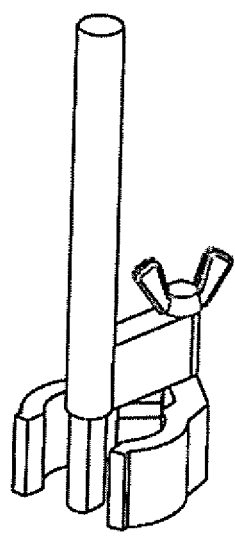
Figure 96B:
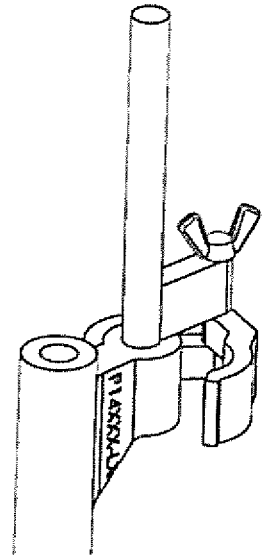
Figure 96C:
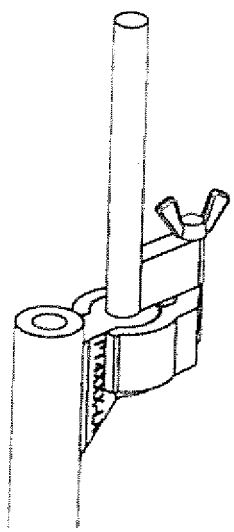
Figure 97A:
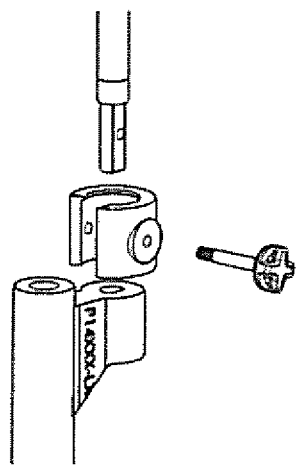
Figure 97B:
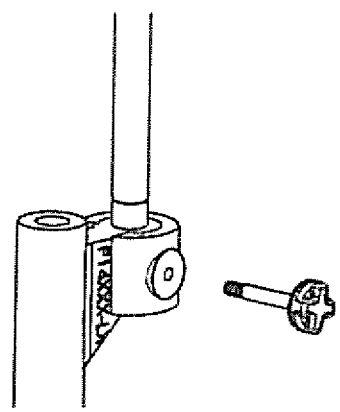
Figure 97C:
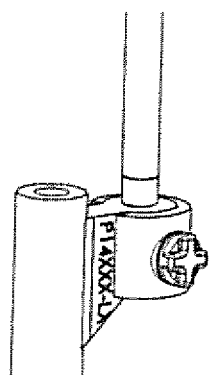

FIGS. 69-73 are various views of a device according to yet another alternate embodiment of the present disclosure for use in a MIS procedure;

FIG. 74 is a perspective view of the device shown in FIGS. 69-73 further comprising one or more optional alignment/depth/position control elements;

FIG. 75 is an alternate embodiment of the device shown in FIGS. 69-73;

FIGS. 76A-C are views of an alternative embodiment of a device further comprising one or more optional alignment/depth/position control elements;

FIGS. 77A-G are views of another alternative embodiment of a device further comprising one or more optional alignment/depth/position control elements;

FIGS. 78A-B are views of another alternative embodiment of a device further comprising one or more optional alignment/depth/position control elements;

FIGS. 79A-B are views of another alternative embodiment of a device further comprising one or more optional alignment/depth/position control elements;

FIG. 80 is a detailed view of the device of FIGS. 79A-B;

FIGS. 81A-C are various views of a MIS device according to another embodiment;

FIGS. 82A-C are various views of a MIS device according to yet another embodiment;

FIGS. 83A-D are various views of a MIS device according to yet another embodiment;

FIGS. 84A-C are various views of a MIS device according to yet another embodiment;

FIG. 85 is a view of another MIS device according to an alternate embodiment;

FIGS. 86A-C are various views of a MIS device according to yet another embodiment;

FIGS. 87A-B are various views of a MIS device according to yet another embodiment;

FIGS. 88A-B are various views of a MIS device according to yet another embodiment;

FIGS. 89A-B are various views of a MIS device according to yet another embodiment;

FIGS. 90A-C are various views of a MIS device according to yet another embodiment;

FIGS. 91A-D are various views of a MIS device according to yet another embodiment;

FIGS. 92A-D are various views of a MIS device according to yet another embodiment;

FIGS. 93A-D are various views of templates which may be contoured using methods described herein for create a patient-specific device;

FIGS. 94A-C are various views of one embodiment of the present disclosure, which includes a plurality of patient-specific guides;

FIGS. 95A-C are side elevation views of a connection mechanism according to one embodiment of the present disclosure;

FIGS. 96A-C are side perspective views of a connection mechanism according to another embodiment of the present disclosure;

FIGS. 97A-C are side perspective views of a connection mechanism according to yet another embodiment of the present disclosure;

FIGS. 98A-C are side perspective views of an insert and guide sleeve according to one embodiment of the present disclosure;

FIGS. 99A-G show various views of a system for aligning a guide according to one of the various embodiments described herein;

FIGS. 100A-D are side perspective views of an insert according to one embodiment of the present disclosure; and FIGS. 101A-D are various views of a patient-specific guide according to yet another alternative embodiment of the present disclosure.

DETAILED DESCRIPTION

As shown in the appended Figures and described in further detail herein, the present disclosure relates to a novel system and method for developing a variety of customized, patient-matched apparatus for use in a diverse number of surgical procedures. The system and method uses a patient's unique morphology, which may be derived from capturing MRI data or CT data to derive one or more patient-matched apparatus, which comprise complementary surfaces to those encountered during the surgical procedure(s) as derived from a set of data points. According to various embodiments described herein, the patient-matched apparatus may further comprise desired axes and/or insertional trajectories. According to one alternate embodiment described herein, the patient-matched apparatus may be further matched with at least other apparatus used during the surgical procedure. Other features of the disclosure will become apparent after a review of the following disclosures and varying embodiments of the invention.

Figure 1:
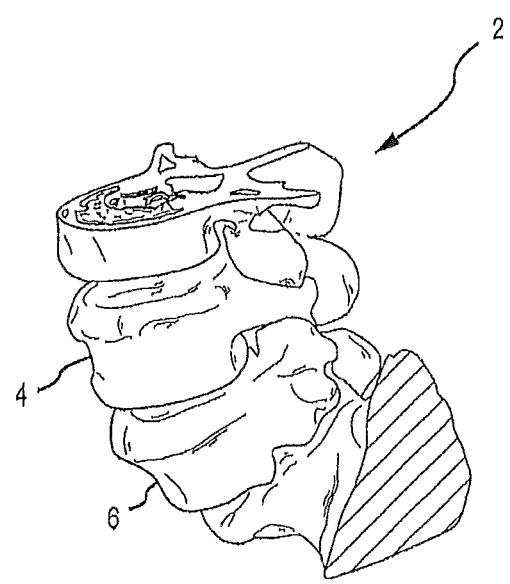

Multiple embodiments of the disclosure are depicted in FIGS. 1-101. Referring now to FIG. 1, a perspective view of a three-dimensional model of a unique grouping of anatomical features according to one embodiment of the present disclosure is shown. Here, the model 2 is comprised of multiple vertebral bodies 4, 6 but according to other embodiments may be comprised of any anatomical grouping for a particular patient. Data associated with the model 2 may be captured from a MRI or CT scan or from radiographic images of the patient's corresponding boney anatomy (or alternatively from other data sources). The data, once captured, may be converted using known software tools to a CAD program, where the data set is representative of the model 2 and may be used to provide additional data points for forming the contours, sizes, shapes and orientations of one or more apparatus to be used in the surgical procedure.

According to an alternative embodiment, the data may be obtained from an ultrasonic or nuclear medicine scanning device. In yet another alternative embodiment, the data may be supplemented or merged with data from a bone density scanner to fabricate a device that is designed to remain in the patient after the surgical procedure is completed, or alternatively to achieve further control over the orientation of any desired axes, particularly where the surgical procedure involves insertion of one or more implantable devices.

Figure 2:
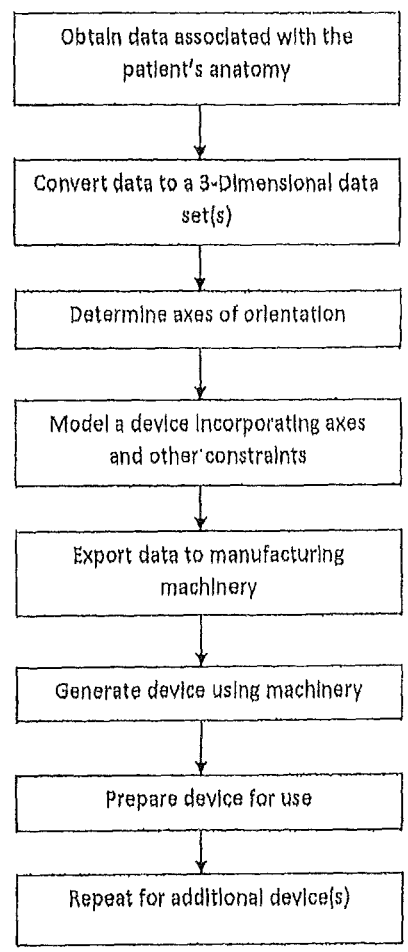

FIG. 2 is a flow chart showing the various steps of performing a method of manufacturing an apparatus, according to various embodiments described herein, for use in facilitating a surgical procedure. The method, according to a preferred embodiment, comprises the following steps:

A) Obtaining data associated with the patient's anatomy by way of a MRI or CT scan;

B) Converting the MRI or CT scan data to a 3-Dimensional data set(s)

C) Determining one or more axes of orientation of a device to be constructed for use in facilitating the surgical procedure(s) to be performed on the patient;

D) Modeling the device for use in facilitating the surgical procedure(s) using the determined axes and accounting for any other constraints derived from the converted data set(s);

E) Generating a prototype of the modeled device by, for example, use of rapid prototyping machinery; and F) Preparing the prototype for use during the surgical procedure(s).

As shown in FIG. 2, the method may comprise additional steps or may be repeated for additional devices used in the surgical procedure. The step of obtaining data is typically performed in a traditional manner, by subjecting the patient to a scan using MRI or CT or other suitable scanning equipment known in the art. The data is then captured by the equipment and may be converted to a 3-Dimensional data set(s) by software or other algorithmic means known in the art, such as by exporting the data into a known modeling software program that allows data to be represented, for example, in CAD format. Once this data is converted, a device may be modeled to complement the data set(s) and oriented by one or more axes determined by the surgeon either before or through observation of the data set(s) from the initial scan of the patient's anatomy.

The method step of accounting for any other constraints derived from the converted data set(s) may comprise adjusting the size of the modeled device to accommodate the space limitations on the surgeon, orienting elements of the modeled device to avoid certain anatomical features, creating one or more surfaces that may conveniently be operatively associated with one or more instruments and/or tools used in the surgical procedure(s), etc. The prototype may be generated using known rapid prototyping machinery, or alternatively by milling machinery such as a CNC milling machine. Alternatively, the initial device fabricated by this method may be in a temporary state for further consideration and or manipulation by the surgeon, and then finally constructed using one of the methodologies described herein. The steps may be repeated for complementary devices, some or all of which may include further matching surfaces for the patient's anatomy or to the previously fabricated devices (i.e., the devices fabricated may have matching surfaces for adjoining together one or more devices, as described in greater detail below).

Alternatively, the system and method described herein may facilitate the alignment of various anatomical features for a particular patient, such as, for example, multiple vertebral bodies in a patient to correct spinal deformities. For example, the data set(s) may provide an initial location for the anatomical features, but may be further manipulated by the surgeon in a pre-operative setting to create a desired data set(s), such as a final location for the anatomical features once the surgical procedure(s) are completed. In this manner, the devices formed by the system and method described above may be used in either an initial location or a final location for the anatomical features, and be matched to those specific locations and orientations for each stage of the surgical procedure. These staged devices would in turn provide the surgeon with a visual guide to determine the degree of correction achieved through the surgical procedure, as compared to the pre-operative plan. Other variations on the method of the present disclosure are described in the Summary of the Invention and included in the appended claims.

Fabrication methods may comprise the use of a rapid prototyping machine, such as a stereolithography (STL) machine, selective laser sintering (SLS) machine, or a fused deposition modeling (FDM) machine, direct metal laser sintering (DMLS), electron beam melting (EBM) machine, or other additive manufacturing machine. One example of such a rapid prototyping machine is commercially available from 3D Systems and known as Model SLA-250/50. The rapid prototyping machine selectively hardens a liquid, powdered or other non-hardened resin or metal into a three-dimensional structure, which can be separated from the remaining non-hardened resin, washed/sterilized and used directly as the apparatus. The prototyping machine receives the individual digital data sets and produces one structure corresponding to each of the desired apparatus.

Generally, because stereolithographic machinery produces a resin, which may have less than optimal mechanical properties (which may not be generally acceptable for a particular surgical use), the prototyping machine may alternatively be used to produce a mold. After the model is prepared, a conventional pressure or vacuum molding machine may be used to produce the apparatus from a more suitable material, such as stainless steel, titanium alloy, aluminum alloy, chromium alloy, PEEK, carbon fiber, or other metals or metal alloys.

According to another alternative embodiment, the system and method may comprise providing the data set(s) to a CNC machine, which in turn may be utilized to manufacture a custom milled apparatus from one of the more mechanically sound materials listed above. In yet another alternative embodiment, volume manufacturing of apparatus in accordance with the embodiments described herein may also be achieved, for example, where a particular orientation or insertion trajectory is common among a large grouping of patients.

According to one particular embodiment of the present disclosure, a system and method is provided for fabricating apparatus for use with a variety of surgical procedures associated with a patient's spine. Individuals who suffer degenerative disc disease, natural spine deformations, a herniated disc, spine injuries or other spine disorders often require surgery on the affected region to relieve the individual from pain and prevent further injury. Such spinal surgeries may involve removal of damaged joint tissue, insertion of a tissue implant and/or fixation of two or more adjacent vertebral bodies, with the surgical procedure varying depending on the nature and extent of the injury.

For patients with varying degrees of degenerative disc disease and/or nerve compression with associated lower back pain, spinal fusion surgery, or lumbar arthrodesis ("fusion") is commonly used to treat the degenerative disease. Fusion commonly involves distracting and/or decompressing one or more intervertebral spaces, followed by removing any associated facet joints or discs, and then joining or "fusing" two or more adjacent vertebra together. Fusion of vertebral bodies also commonly involves fixation of two or more adjacent vertebrae, which may be accomplished through introduction of rods or plates, and screws or other devices into a vertebral joint to join various portions of a vertebra to a corresponding portion on an adjacent vertebra.

Fusion may occur in the lumbar, thoracic or cervical spine region of a patient. Fusion requires tools for accessing the vertebrae and implanting the desired implant, any bioactive material, etc. Such procedures often require introduction of additional tools and/or instruments, including drills, drill guides, debridement tools, irrigation devices, vises, clamps, cannulae, retractors, distracters, cutting tools, cutting guides and other insertion/retraction tools and instruments. The insertion, alignment and placement of these tools, instruments and fixation devices are critical to the success of the operation. As such, providing a customized and patient-specific tool or instrument increases the likelihood that the surgical procedure will be successful.

Figure 3:
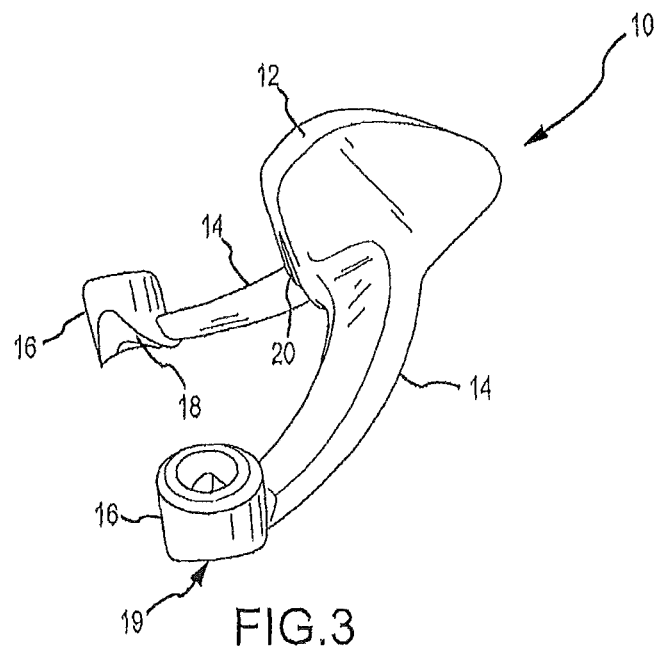
Figure 4:
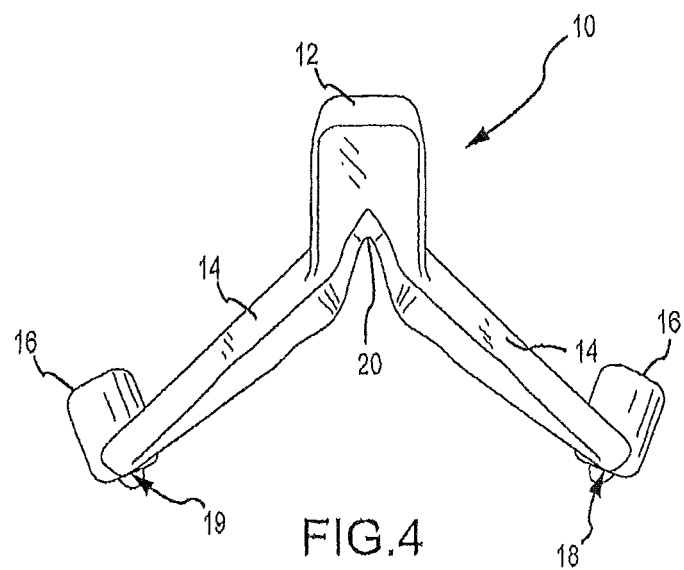

For example, one particular apparatus formed by the system and method described above and that may be used for a particular fixation related surgery is depicted in FIGS. 3 and 4. According to one embodiment of the present disclosure, the apparatus may be in the form of a pedicle screw guide 10, which is comprised of a medial body 12 and two generally elongated wings 14, each wing 14 terminating in a generally cylindrical column 16. In a preferred embodiment each of the cylindrical columns 16 is substantially hollow to permit one or more types of devices to be inserted therethrough, as depicted in FIG. 3. The medial body 12 further comprises a longitudinal cavity 20 formed about a lower surface of the medial body 12 (shown from the perspective view taken in FIG. 3). Each of the cylindrical columns 16 further comprise a lower, patient-contacting surface 18, 19, which in conjunction with the longitudinal cavity 20 provide a plurality of patient-specific contours for matching with a plurality of anatomical features, as described in greater detail below.

The contours and locations of the lower, patient-contacting surfaces 18, 19 and the longitudinal cavity 20 are formed by use of data set(s) converted from a MRI or CT scan of the patient. The remainder of the pedicle screw guide 10 shown in FIGS. 3 and 4 may be formed to meet the surgeon's particular preferences. For example, the wings 14 need only be of sufficiently length to locate the two cylindrical columns 16 in the location of the corresponding patient-matched anatomical features. The wings may take on other shapes, orientations, thicknesses, etc. without deviating from the novel aspects of this disclosure. Similarly, the medial body 12 need only be sized to accommodate the longitudinal cavity 20, and may comprise other extensions other than the wings 14 to aid in grasping or manipulating the pedicle screw guide 10 as desired.

Additionally, the wings 14 may be made from a semi-malleable or semi-rigid material to create at least a partial interference fit when the pedicle screw guide 10 is placed on the corresponding anatomical grouping for the particular surgery. For example, a snap or interference fit may be formed by subtle deflection of the wings 14 when placing the two cylindrical columns 16 adjacent the inferior articular process, and then deflect to the desired location once the wings are positioned in their final orientation. Further aspects of the disclosure in this respect are described in greater detail below.

Figure 5:
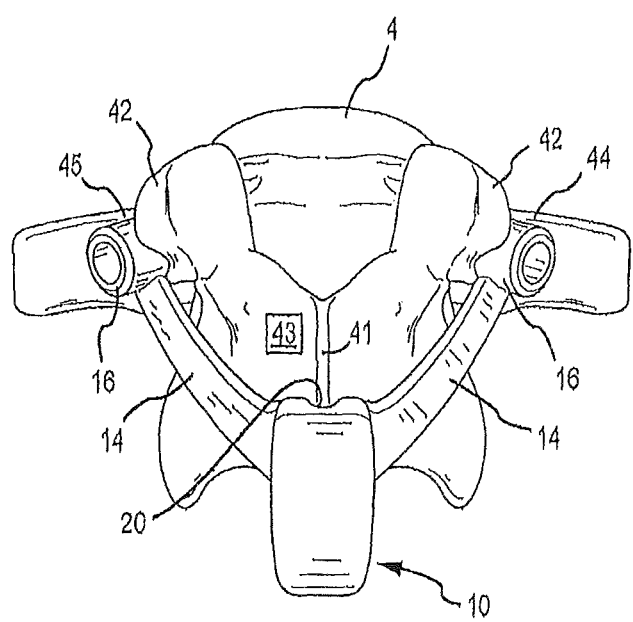

FIG. 5 is a plan view of the apparatus shown in FIG. 3 relative to a unique grouping of anatomical features according to one embodiment of the present disclosure. Here, the pedicle screw guide 10 is positioned so that the medial body 12 is centrally located above the central portion of a vertebral body 4, such that the longitudinal cavity 20 mates with the contours of the spinous process 41 for this particular vertebral body 4. Similarly, the cylindrical columns 16 are positioned one at each medial side of the pedicle screw guide 10 so that the wings 14 span the lamina 43 of the vertebral body 4 and the cylindrical columns 16 are located proximate to the inferior articular process 44, 45. The lower, patient-contacting surface 18, 19 of cylindrical columns 16 are formed to mate with the contours of the inferior articular process 44, 45 and behind the superior articular process 42.

Thus, the pedicle screw guide 10 provides a plurality of mating or matching locations, any one of which, if not positioned correctly, will impact the seating of the other two. In this aspect the pedicle screw guide provides a notable improvement over the prior art, which may be slightly rotated, misaligned or misplaced and still appear to the surgeon as if the device is properly seated. The redundancy and plurality of mating surfaces ensures that the pedicle screw guide 10 is both properly located and properly aligned. If the pedicle screw guide 10 is not properly located or aligned, the lower, patient-contacting surfaces 18, 19 will not fit on each of the inferior articular processes 44, 45 and thereby prevent the longitudinal cavity 20 from being firmly seated on the spinous process 41.

Figure 6:
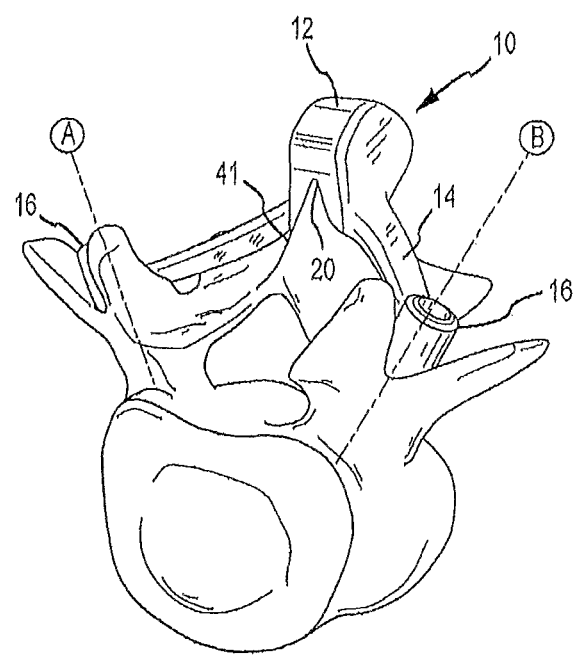

FIG. 6 is a perspective view of the apparatus shown in FIG. 5. Desired insertion trajectory lines A, B are shown to demonstrate that the locating of the cylindrical columns 16 is in addition to the orientation of the axes for each of the cylindrical columns 16, which may be independent relative to their seating adjacent the inferior articular process 44, 45 (i.e., the direction of the axis relative to normal may be different among the cylindrical columns 16). The orientation of the cylindrical columns 16 is also derived from the data set(s) described above, and in one preferred embodiment is selected based on the orientation that will permit a fixation device (i.e., pedicle screw) to be inserted consistent with the location of the pedicle and in a direction that avoids penetration of the fixation device from the pedicle (i.e., eliminates the possibility of the screw either extending through the pedicle or becoming inserted at an angle that causes the pedicle screw to exit the side of the pedicle).

Figure 7:
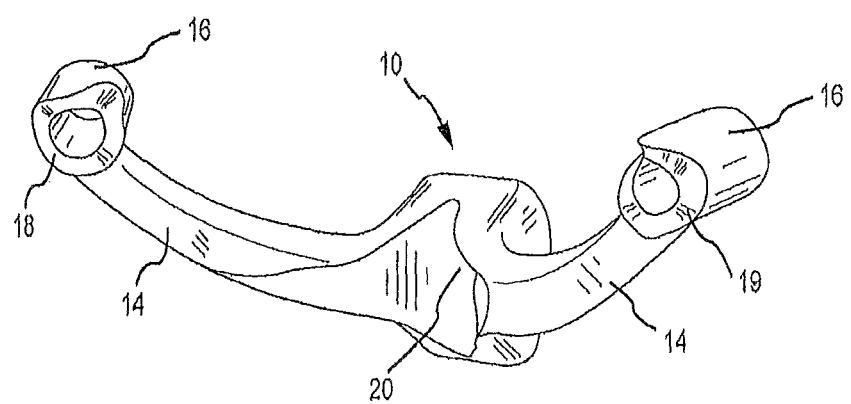

The customized or configured patient-contacting surfaces of the apparatus shown in FIGS. 3-6 are demonstrated by the bottom perspective view of the pedicle screw guide 10 in FIG. 7. Here, the lower, patient-contacting surfaces 18, 19 may comprise dynamic contours having multiple compound radii, such that the surfaces 18, 19 are completely congruent with the corresponding anatomical features of the vertebrae. Thus, the surfaces conform substantially to the surface of the vertebrae where the cylindrical columns 16 are to be located during the surgical procedure, and would not conform substantially to a different surface of the vertebrae. In this manner, the surgeon is informed immediately if the pedicle screw guide 10 is misaligned, because it will not properly seat on the vertebrae.

Figure 8:
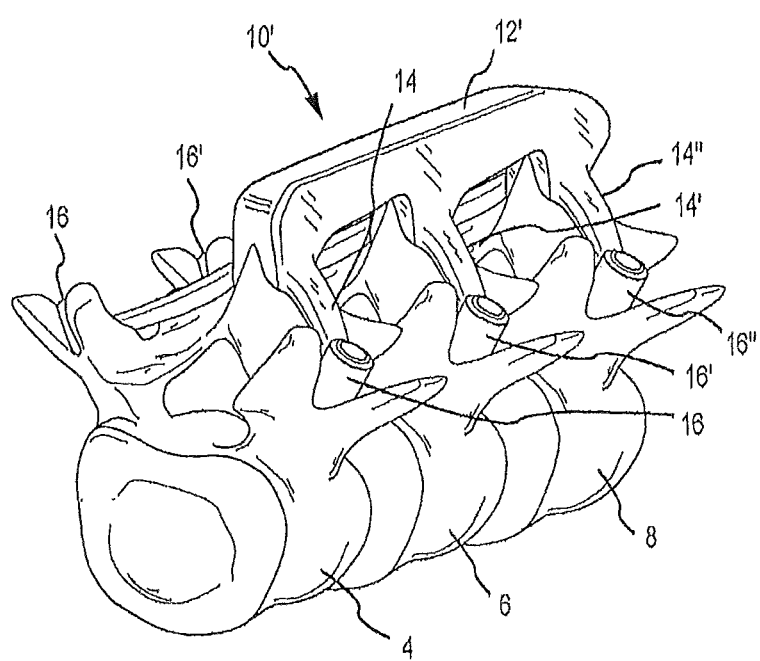

FIG. 8 shows an apparatus according to an alternative embodiment of the present disclosure. In this embodiment, a multi-level pedicle screw guide 10' is shown relative to several adjoining vertebral bodies 4, 6, 8. The multi-level pedicle screw guide 10' comprises multiple secondary wings 14' and tertiary wings 14", which each have corresponding cylindrical columns 16', 16" for inserting and aligning a plurality of pedicle screws into the adjoining vertebral sections 6, 8. It is expressly understood that multiple levels in number greater than or less than three may be achieved without departing from the spirit of the present invention.

Figure 9:
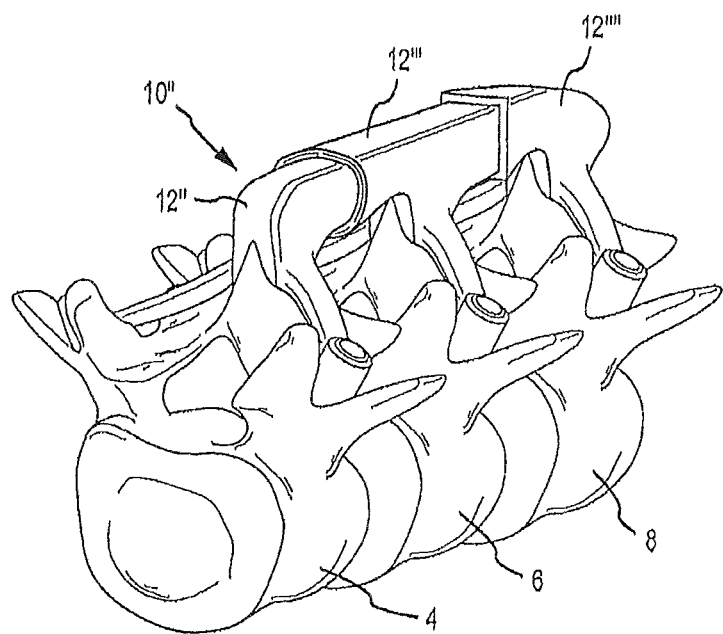

FIG. 9 shows an apparatus according to yet another alternative embodiment of the present disclosure, which is comprised of multiple sections 12", 12"', 12"". Similar to the embodiment shown in FIG. 8, this pedicle screw guide 10" permits alignment and insertion of pedicle screws in multiple levels 4, 6, 8 of the spine. However, the multiple sections 12", 12"', 12"" each have a modified medial body that comprises an engaging end and a receiving end, such that the multiple sections 12", 12"', 12"" may be joined as shown in FIG. 9. The receiving and engaging ends of each of the multiple sections 12", 12"', 12"" are different so that when assembled, only the proper ordering of the sections 12", 12"', 12"" may be achieved (i.e., section 12" may only be joined with section 12"'). This figure demonstrates yet another aspect of the present disclosure, in particular, the ability to mate or join specific devices adjacent to one another to further ensure alignment and mating with the particular anatomical features associated with each device, as well as provide a means for applying corrective force to the vertebrae and visualize the degree of deformity correction.

Figure 10:
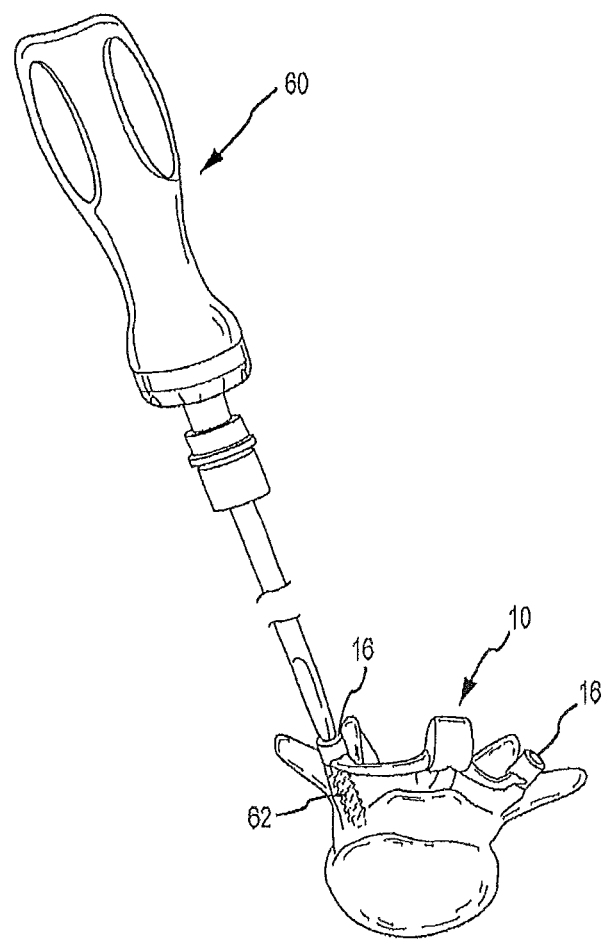

FIG. 10 shows an apparatus according to the embodiment of FIG. 5 with a customized instrument, which may be used in concert with the apparatus during a particular surgical procedure. For example, during a spinal fusion procedure such as the one described above, it is common for the surgeon to attach one or more pedicle screws to the vertebrae of the patient to achieve the desired fusion of intra-vertebral bodies. The cylindrical column 16 may have a internal diameter that corresponds with a gradually increasing external diameter of the instrument 60 such that the instrument 60 may only be advanced into the cylindrical column 16 to a predetermined distance, thereby providing a hard stop and in turn providing means for preventing the pedicle screw 62 from advancing too far into the boney anatomy of the patient. According to yet another embodiment, the hollow portion of the cylindrical column 16 may have a section with a narrower internal diameter (not shown in FIG. 10), which corresponds to a end-stop fitted to the external diameter of the instrument 60 in a manner and location to prevent the instrument from over penetrating the cylindrical column 16 and thereby inserting the pedicle screw 62 beyond a safe limit.

FIG. 11 is a perspective view of an apparatus according to yet another alternative embodiment of the present disclosure. Here, the apparatus is a pedicle screw guide 100 which further comprises a narrow bridge 112 about the medial body, which permits a collar 130 to be coupled with the modified pedicle screw guide 100, as shown in FIG. 12. The collar 130 may comprise a contoured lower surface matching the spinous process of the patient (similar to the longitudinal cavity of the embodiment shown in FIG. 3), and may be inserted into the pedicle screw guide 100 for matching the particular anatomical feature for the vertebrae operated on during the surgery. Thus, in this embodiment, the collar 130, in addition to the lower patient-contacting surfaces 118, 119 of the two cylindrical columns 116, comprises at least one of the patient-matching contours, and may be removed and replaced with other collars of differing contour as required for surgical procedures on different vertebrae. In this embodiment, the cylindrical columns 116 may further comprise one or more apertures 111 to facilitate visualization of the pedicle screw while it is being advanced into the cylindrical columns 116.

FIG. 13 is a perspective view of an apparatus for facilitating a surgical procedure according to yet another alternative embodiment of the present disclosure. In this embodiment, the apparatus formed by the system and method described above is comprised of a laminectomy cutting guide 150. This laminectomy cutting guide further comprises at least one alignment channel 151 for inserting a guide wire or other securing element, and a cutting slot 152 for directing the path of a blade or other cutting edge. As with the pedicle screw guide described in FIG. 3 above, this laminectomy cutting guide 150 also comprises a lower patient-contacting surface 155 which permits the laminectomy cutting guide 150 to mate with one or more vertebral bodies. Although shown in FIG. 13 as a generally rectangular prism, it is expressly understood that other geometrical shapes for the laminectomy cutting guide 150 are equally as practical, and considered within the scope of the disclosure.

FIG. 14 shows yet another alternative embodiment of the present disclosure. In this embodiment the apparatus formed by the system and method described above is comprised of a tube retractor 160, which also comprises a lower patient-contacting surface 165. This patient-contacting surface 165 may be formed in a section 164 of the tube retractor that is selectively removable from the cylindrical body 163 of the tube retractor 165, such that the tube retractor 165 may be reused in a number of surgeries while the section 164 is reformed and coupled to the cylindrical body 163 for each patient. The tube retractor also comprises a generally hollow inner lumen 162 and at least one tab 161 for manipulating during insertion and that assists the surgeon in ensuring proper alignment of the tube retractor 160.

FIGS. 15-17 demonstrate yet another alternative embodiment of the present disclosure. In this embodiment, the template may comprise a patient-matched guide 180 for facilitating the placement of one or more interbody devices, such as by way of example but not limitation, an implantable cage for introducing one or more bioactive substances or bone graft, or an artificial disc. In FIGS. 15 and 16, the patient-matched guide 180 is shown in one potential location relative to a unique anatomical grouping (between two adjacent vertebrae) for assisting the surgeon for placing one or more interbody devices.

In FIG. 17, the patient-matched guide 180 is shown in an exploded view to demonstrate how a plurality of components may be fabricated using the system and method described above for a particular surgical procedure. These components include a patient-specific insert 182, a guide sleeve 184 and connectors 186, which in a finally assembled state form the patient-matched guide 180 shown in FIG. 15.

Referring now in detail to FIGS. 18-19, another alternative embodiment of the present disclosure is shown. According to this embodiment, a surgical template 190 is depicted, which may further incorporate a plurality of fixation devices 198, 198', which may be used to secure the template 190 in a variety of different ways. According to this embodiment, the template 190 comprises an intermediate section 192 oriented to bridge a patient's Spinous Process, and may further comprise apertures (not shown in FIGS. 18-19) for inserting one or more fixation devices 198, 198'. The template 190 may further comprise two laterally extending portions or "wings" 194 which each terminate with a guide 196. The description of the guides provided above in connection with other embodiments disclosed herein is hereby incorporated by reference with respect to this embodiment.

According to the embodiment shown in FIGS. 18-19, fixation devices 198, 198' may be inserted through apertures (not shown) in the intermediate section 192 of the template 190 for stabilizing and securing the template 190 to the patient's Spinous Process. According to one embodiment, the direction and orientation of a first fixation device 198 is different than the orientation and direction of a second fixation device 198' to further improve the stability of the template 190 prior to insertion and placement of the permanent fixation devices. According to yet another embodiment, the apertures may be located in different locations than depicted in FIGS. 18-19, and may be fewer or greater in number according to the demands of the surgery and the patient's specific boney anatomy.

Referring now in detail to FIGS. 20-21, yet another alternative embodiment of the present disclosure is shown. In this embodiment, the template 200 further comprises two additional contacting surfaces 205 which preferably have a hollow opening at the patient-contacting end and an aperture extending therethrough for inserting a fixation device 199, 199'. As described above in connection with FIGS. 18-19, the purpose of the fixation devices 199, 199' is for securing the template 200 to the boney anatomy and facilitate securing permanent fixation devices (not shown) through a plurality of guides 206.

Referring to FIG. 20, the template 200 includes a boss 208 extending from a top surface of the template 200 for inserting a first fixation device 199, wherein the boss 208 is partially hollow to accommodate the shape and length of the fixation device 199. The boss 208 extends above a laterally extending portion or "wing" 204 of the template 200 as shown in FIG. 20. The boss 208 may extend more or less above the template than shown in FIG. 20 to provide a hard stop against over insertion of fixation device 199. Similarly, the opposite laterally extending portion or "wing" of the template 200 also comprises a boss 208' for inserting a second fixation device 199'.

Incorporating the disclosure above with respect to determining and modeling patient contacting surfaces, according to this embodiment the template 200 has at least four patient-specific contacting surfaces 205, 207. This embodiment improves stability and positioning of the template, and allows a surgeon to achieve a dynamically stable surgical template, which in turn ensures that all permanent fixation devices are being positioned and inserted in a direction and orientation pre-determined for the particular surgical demands. This is accomplished by providing the four patient contacting surfaces, which act like independent legs of a table, and being positioned at different locations (and at different planes) with respect to the patient's boney anatomy to further improve the stability and positioning of the template 200.

According to the embodiment shown in FIGS. 18-21, the guides and other patient contacting surfaces may be depth-specific, and may further incorporate specific internal diameters to accommodate insertion of a temporary fixation device to a controlled depth within the patient's boney anatomy. Furthermore, the guides may have specific threaded internal surfaces to accommodate a specific fixation device and to facilitate insertion of a threaded fixation device, such as a screw. In certain embodiments, the templates could be designed for a specific patient to prevent excessive penetration of the fixation devices into the boney anatomy, or facilitate a depth-controlled first set of fixation devices to temporarily secure the templates.

According to yet another embodiment, each of the patient contacting surfaces may have an integrated blade with a patient-contacting cutting surface, integrated about at least a portion of the patient contacting surface to further set and secure the template to the boney anatomy prior to insertion of the fixation devices. The purpose of the blade is to cut through the soft tissue to achieve better template to bone contact between the template and the patient's boney anatomy. The hollow portions of the guides and other patient contacting surfaces of the template further permit soft tissue to become positioned within these hollow surfaces after the template has been set in the desired location, further securing the template to the patient's boney anatomy. The blade may be substantially cylindrical or ring shaped to match the shape of the guide, or may be oval, polygon, or other shape to match a patient contacting surface.

To add further stability to the seating and placement of the patient contacting surfaces described herein to the patient anatomy, the contacting surfaces may further comprise one or more spikes or teeth, which serve to contact and at least partially penetrate the patient anatomy to secure the device in place. In one embodiment, the spikes or teeth may be made of the same material and may be permanently attached to the patient contacting surfaces. In another embodiment, the spikes or teeth may be made of a different material, such as the ones described herein, and may further be selectively inserted onto one or more of the patient contacting surfaces as desired.

Referring now to FIG. 22, yet another alternative embodiment of the present disclosure is shown. According to this embodiment, the template 220 has a plurality of patient contacting surfaces 212, 219, which are achieved through the use of a "floating" patient-matched component 214, which may inserted into one of a plurality of guides 216 either before or after the first set of patient contacting surfaces 212 are positioned. The patient-matched component 214 may further comprise a longitudinal key 218 which corresponds to a slot or groove (not shown in FIG. 22) in the guide 216 for facilitating proper location (rotationally) of the patient-matched component 214 respective of the template 220.

Thus, according to this embodiment, the template 220 may be secured in a first position by using at least two fixation devices (not shown) securing the template 220 to its desired location, and then a plurality of patient-matched components 214 may be inserted into the guides 216 of the template 220 and seated about two distinct locations of the patient's boney anatomy.

Referring now to FIG. 23, yet another embodiment of the present disclosure is shown, wherein a instrument 240 may be used to facilitate insertion of a template 230 according to various embodiments disclosed herein. The instrument 240 is preferably comprised of a handle 242 and an extending arm 244, the length of which may vary depending on the specific patient's anatomical features and/or surgeon preferences. At the distal end of the extending arm 244 is a tab 246, which is formed to match a corresponding slot 236 located on one surface of the template 230. In operation, the instrument 240 may be joined with the template 230 and used to insert and position the template 230 within the patient's surgical site.

Referring now to FIG. 24, another alternative embodiment of the present disclosure is shown. According to this embodiment, a template 250 may be provided which is not patient-specific (but in an alternate embodiment, may be patient-specific) and further provides means of attaching a plurality of patient-specific components 254 to the template 250. As shown in FIG. 24, the components 254 may be secured to the template 250 by aligning apertures 252, 258 and attaching one or more securing devices (not shown in FIG. 24) such as a screw, pin, or other like device. Once the components 254 are secured to the template 250, the patient contacting surfaces 262 may be used to guide and position the template 250 with the integrated components 254 in the desired location. In this manner, a standard template 250 may be provided prior to obtaining any patient data, and combined with patient-specific components 254 that are formed after the patient anatomical data has been captured, thereby eliminating custom machining or fabrication of the template for a specific surgical application.

According to this embodiment the template 250 may be reusable, or in an alternative embodiment may be disposable. The template 250 may be comprised of any of the materials listed herein, but in a preferred embodiment is formed of a metal, metal alloy or a polymeric-based material. According to yet another alternative embodiment, the components 254 may snap into place or have a friction-fit connection and therefore do not require screws or other securing devices to attach to the template 250. In yet another alternative embodiment, the template 250 may be provided in a variety of set sizes and orientations to cover variability in patient anatomy and different size vertebral bodies (with respect to different levels or regions of the patient's spine).

Referring now in detail to FIG. 25, another embodiment of the present disclosure is shown. In this embodiment, the template 270 has a plurality of patient contacting surfaces 276, 278 and further comprises a plurality of clamps 272 for securing the template 270 to the Spinous Process of the patient. According to this embodiment, the clamps 272 each have a patient contacting surface 274 (here designed to contact the Spinous Process about each lateral side) to secure the template to the desired location of the patient's anatomy. Each of the clamps 272 may be positioned laterally with respect to the template 270 (shown in an elevation view) and affixed to a set position with respect to the body of the template 270. The clamps 272 may be secured in a fixed position against the Spinous Process by a number of known means, including a latch mechanism, a ratcheting mechanism, a direction-specific resistance mechanism, or a selectively-releasable tightening mechanism. In this embodiment, the clamps 272 allow oppositional forces occurring in the boney anatomy to become balanced relative to the patient's template 270. In turn, the clamping mechanism ensures and maintains the alignment of the template 270 relative to the boney surfaces further ensuring accuracy with respect to insertion of permanent fixation devices. The clamps can take a variety of shapes or embodiments including pins, paddles, or any other type of opposing surfaces that apply juxtapositional stabilizing forces.

According to one embodiment, the surgical guides depicted in FIGS. 24 and 25 may include surfaces about the patient contacting end of the guide sleeves (see 254, FIG. 24) to conform to the soft tissue existing at the facet complex where the patient contacting end of the guide sleeve contacts the patient's vertebrae (see 278, FIG. 25). Thus, according to this embodiment, the generally cylindrical guide sleeve(s) comprise a patient contacting surface that resembles a half cylinder or partial cylinder (as shown in FIGS. 24 and 25) to avoid contact with this soft tissue.

In one alternate embodiment, the surgical guide may further comprise one or more portions that have been cut-out or may selectively be cut-out or broken off to facilitate placement. One such surgical guide is shown in FIGS. 26A and 26B. According to this embodiment, the surgical guide comprises a plurality of patient contacting surfaces, one or more of which has been modified to facilitate clearance of the guide as it is being placed into position (see surfaces 282 on FIG. 26A). Furthermore, a surgical guide as described herein may comprise one or more clamping elements for securing the guide in a preferred location, such as the clamp 284 depicted in FIGS. 26A and 26B.

According to yet another embodiment, the guide sleeve(s) 254 may further permit insertion of one or more inserts 288, as shown in FIGS. 27A and 27B. These inserts 288 may be sized with external diameters for mating with the interior diameter of the guide sleeve(s) 254, and have an interior aperture running longitudinally through the insert 288 for accommodating a drill bit or tap (by way of example) of varying sizes. In practice, the insert 288 may facilitate and guide a drill bit for creating a pilot hole for further insertion of a fixation device, such as a screw. According to one embodiment, inserts 288 may further comprise one or more indicia for identifying the specific insert 288 for a particular level of a patient's spine, or other indicia indicating the direction, orientation, use or purpose of said insert 288.

Referring now to FIG. 28, the inserts 288 provided with the surgical guides for mating with the guide sleeves 254 may have a varying length L, and may be made longer or shorter depending on the geometry of the guides, the patient's anatomy, the purpose of the insert, etc. For example, if a greater depth of a particular drill is required, the insert 288 may be shorter to accommodate further penetration of the drill bit into the patient's vertebrae. Likewise, the interior aperture of the insert 288 may have varying diameter depending on the precise tool or instrument that is intended to be used with the insert (as depicted in FIGS. 29A and 29B). In this manner, a surgeon may insure that he or she is using the proper tool, such as a drill or tap, with each of the inserts (which may further include one or more indicia to indicate the location or specific use intended for said insert) when performing a surgical procedure. Further illustration of the principles described above see FIGS. 29A and 29B, which depict an insert with a 4.5 millimeter aperture diameter for placement of a tap instrument and a ⅛ inch aperture diameter for use in connection with a ⅛ inch drill bit, respectively.

Referring now to FIG. 30, according to one embodiment the inserts 288 described above may also include patient-specific contacting surfaces 294, for further matching the insert 288, in addition to the guide sleeves 254, with the patient-specific anatomy. This allows greater stability and positioning of the insert 288, and the guide with the insert 288 included, in the proper location. In addition, for inserts 288 used in connection with a drill bit or other vibrating or oscillating tool, these patient-matching surfaces 294 on the insert 288 would also prevent the distal end of the drill bit from "walking" or moving on the surface of the vertebral body when creating the initial pilot hole, thereby reducing the risk of incorrect trajectory of a fixation device.

According to further embodiments of the present disclosure, the patient contacting surfaces, formed by one or more protrusions extending from the main body of the surgical guide described in greater detail above (and according to several embodiments disclosed herein) may comprise a sharp or semi-sharp contacting edge for penetrating and affixing to the soft tissue surrounding the patient's anatomical feature, such as a facet joint. The contacting surfaces may, according to this embodiment, comprise recessed cavities for soft tissue incursion. These recessed cavities create edges around the outside of the legs, which could be sharp or selectively sharpened to facilitate cutting through soft tissue to rest/mate with underlying bone. This is particularly important for spinal surgical procedures where the precise location of the patient contacting surface must be within a small degree of error, and must remain permanent throughout the procedure.

Referring now in detail to FIG. 31, the insert may further comprise a key or notch 296 about one surface of the generally cylindrical body of the insert, which is configured to mate with a cutout or slot 298 on the guide sleeve 254 of the device. In this manner, the proper rotation/orientation of the insert 288 is insured when guiding the insert into the hollow body of the guide sleeve 254.

Referring now to FIGS. 32A-34B, further illustrations of a cutting guide (such as the one depicted in FIG. 13 above), are provided. According to one embodiment, the cutting guide comprises a plurality of patient-specific contacting surfaces 302 about at least one surface of the cutting guide. The cutting guide further comprises, in a preferred embodiment, a patient-specific "track" 303 for facilitating insertion of a cutting instrument (as shown in FIGS. 33A-C) and controlling the depth of insertion for that instrument to prevent unnecessary cutting of the underlying surface during a particular surgical procedure by further providing one or more instrument contacting surfaces 304. According to the embodiment shown in connection with FIGS. 32A-34B, the cutting guide may be provided for a laminectomy. According to other embodiments, the patient-specific guide may be fabricated for use in performing a corpectomy, a Pedicle Subtraction Osteotomy (PSO), a Smith-Peterson Osteotomy (SPO), a Vertebral Column Resection (VCR), or an Asymmetric Osteotomy (in either the sagittal or coronal plane), among others.

These patient-specific cutting guides may be fabricated from patient anatomical data, and may assist in performing complex procedures with greater certainty in their outcomes. For example, certain osteotomies, specifically PSO and SPO, require a great deal of surgical skill and are often time consuming. This is due in part to the intimate relationship of the vascular and neural elements to the boney structures, which create navigational challenges for a surgeon to safely and efficiently resect the bone during one of these procedures. This is especially true from a posterior approach. By using a patient-specific guide, a surgeon may confirm positioning and alignment of the cutting trajectory and path prior to initiating the procedure, and in furtherance of the disclosure provided above in relation to FIGS. 32A-34B, may also provide a degree of depth control essential for avoiding contact with vascular and neural elements.

In one embodiment, the cutting tool associated with the cutting guide shown in FIGS. 32A-34B is typical of the type of tools currently used in surgical procedures today. According to another embodiment, a specialty cutting bur or tip may be included with the instrument to facilitate further control of the location and depth of the instrument, as described in further detail below. For example, as shown in FIGS. 33A-33C, the cutting portion of the instrument may have a track ball 308 that prevents greater insertion of the instrument into the cutting guide than required for the patient-specific procedure.

As shown in greater detail in FIGS. 34A-34B, the track ball 308 may be inserted into a first portion of the "track" 303 of the cutting guide, but not permitted to insert a second or deeper portion of the "track" of a cutting guide (through which the cutting surface is permitted to travel), thereby insuring proper depth of the cutting instrument. Further geometrical configurations other than those shown in FIGS. 34A-34B may be provided that allow the track ball 308 to move horizontally with respect to the top surface of the cutting guide, and in some instances laterally and downwardly into the track 303 of the cutting guide. In this embodiment, the cutting instrument would therefore be permitted to move at a certain depth about a patient's anatomy in a certain location of the "track" 303 of the cutting guide, but achieve a greater depth at yet other locations about the "track" 303 of the cutting guide. Thus, the depth permitted with respect to the instrument relative to the cutting guide may be variable about the "track" 303 of the cutting guide.

Other benefits achieved from the use of these patient-specific cutting guides include: providing means to achieve quick and controlled removal of bone; providing spatial orientation of cutting tools used during the procedure; ensuring correct orientation of cuts, both through controlled guiding of the instrument and visualization during the pre-surgical planning process; providing accurate calculation of deformity correction, prior to cutting; providing accurate bone resection, which in turn ensures deformity correction; depth controlled cutting restrictions to protect neural and vascular elements; controlled cutting vector and avoiding contact or injury to neural elements; and ability to provide approach for cuts in a posterior, anterior, posterior lateral, transforaminal or direct lateral approach.

FIG. 35 is a top plan view according to yet another alternative embodiment of the present disclosure. In this embodiment, the device 310 may provide one or more patient contacting elements comprising break-away portions 314, which allow for placement of a fixation device (such as a pedicle screw) without detaching the device from the patient's boney anatomy. The break-away lateral edged may be formed by creating slots 315 in the surfaces of the surgical guide portions of the device, which provide perforation axes for the portions 314 to be broken.

According to this embodiment, the guide sleeve may be asymmetric, which would permit two different inner diameters: one that facilitates guidance of the hand tools (i.e. drill, tap) and one that accommodates the boss or cap of the device (such as the tulip of the pedicle screw). Once the break-away portion 314 of the guide sleeve is removed, a clear view and path to the vertebra is possible and allows pedicle screw placement without removing the guidance device.

FIG. 36 is a detailed view of the device according to the embodiment shown in FIG. 35. In FIG. 36, a detailed view of the slots 315 are shown, which in a preferred embodiment may be formed during the fabrication of the device 310, but in alternate embodiments may be formed after the device has been fabricated by perforation or other techniques for creating a slot 315 about a certain surface of the guide sleeve of the device 310.

FIGS. 37-39 are additional views of the device according to the embodiment shown and described in relation to FIG. 35. In FIG. 37, the asymmetrical guide sleeve is shown with the two break-away portions 314 separated from the device 310. In FIG. 38, the embodiment shown and described in relation to FIGS. 26A-B is shown, but now having an asymmetrical guide sleeve with break-away portions 314 as described above.

FIGS. 40A-D are additional perspective views of the devices described above in relation to FIGS. 35-39, according to the embodiments having at least one or more break-away portions. Once removed, the break-away portions are preferably disposed by the surgeon.

Each of the embodiments described herein may be provided in a modular (i.e., single level) or a monolithic (i.e., multilevel) configuration. Thus, for ease of facilitating the description provided herein, certain embodiments have been shown in one (modular or monolithic) embodiment, but may be provided in a different (monolithic or modular) configuration without departing from the spirit of the disclosure. In various aspects, the monolithic embodiments may comprise anywhere from two to ten levels with respect to vertebral bodies, or enclose multiple locations of a patient's boney anatomy other than the spine. It is expressly understood that the embodiments described herein are for the purpose of illustrating certain embodiments of the disclosure, and are not intended to be limiting with respect to the scope of the disclosure.

According to the various embodiments described herein, a variety of fixation devices may be quickly and easily fabricated for use in a surgical or educational setting, including but not limited to pins, screws, hooks, clamps, rods, plates, spacers, wedges, implants, etc. Similarly, a variety of instruments and/or other devices may be fabricated based on patient-specific data, including but not limited to patient-matched inserters, scrapers, cutters, elevators, curettes, rongeurs, probes, screwdrivers, paddles, ratcheting mechanisms, removal and rescue tools, cannula, surgical mesh, etc.

Included among the apparatus that may be fabricated using patient-specific data and including a plurality of patient-matched surfaces are devices used as implants, including numerous implants used to restore disc space height in a patient's vertebrae. For example, a variety of patient-matched metallic, polymeric or elastomeric implants may be fabricated using the methods described herein, where certain patient contacting surfaces of the implant accurately and precisely match the anatomy of the patient. In one embodiment, the implant may be matched to an anatomic feature of a patient that has degenerated and needs to be restored. In another embodiment, the implant may be necessary to correct structural or physiological deformities present in the patient anatomy, and thereby serve to correct position or alignment of the patient anatomy. Other implants may be patient-specific but do not serve a restorative or other structural function (i.e., a hearing aid implant casing).

The implants described herein may be manufactured via additive manufacturing. In the context of spinal implants, the implants may be used in all approaches (anterior, direct lateral, transforaminal, posterior, posterior lateral, direct lateral posterior, etc.). Specific features of the implant can address certain surgical objectives, for example restoring lordosis, restoring disc height, restoring sagittal or coronal balance, etc.

Other applications contemplated by the present disclosure include interbody fusion implants, disc space height restoration implants, implants having footprint matching, surface area maximization, shape and contour matching to endplates or other vertebral defects, and may further specify the contact surface such as the relative degree of roughness or other surface features. For example, an implant may be fabricated based on the patient anatomy which further comprises a direction-specific shape, such that the implant may fit through an access portal and into the disc space without difficulty. Alternatively, the implant may be fabricated in a manner to account for anatomic constraints both at the point of implant and through the path the implant must travel, and may further compensate for anatomical defects. In the context of a spinal implant, the implant may further specify a desired angle of lordosis or coronal defect correction, specify a patient-specific height of the implant or (desired height following disc height restoration), specify a degree of expansion permitted (for expandable implants), and may be unidirectional or multi-directional depending on the surgery and the surgeon preference.

According to one embodiment, the fabrication of a patient-matched device may be used to create patient-matched vertebral plates. By way of example but not limitation, patient data may be obtained to create matching surfaces of one or more anterior cervical or lumbar plates used for spinal reconstructive surgeries. Plates may comprise contours or surface features that match boney anatomy, including matching surfaces spanning more than one segment or vertebrae. In yet another embodiment, the patient data may be used to create specific patient-matched plates with identifiers for the location of the plate, and may further comprise custom drill holes or other alignment points specific to the patient. Other types of plates, besides those utilized in spinal surgery and described, may incorporate patient-matching features described herein without departing from the present disclosure.

Referring now to FIGS. 41-44, an alternate embodiment of the present disclosure is shown. In certain procedures, there is a need for a plurality of trajectories in or near a particular surgical site. For example, a first fixation device may need to be secured in a first trajectory, and a second fixation device may also be needed to be secured in a second trajectory that is different than the first. According to this embodiment, multiple trajectories may be achieved without requiring multiple guides, and indeed may be facilitated by the customized guide or components thereof.

With reference being made to FIGS. 41-44, the present embodiment may comprise a first guide sleeve 320 having a first trajectory through aperture 325, and may further comprise a second guide sleeve 320' having a second trajectory D and an insert having a third trajectory C. According to this embodiment, an insert may be used with a surgical guide or guide sleeve, such as the type described herein, or with the guide depicted in FIGS. 42-44. The insert may be generally cylindrical in shape and may be similarly sized so that it may be inserted into a guide sleeve, and preferably includes at least one tab 322, 322' for proper alignment with a slot (not shown in FIG. 41). The registration of the guide against the boney anatomy permits the surgeon to validate the proper positioning of the guide and thereby the customized orientation of the insert providing the orientation for placement of a fixation devices in the desired locations.

The concept for this additional embodiment includes using at least one part of the guide (when placed/attached to patient's anatomy) to create additional trajectories into the patient anatomy. By way of example but not limitation, the following aspects of the surgical guide described herein may be used to determine and create alternate trajectories without the need to create a new guide:

- The guide sleeve(s);
- The guide sleeve insert(s);
- The holder attachment area;
- The arms of the guide (i.e., via clips, holes, registration points, etc.).

Any point of reference associated with the above components may be used to determine the second or other multiple of trajectories. For example, an axis line, tangent line, intersection, radius, pre-determined marker (such as a radiographic marker), surface feature, end point or other registerable location may be used as a reference for determining the orientation of a second insert.

Similarly, any known point or geometry on the guides can be used to create another modular part that can "snap" into the guide providing a plurality of trajectories. For instance, the holder attachment area of the guide could be used to attach an "outrigger" arm that provides a different trajectory. This could also be applied to a hole through the arms of the guide, such as the fixation screw holes, into which the outrigger arm could be inserted.

Another embodiment could use the fixation screws or pedicle screws as additional spatial orienting features. The fixation screws and pedicle screws are placed in planned, specific orientations. Because the length and direction of these screws is predetermined, trajectories for adjacent levels can be based off of the orientation and features of these screws.

Alternatively, a surgeon may use the locations of the fixation screw holes in the guides to create additional trajectories, including with or without the need for a custom insert. In another alternate embodiment, the surgeon may use pedicle screws placed in a specific orientation to create additional trajectories.

FIGS. 42A-B are top plan views of a guide 400 according to another alternative embodiment of the present disclosure. The guide 400 preferably comprises at least a first set of guide sleeves 410 and a second set of guide sleeves 412. This embodiment is particularly useful for, by way of example but not limitation, sacroiliac fixation, due in part to patient-matching surface data not being ascertainable in certain areas requiring access during the procedure. More particularly, in order to reach the iliac crest bilaterally, a very wide soft tissue exposure is required, which is unduly disruptive to the normal anatomy. By using, for example, the location of the S1 pedicle screw guide, custom guide trajectories may be fabricated. The orientation of the trajectory may be determined by employing a more medial location of registration, and thereby permit access to a variety of iliac and sacral trajectories without creating a new guide or other custom fabricated instruments.

In a preferred embodiment, the guide of FIGS. 42A-B is floating above and does not necessarily contact the iliac crest, which is desirable in certain patients who possess unstable or sensitive anatomy. Additional trajectories may be based on the original orientation of the guide sleeve or the guide sleeve insert. Furthermore, trajectories into other sacral structures, such as the sacral ala, the S2 pedicle, or a trans-sacroliliac joint may also be achieved.

According to at least one embodiment, the patient-contacting end of the insert may not be patient-matching, and according to other embodiments may provide orientation as well as depth control for the fixation device to be placed through the second trajectory. While FIGS. 41-44 show only one different trajectory, it is expressly understood that additional trajectories may be provided with a single guide insert.

FIG. 43A is a top plan view of the guide for a three level procedure (sacroiliac plus 1 additional level), which depicts a pair of inserts having two different trajectories than a first pair of guide sleeves. FIG. 43B is a detailed plan view of the device shown in FIG. 43A. More specifically, the guide sleeves 422, 423 provided with this embodiment permits the variation of the inserts 424 used with the guide to provide a customized and unique trajectory, which is different from the general trajectory of the sleeve(s) 422, 423 of the guide. The inserts 424 may comprise different and/or additional trajectories as those shown in FIGS. 43-44, or alternatively may extend outwards from the body of the guide in desired directions, which may not be coaxial to the guide sleeve(s).

This embodiment may also be used in tumor surgery or where the bone surface is not present or is altered (revisions). The guides from adjacent levels may be used to provide these additional trajectories.

Referring now to FIG. 45, two surgical drilling sleeves 432, 434 are depicted in a side elevation view, which may be used with a surgical guide according to an alternate embodiment of the present disclosure. Drilling sleeves are generally known in the art, however, the present embodiment relates to custom drill sleeves 432, 434 which may be placed through one or more patient-matched inserts or guide sleeves to provide contact with the boney surface at the distal end of the drilling sleeve (see FIG. 46). While custom drill sleeves 432, 434 may be made of any material, a preferred embodiment would have the sleeves 432, 434 manufactured out of a metal or metal alloy that is of sufficient strength and brittleness that breaking and/or flaking of the drill sleeve material is avoided. Accordingly, the drill sleeves 432, 434 may withstand the effects of high-speed drilling without damaging the sleeves 432, 434 or permitting material from the sleeves to become deposited in the drilling site, as well as re-use of the drilling sleeves 432, 434. The sleeves 432, 434 must also withstand the high temperatures encountered during sterilization. Another benefit of metallic sleeves 432, 434 is the ability to "trephine" or machine with a cutting surface to permit the distal end 435 of the guide to "bite" into the bone and provide means for fixation.

FIG. 46 is a front elevation view of a surgical guide 450, guide sleeve 452 and drilling sleeve 432 assembly according to an alternate embodiment of the present disclosure. In this embodiment, a drilling sleeve 432 is provided which permits a gap between the intersecting boney anatomy and the sleeve 432. Alternatively, a trephined or patient-specific edge of the sleeve may provide better contact with the underlying boney surface.

The drill sleeves placed through the patient-matched guide sleeves and into the bone at opposing, dissimilar angles provides additional fixation of the guide to the vertebra. The convergence of the drill sleeves through the insert also eliminates the need for additional fixation. It is expressly understood that more or fewer inserts and/or guide sleeves may be provided with a patient-specific guide for facilitating a drilling operation in a surgical procedure without deviating from the spirit of the present disclosure. In one embodiment the sleeves are disposable, and in other embodiments the sleeves are reusable.

FIGS. 47A-D are views of an assembly tray and method of arranging patient-matched surgical devices according to one embodiment of the present disclosure. According to this embodiment, an assembly tray 460 is provided with a plurality of patient-specific devices D, which enhances the organization, structure and efficiency of the arrangement of devices D according to the preferences of the surgeon or to the particular surgery.

The assembly tray provides an arrangement that is essential to the users success in the operating room, including but not limited to the following factors:

Number of and specific levels Z1-Z4 of surgery (i.e., where multiple guides are to be used);
Pedicle screw implant diameter and length selection (including optional variations);
Navigational guide(s) corresponding to the selected implants;
Combination of guides and/or sleeves, including in series and/or with monolithic guides provided for the particular application.

According to one embodiment, the assembly tray 460 consists of "zones" Z1-Z5 that contain all of the necessary parts needed to operate on a specific area of in a specific level. The tray 460 is preferably organized and the devices D arranged in the desired location prior to the surgery, and may also arrive at the facility for sterilization immediately prior to the operation. Each "zone" on the tray may contain the guide D, inserts I, and pedicle screws S for, by way of example but not limitation, a particular vertebral level. Additionally, any drill sleeves, fixation screws or other accessory specific to a particular vertebral level may be included in that "zone". The tray preferably comprises unique indicia 462 for the particular surgery, which correspond to the different devices, areas, levels, etc.

The trays may come in various sizes dependent on the size of the surgery being performed (i.e. 2 level versus 3 level), and may be labeled to match zone to level of the spine (Zone 1 would be for L1 ) or comprise other unique indicia. For example, the zones may be color-coded and the different corresponding inserts complementary to a particular guide may be coded similarly to facilitate matching of inserts with guides for a certain area or level. In another embodiment, the components are bar coded, RFID coded or have other unique features which may be read by appropriate scanning equipment.

Furthermore, the tray provides safer packaging and orientation of the guides. This is especially important for plastic guides that, due to the delicate nature of the material and the different projections fabricated for a particular guide, may require protection during transportation or steam sterilization. The packaging is needed to ensure dimensional integrity during these critical steps.

As described above, certain embodiments of the present disclosure may be incorporated into surgical methods and apparatus for use in performing operations on the cervical spine (i.e., C1 through C7). Due to the similarities in the geometry of the vertebrae between the thoracolumbar and cervical spine, many of the concepts described above may be incorporated into a patient-matched surgical guide for use in a cervical spine procedure. However, unique characteristics of the cervical vertebrae and surrounding anatomy require consideration when orienting and placing a patient-matched cervical guide, several of which are discussed below in relation to FIGS. 48-63.

Referring now to FIGS. 48A-C, one embodiment of the present disclosure for use in a procedure performed at level C7 is shown. According to this embodiment, the cervical guide 470 comprises a plurality of patient-matched contacting surfaces in a manner that permits a surgeon to accurately and reliably place the cervical guide in the proper position relative to the patient's boney anatomy. As shown in FIG. 48A, the cervical guide of this embodiment comprises an arch or bridge section 471 in the medial body of the guide 470, which is oriented to avoid the spinous process and be placed in contact with the vertebral body (in this embodiment, at level C7). The cervical guide 470 preferably comprises a first patient-specific surface preoperatively configured to mate with a corresponding surface of a first transverse process, and a second patient-specific surface preoperatively configured to mate with a corresponding surface of a second transverse process opposite the first transverse process. The cervical guide 470 further comprises first and second legs 472 having corresponding first and second ends, wherein the first and second ends provide the location of the first and second patient-specific surfaces configured to mate with corresponding portions of first and second transverse processes of the vertebra.

In one embodiment, the first and second legs 472 are substantially cylindrical as shown in FIG. 48A-C, and may further be hollow to permit a sleeve to be inserted therein. In one embodiment, as described in greater detail above, the sleeve may comprise a distal end having a patient-specific surface which mates with corresponding anatomical features of the patient after the sleeve is inserted through the hollow portion of the first or second legs 472. In certain embodiments, the sleeve and the legs 472 comprise patient-specific surfaces. In another embodiment, only one of the sleeve and the legs 472 comprise patient-specific surfaces.

The sleeves may comprise an aperture for inserting a device or instrument or tool, such as a screw, K-wire, or drill. In certain embodiments, the guide 470 is oriented to permit insertion of a sleeve configured to receive one of a pedicle screw, a lateral mass screw, a cortical screw or a facet screw. The screws and other devices contemplated for use with the guide of the present disclosure may be standard or may be customized for use only with a particular guide or at a particular level.

As shown in FIG. 48B, the guide may further comprise a first and second extension 474 on the first and second legs 472, which may comprise an auxiliary aperture and path for inserting, for example, a fixation screw. According to this embodiment, the extension 474 may receive a fixation screw for insertion through the aperture of the extension and into the transverse process for securing the cervical guide 470 to the patient's boney anatomy. It is expressly understood that other types of devices may be utilized to temporarily ensure seating of the cervical guide to the patient without departing from the novelty of the disclosure as discussed herein.

Referring now to FIG. 48C, a top plan view of the cervical guide described in relation to FIGS. 48A-B is shown. The arch or bridge 471 is shown avoiding the spinous process, although in alternate embodiments the lower surface of the bridge 471 may further comprise a patient-specific surface for mating with a corresponding surface of the spinous process. Examples of this embodiment are described below in relation to FIG. 54A. The cervical guide 470 may further comprise indicia relating to the patient, the particular guide, the location or level of the spine where the guide is to be used, the size of the device or instrument or tool to be received by the particular guide, the orientation of the guide, etc. Several examples of indicia are depicted in FIGS. 48A-C. The cervical guide 470 may also comprise a slot, channel, groove or keyhole for receiving the distal end of an instrument, such as an inserter.

Referring now to FIGS. 49A-C, another embodiment of the present disclosure is shown, which relates to a cervical guide for use at level C2. This particular level of the cervical spine requires orientation of the bridge 491, legs 492 and sleeves described above in relation to FIGS. 48A-C. In particular, the first and second legs 492 are oriented with a slightly upward trajectory for placement of a device, instrument or tool therethrough, which is ideally oriented for contacting the pedicle of the vertebrae. Although this embodiment is depicted without an extension for receiving a fixation screw or other device for temporarily seating the guide 490, it is contemplated that such an extension may be provided with the cervical guide for level C2. Other levels besides C7 and C2, as described in relation to FIGS. 48-49, are also contemplated for applications of the present disclosure.

Referring now to FIGS. 50A-D, another embodiment of the present disclosure is shown. This particular cervical guide 500 includes sleeves 510 oriented to receive inserts (not shown) for receiving, for example, lateral mass screws. The particular guide shown is designed for application with level C5 of the cervical spine. As shown best in FIG. 50C, the bridge 502 includes a slot 503 for receiving the distal end of an instrument, such as an inserter. In another embodiment, the slotted portion of the bridge 502 may include a connection for joining two separated portions of the cervical guide in a medial area. Further details regarding this particular embodiment are described in relation to FIGS. 53A-E. In addition to the patient-specific legs shown in FIGS. 50C-D, this embodiment further comprises a first and second tab 520 for placement under the laminar surface of the vertebrae. The tabs 520 assist in securing the cervical guide to the patient-specific anatomy, and are described in the following paragraph in further detail.

Referring to FIGS. 51A-C, additional views of the embodiment depicted in FIGS. 50A-D are shown. According to this embodiment, the tabs 520 are oriented to separate the facet joint capsule and enter the facet joint when the cervical guide 500 is placed into position. One or both sides of the tabs 520 may be patient-matching. The patient-matching tabs 520 may enter the facet joint above or below, or in certain embodiments provide both. In this embodiment shown, the tabs 520 create an interference fit with the facet joint and secure the cervical guide in place. The tabs 520 may be made of material suitable for flexing to permit the interference fit described above, which may be the same or a different material than the remainder of the surgical guide. The tabs 520 may also be made of a non-flexible material, utilizing the guide material's flexibility to permit the interference fit described above.

Referring now to FIGS. 52A-C, an embodiment of the present disclosure is shown that depicts a slotted bridge 502, which further comprises an aperture 504 for receiving a device, such as a fixation screw, which in this embodiment is placed into the spinous process. In one embodiment, the aperture 504 is threaded, and in another embodiment (as depicted in FIG. 55B) it is not. The aperture 504 may further comprise a specific trajectory, for example by orienting the fixation screw shown in FIGS. 52A-C in a more upward direction as desired for securing the cervical guide to a particular level of the cervical spine. The embodiment shown in FIGS. 52A-C may also be incorporated into an embodiment comprising a patient-specific surface located on the lower surface of the bridge 502 for mating with a corresponding surface of the spinous process, such as the embodiment described in relation to FIG. 54A.

Figure 53A:
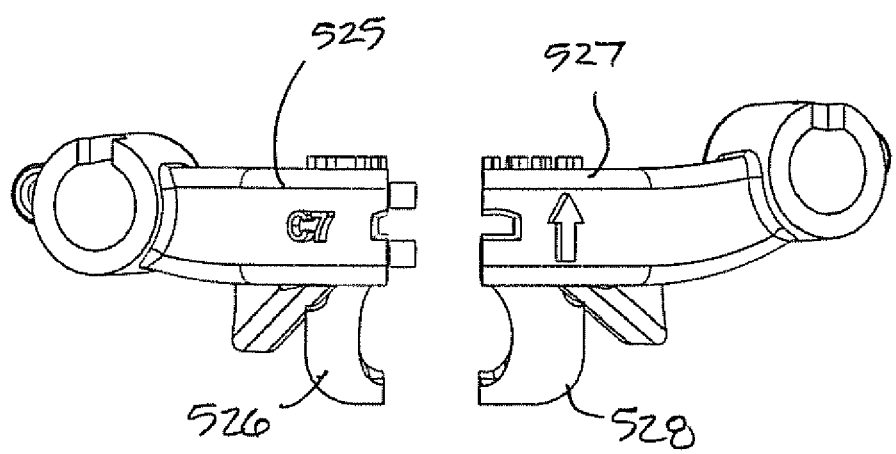

According to one alternate embodiment, the cervical guide described above may further comprise means for locking Referring to FIGS. 53A-E, such an embodiment may comprise means for locking a first section 525 of a guide to a second section 527 of a guide, and further comprise a first collar section 526 and a second collar section 528 oriented to mate with each other about a particular anatomical feature, such as the spinous process. The first and second section 525, 527 and first collar section 526 and second collar section 528 may be joined by suitable techniques known in the art, including but not limited to by inserting one or more tabs into complementary slots on the adjoining surfaces as shown in FIGS. 53A-C. In this manner, the joining of the first and second sections 525, 527 may permit an interference fit by first placing the first and second legs of the cervical guide in position, and then joining the first and second sections 525, 527 of the guide. The interference fit is caused by the tension in the first and second section 525, 527 of the guide being joined while the first and second legs (and the corresponding first and second patient-specific surfaces) remain positioned against the patient's boney anatomy. In addition to, or instead of, an interference fit, one or more pins and/or screws may be passed between the first and second sections 525, 527 of the guide in order to join them into a rigid assembly. These pins and/or screws may additionally pierce the spinous process, or any other part of the vertebral anatomy, in order to stabilize and fix the guide assembly to the bone. While the first and second collar sections 526, 528 shown in the Figures do not have patient-specific surfaces, it is expressly understood that including this feature is within the scope of the present disclosure.

As referenced above, the cervical guides may further comprise a patient-specific surface on a lower portion of the bridge for mating with the spinous process, as depicted in FIGS. 54A-C. The patient-specific surface may be substantially concave for receiving a complementary convex surface of the spinous process located below the location of the bridge. The cervical guide in certain embodiments may also comprise a slot, channel, groove or keyhole for receiving the distal end of an instrument, such as an inserter. An exemplary inserter is depicted mating with a slotted portion of the cervical guide in FIGS. 54B-C. As best seen from FIG. 54C, the distal end of the inserter may comprise two tines, whereby one of the tines may be received within the slot located on the bridge of the guide and the other tine placed on the lateral side of the bridge. The insertion instrument may also be rotated 180 degrees to permit the second tine to be placed against the opposite lateral side of the bridge. In certain embodiments, the tines may comprise an interior surface that includes texturing or a plurality of small barbs for gripping into one or more the surfaces of the bridge, or to contact and become joined with complementary dimples in the surfaces of the bridge (which are not shown in FIG. 54C).

Figure 59A:
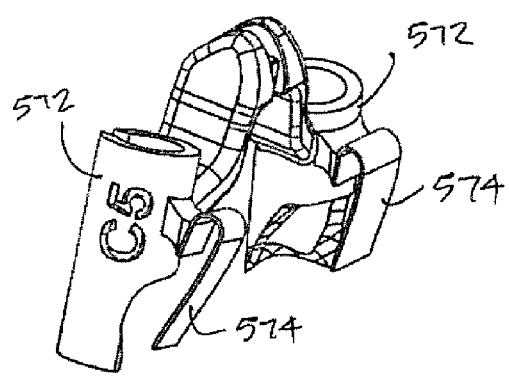
Figure 59B:
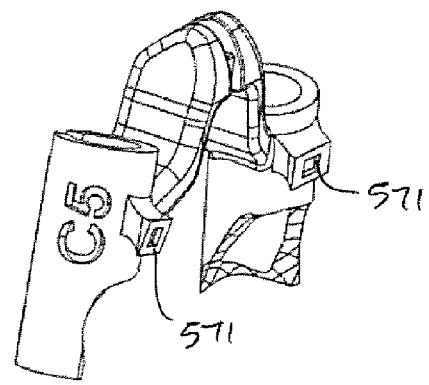
Figure 59C:
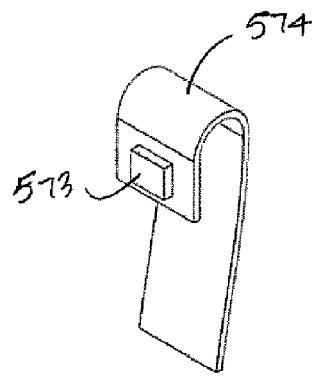
Figure 59D:
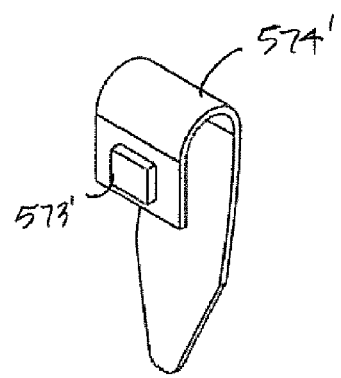

According to yet another embodiment, the cervical guide may further comprise one or more apertures for placement of a clamp, such as the type shown in FIGS. 55A-C. The clamp 540 may be secured and tightened by providing a threaded aperture and a corresponding threaded post of the clamp 540, or may have a threaded post and a corresponding nut to lock the clamp 540 into the proper position. As shown in FIG. 55B, the clamp 540 may be positioned against an anatomical surface of the vertebrae and then tightened into a secured position by way of the threaded post and threaded aperture or nut, as is the case in the embodiment shown in FIG. 55C. More than one clamp 540 may be provided to improve the act of securing the cervical guide. In this same manner, one or more tabs or hooks may be provided with the cervical guide to secure the guide to the patient's boney anatomy, as shown in FIGS. 59A-B. In practice, the clamp 540 or hook may first be placed in the desired location and position, and then the guide lowered so that the post of the clamp 540 or hook enters the corresponding aperture on the guide. Once the post is positioned through the aperture (as shown in FIGS. 55C and 56C-D), a nut may be threadably connected to the threaded post and tightened to secure the cervical guide against the patient's anatomy.

As described above with thoracolumbar guides, the cervical guides described herein may provide axial or alternatively off-axis trajectories into the patient-specific anatomy. Such an off-axis trajectory may be provided with a sleeve 550 as described above and now shown in FIG. 57. The trajectory may be determined from the use of scanning equipment described above, and selected based on optimal patient anatomy, bone density, etc. The off-axis trajectory may be particularly important in areas of the cervical spine, where the generally smaller vertebrae do not permit the legs or corresponding sleeves to be positioned such that the desired axis of a device, instrument or tool to be used with the guide may be achieved in a co-axial relationship. By providing off-axis trajectories, the guide may serve to secure a device or permit the insertion of a tool or instrument in a direction that could not otherwise be achieved.

The embodiment of the present disclosure depicted in FIGS. 58A-C comprises a patient-specific guide calibration model. The model provides a user with both a visual and tactile representation of the patient anatomy for creating a patient-specific guide, including one or more predetermined screw trajectories. The modeling of predetermined screw trajectories assists in the orientation and placement of patient-matched surfaces and direction of the components of the guide (i.e., legs, sleeves, inserts, etc.). By using the model, a user may also create a non-patient-specific guide that is adjustable and reusable. One example of this could be a surgical guide with hinges, ratchets, swivels, pivots, set screws, etc., that when adjusted or tuned "click" into place and can be locked once the user has finished their adjustments. Then, guide sleeves could be placed over the protruding pegs 560 (as shown in FIGS. 58A-C) to provide the desired drill/tap/screw trajectory, while the rest of the guide could be configured at the user's discretion or to achieve optimal fit with the patient-specific anatomy.

FIGS. 59A-D show another embodiment of a surgical device, which preferably may be use with a procedure involving a patient's cervical spine. According to this embodiment, the device comprises a plurality of sleeves 572 and one or more of the plurality of sleeves 572 may receive a selectively removable clip, for example the clip 574 shown in FIGS. 59C-D. In one embodiment, the selectively removable clips 574 are received by placing a post 573 associated with a clip 574 into a slot 571 in the body of sleeve, as shown in FIG. 59A. This receiving may be a frictional fit, but more preferably is a snapping or latching attachment that prevents undesired removal of the clip 574 once the device has been placed against the patient's anatomy. Other connections within the ordinary skill of those familiar with the art are also contemplated for use with this embodiment.

FIGS. 60A-C include additional views of a device described in the preceding paragraph. FIG. 60A is a side elevation view of the device with at least one clip 574 engaged to the body of the sleeve of the device and further engaged to the underside of an adjacent boney structure. Here, the boney structure is a lamina of a cervical vertebrae, although the clips are contemplated for use with other anatomical features as well. FIG. 60B shows the device with two clips 574', similar to the clips 574' shown in FIG. 59D. FIG. 60C shows details regarding the connection between the clips and the sleeves of the device according to one particular embodiment.

FIGS. 61A-C show yet another embodiment of a guide and associated clips. Here, the clips 575 are preferably spring clips, and are normally biased away from the body of sleeve at the distal end of clips as best seen in FIG. 61A. The connection between clips 575 and sleeves of guide are such that the clips 575 may be depressed against or closer to the body of sleeves, with the normally biasing associated with clips causing resistance to the same. Once depressed, the clips 575 may be inserted beneath adjacent anatomical features as shown in FIGS. 61B-C. In this embodiment, the clips 575 may be oriented so as not to cause unwanted damage to the associated patient anatomy, here, the superior facet joint of a patient's vertebrae. By placing the distal end of the clip 575 in the superior facet complex, the clip 575 may be wedged between the boney anatomy without penetrating the anatomy and otherwise causing damage to the patient. Although the attachment between clips 575 and sleeves is depicted as being a permanent attachment, it is contemplated that the clips 575 of FIGS. 61A-C may be selectively removable as described in the embodiment of FIGS. 59 and 60.

Figures 62A, 62B, 62C:
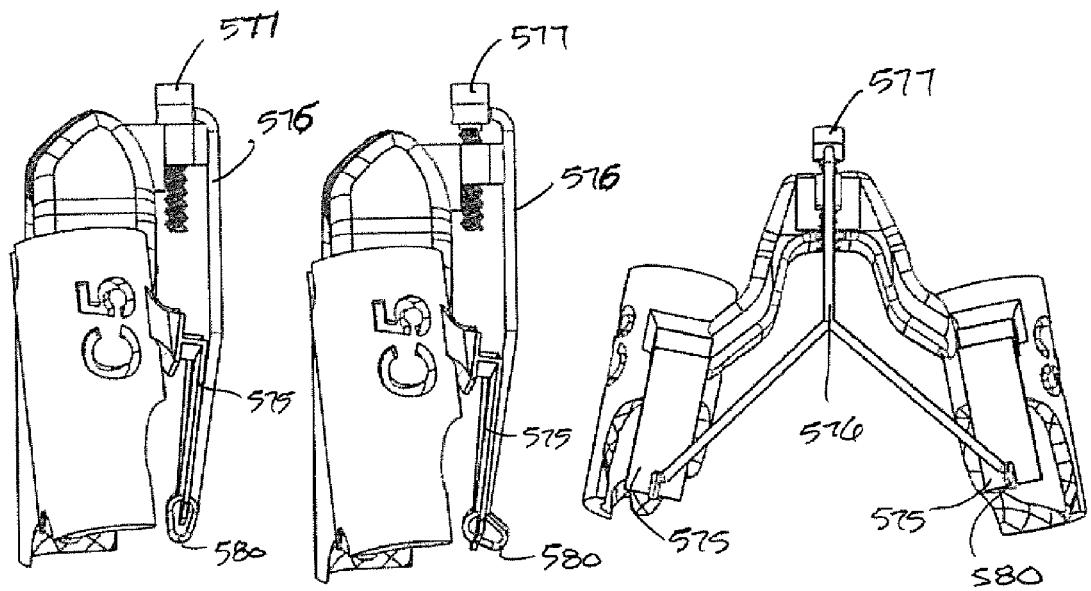

FIGS. 62A-E show views of yet another embodiment of the device of FIGS. 59-61. According to this embodiment, the clips 575 may be selectively coupled to a rigid connector 576 for adjustment relative to the body of the device. According to a preferred embodiment, the adjustment is made by a threaded post 577 inserted into a corresponding threaded bore on a surface of the device, as best shown in FIGS. 62A-B. The positioning of threaded post 577 relative to the device preferably causes rotation of cam elements, which in turn provide secure points of contact about surfaces of the patient's anatomy.

Figures 62D, 62E:
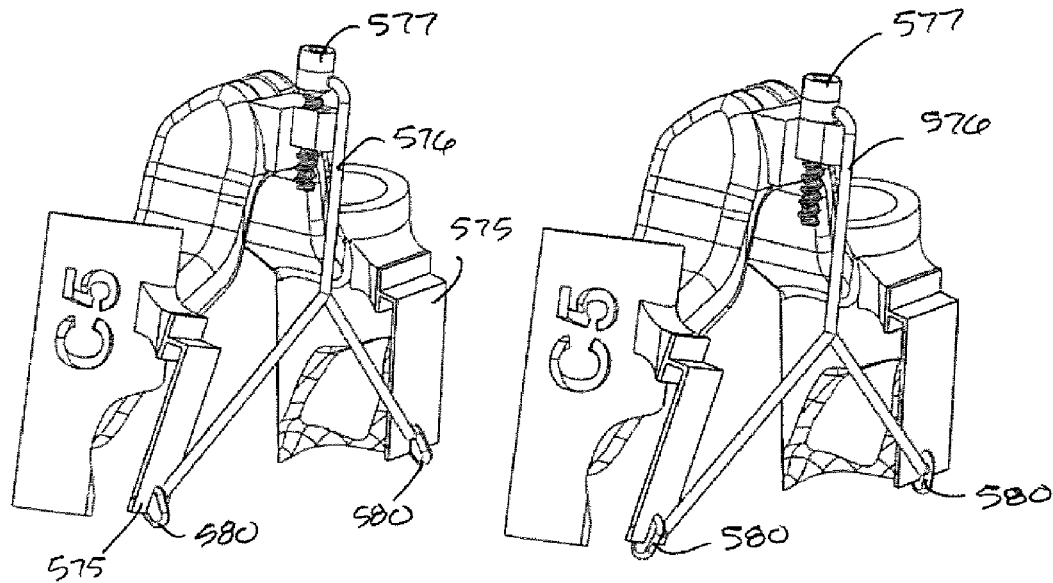

The adjustment of threaded post 577 may also permit a user to selectively engage and disengage distal ends of clips 575 from a patient's anatomical feature. In one embodiment, this adjustment is caused by post 577 and rigid connector 576 to distract clips 575 away from the body of device, as best shown in FIGS. 62B and 62D. Rigid connector 576 may be coupled to each of the plurality of clips 575 as shown in FIGS. 62A-E, which preferably comprises cam elements 580 located at the distal end of each clip. Other connections and orientations of rigid connector 576 are contemplated for use with this embodiment.

Clips described above may be tapered or pointed such that the distal ends of clips contact and penetrate a boney surface of the patient's anatomy. In other embodiments, the clips may further comprise a textured or machined surface, which engages the patient's anatomy and creates a frictional engagement therewith. Other surface variations and geometries may be incorporated into the design of clips for improving the connection to the patient's anatomical features.

The clips are preferably not patient-specific, although they may include patient-specific surfaces is desired. The clips may also be substantially deformable to conform to the variations of patient anatomy. The clips may also be attached, either permanently or selectively, to inserts of the device as opposed to the sleeves of the device as described above.

Figure 63A:
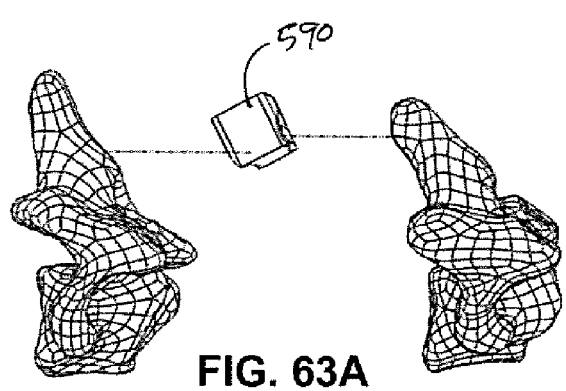
Figure 63B:
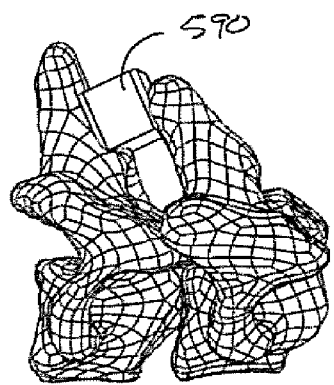
Figure 63C:
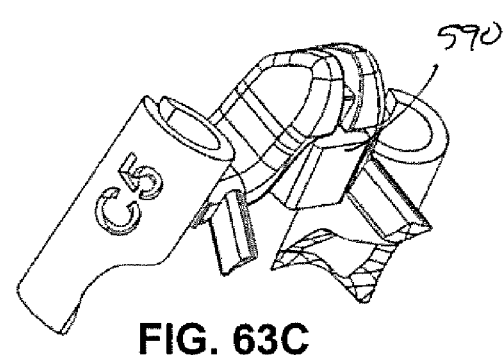
Figure 63D:
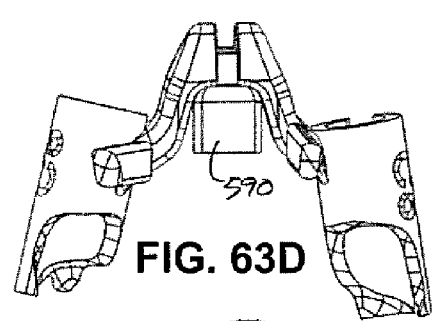
Figure 63E:
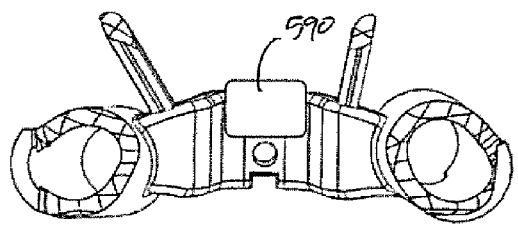
Figure 63F:
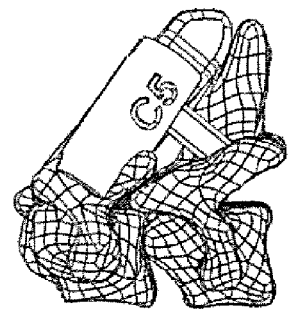
Figure 63G:
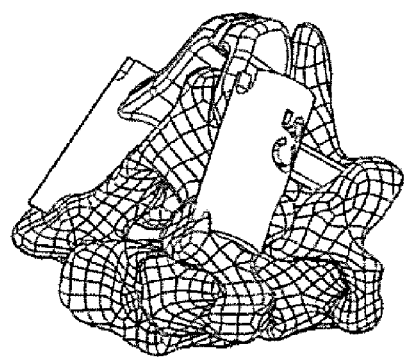
Figure 63H:
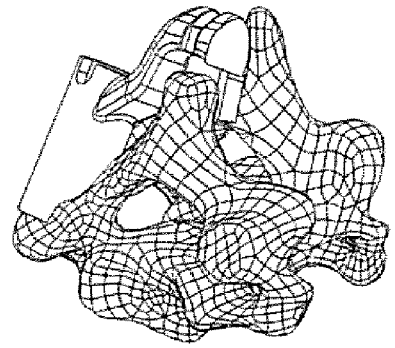

The device in one embodiment may further permit engagement with a spacer, such as the one depicted in FIGS. 63A-H. The spacer 590 may comprise one or more patient-specific surfaces as shown in FIGS. 63A-B, or may be fabricated for use in a variety of different applications. In spine surgery procedures, the spacer 590 permits a device to have patient-specific surfaces about multiple levels of the patient's spine. The spacer 590 is preferably coupled to the device as well, as best shown in FIG. 63C-E. The spacer in this embodiment provides another surface(s) for aligning the device to the desired anatomy and/or orientation of the guide elements described above.

The concepts described above in relation to FIGS. 48-63 have been described for convenience in the context of a cervical spine procedure, but are not limited to application in the cervical spine, and may be applied to thoracolumbosacral spine and ilium as well.

Referring now to FIGS. 64-67, various embodiments according to one aspect of the present disclosure are shown, which relate to the use of guiding wires/pins and cannulated devices, such as screws, and corresponding instruments and/or implants. According to these embodiments, the surgical guides described above may further comprise a "cannulated" system wherein a K-wire or guide pin/wire is placed through one of the sleeves or inserts associated with a patient-specific guide, and any subsequent instruments and/or implants use the wire for guidance into their proper location along the longitudinal axis of the wire.

Referring to FIGS. 64-65, a guide has received instrument sleeves which each have a longitudinal channel for receiving a wire 600, preferably through the center of each insert, which then may be used for centering other instruments and/or implants. As seen in FIG. 66, the instrument sleeves may extend above the top surface of the guide, which in turn may accommodate a longer guide wire 600 and stabilize the wire 600 in the proper location while it is being inserted into the patient's boney anatomy.

Next, the instrument sleeves may be removed as depicted in FIG. 67. If the guide assists the surgeon in performing the surgical procedure, the surgical guide may remain. However, it is contemplated that the guide may be completely removed once the wires 600 are properly seated as shown in FIG. 68.

Once the wires 600 are in place, one or more instruments or implants, such as cannulated screws, may be slidingly received by the wires 600 and thereby placed in the proper position and trajectory. By way of further example but not limitation, a cannulated screw comprising at least one bore therethrough may be positioned on a wire 600 established by the guide depicted in FIG. 64. It is expressly understood that other implants besides cannulated screws may be utilized with these embodiments, as well as a variety of instruments, including those listed above and made part of this disclosure.

Figure 69:
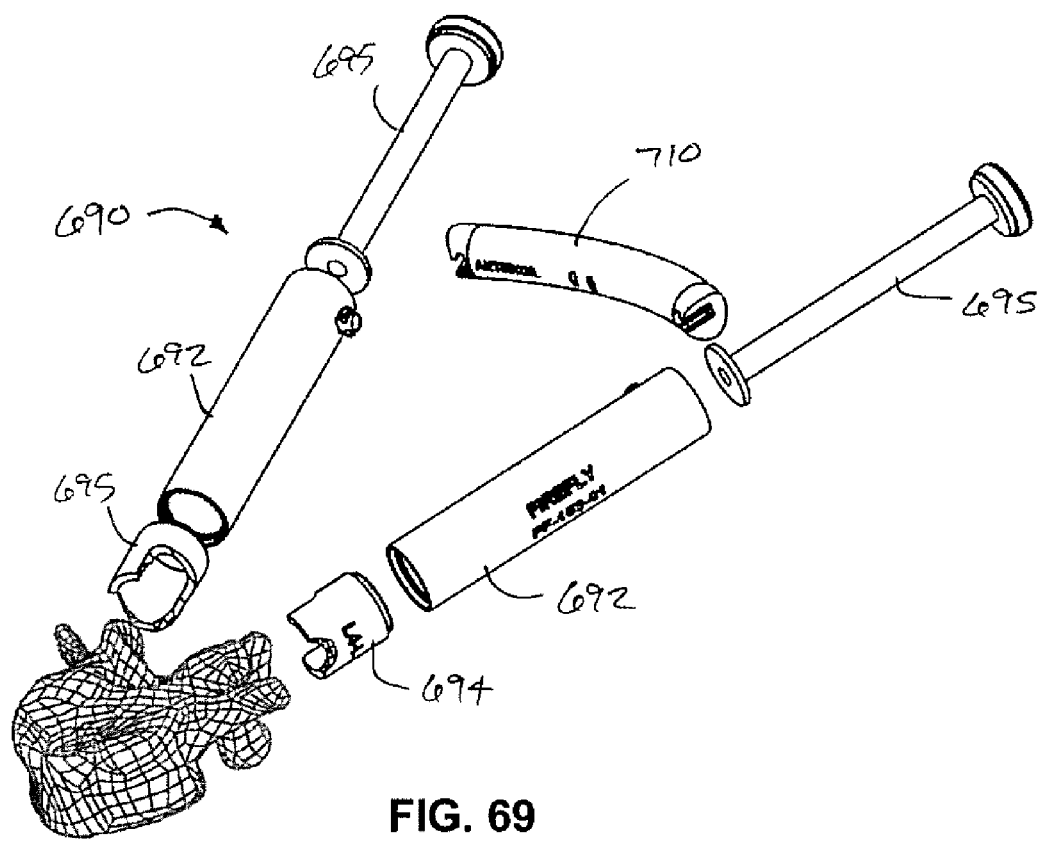
Figure 70A:
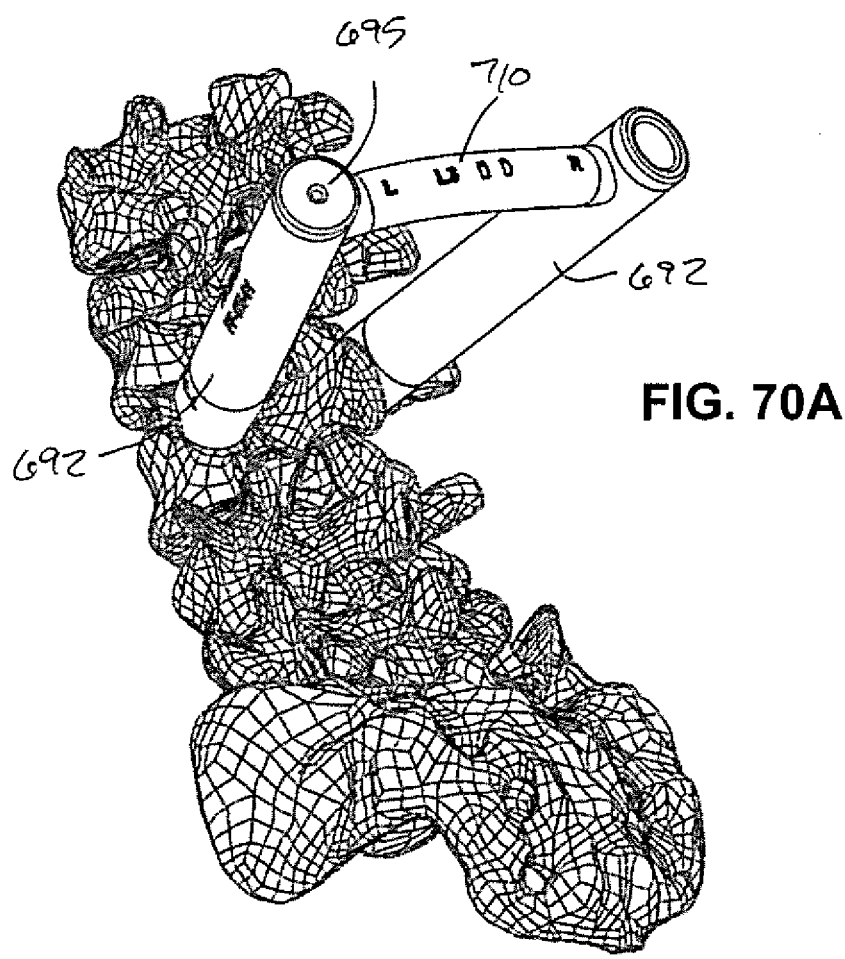
Figure 70B:
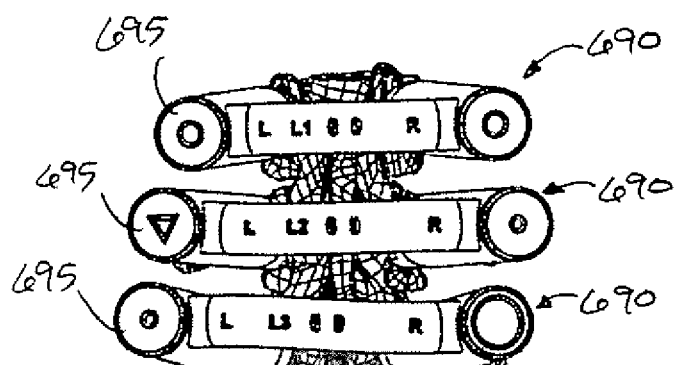
Figure 71:
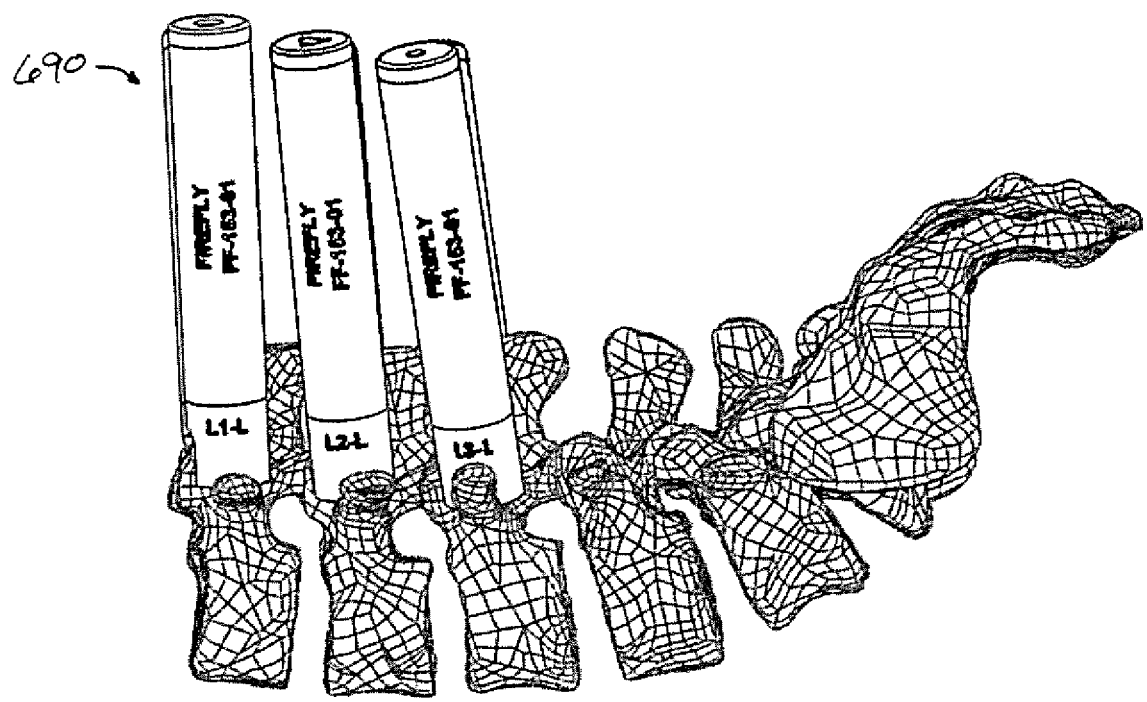
Figure 72:
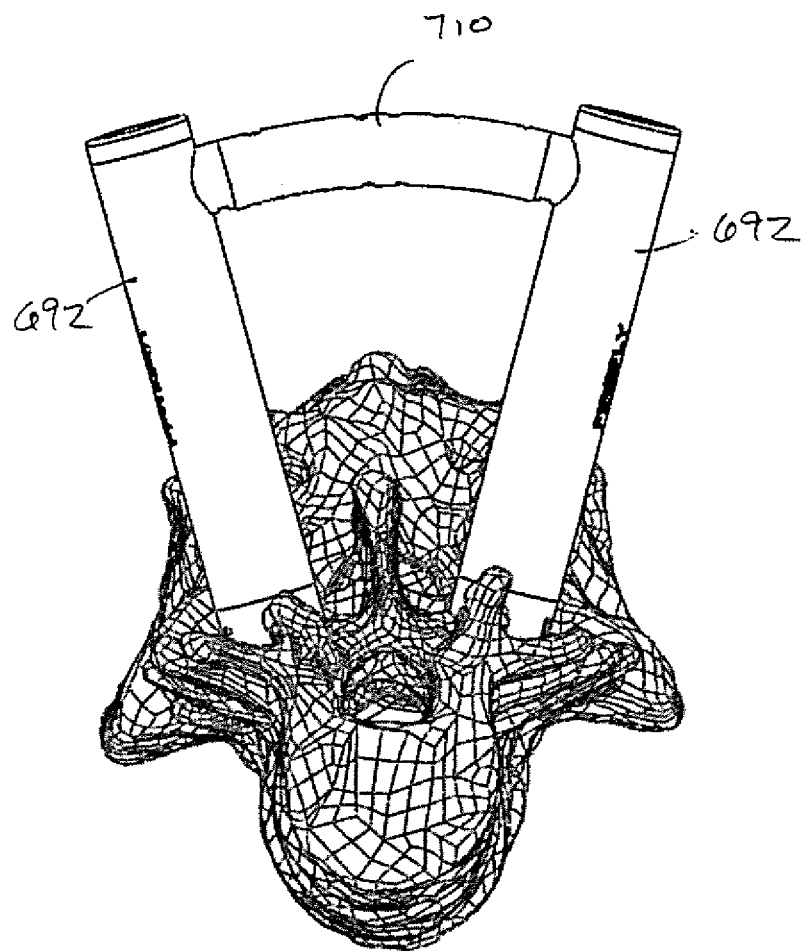
Figure 73:
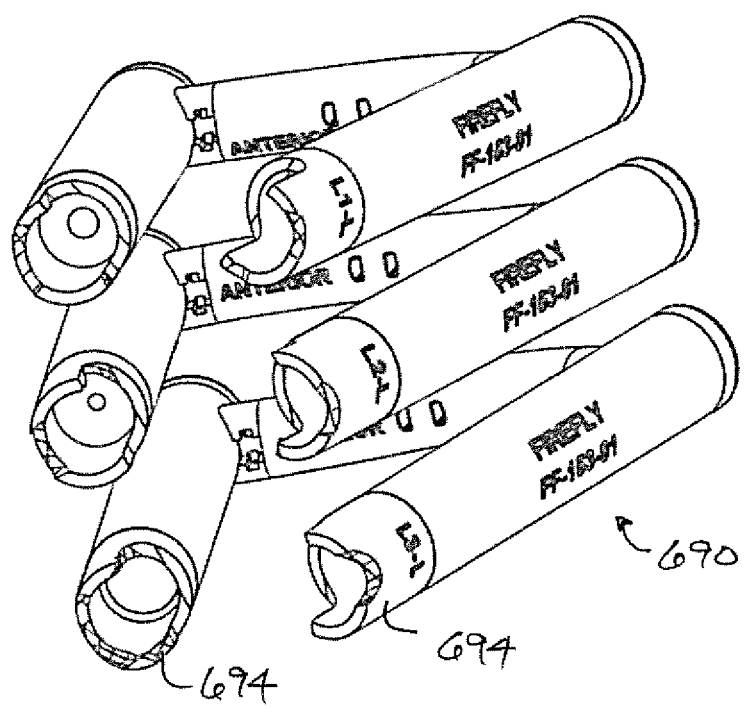

Referring now in detail to FIGS. 69-73, a device is shown for performing MIS procedures on a vertebral body. The device is comprised of a generally cylindrical, hollow retractor 692, which has a first end and a second end. The retractor 692 body is hollow throughout its longitudinal axis, which makes the retractor 692 capable of receiving dilators and progressively expanding retractors as described above and further capable of receiving tools, instruments or devices therethrough, including a custom or standard fabricated insert as shown in FIG. 69. The first end of the retractor 692 is preferably designed to matingly receive one or more patient-specific end-pieces 694, which are also shown in FIG. 69. Retractor 692 may also comprise an attachment joint located preferably along the outer wall of the generally cylindrical body of retractor 692 for receiving a coupling device 710.

Coupling device 710 preferably has a slot or groove on each end for receiving one or more attachment joints. In one embodiment, the attachment joint and slot or groove of a particular coupling device 710 are complementary and create a secure connection when joined. In certain embodiments, the connection between attachment joint and slot or groove of coupling device 710 is such that a desired angle or direction of coupling device is achieved once the joint and slot or groove are mated (as seen best in FIG. 72). In one embodiment, the connection is a locking connection. In another embodiment, the connection is a snap fit connection. In another embodiment, the connection is a frictional engagement between the joint and the slot or groove. For further illustration, see FIGS. 95-97.

Coupling device 710 may be used to secure one or more retractors 692 to one another, and in a preferred embodiment are coupled above the patient's skin surface (i.e., percutaneously). Coupling device 710 may be sized and shaped to secure a first retractor 692 and a second retractor 692 to each other in a desired position. According to yet another embodiment, the coupling device 710 may be secured to one or more retractors 692 to provide a desired orientation or trajectory for related inserts. Coupling device 710 may also be used in a multi-level MIS procedure, and according to at least one embodiment, may be joined to other coupling devices in order to secure both lateral and longitudinal spacing among an array of retractors 692.

Inserts 695 may be of varying shapes and sizes, and may comprise features such as those associated with inserts described above in relation to FIGS. 1-68. Varying views of the apparatus described above are shown in FIGS. 70-73, and include embodiments involving multi-level MIS applications.

Referring now to FIG. 74, an embodiment is shown similar to that of FIGS. 69-73, except coupling device includes multiple channels, which are preferably custom fabricated through the body of coupling device 710, and which may receive one or more alignment elements 695. The alignment elements 695 may be fixation pins, as referred to in FIG. 74, and used to secure the assembly shown in FIG. 74 to a particular boney anatomy. Variations on this embodiment are depicted in FIGS. 86A-C, which include custom fabricated channels oriented to guide alignment elements to penetrate a patient's lamina, facet, pars, spinous process, or other anatomical features. In addition, the channels may be provided in different or multiple locations, such as those shown in FIGS. 87A-B, which provides the benefits described above without requiring a coupling element. In certain embodiments, the use of channels in the coupling element and in the body of the retractor may be combined, as shown in FIGS. 88A-B.

The alignment devices 695 may also comprise a first dimension and a second dimension which provide the surgeon with the ability to gauge the depth of the alignment element. For example, the alignment element 695 may comprise a collar, which is thicker than a first dimension of the alignment element, to stop the penetration of the alignment element 695 into the boney anatomy.

Referring to FIG. 75, another embodiment is shown wherein the assembly further comprises a bridge element 715 for joining two or more coupling elements 711, 712. In this embodiment, the bridge element 715 and coupling elements 711, 712 create a more stable assembly. Also shown in FIG. 75, the inserts for each retractor tube shown comprise different shaped and sized openings for accommodating differing tools, instruments or devices. In this manner, the customized insert may be specific to a particular application associated with a specific retractor tube, and only receive a specific tool, instrument or device.

Referring now to FIGS. 76A-C, an alternative embodiment of a surgical device is shown. In this embodiment, a preferably reusable handle is comprised of a first and a second portion 732, 734, which may be selectively coupled to each other and to the device. This handle is preferably attached to the device in a minimally invasive surgical procedure and provides both alignment and stability to the associated device(s). The handle first and section portions 732, 734 preferably comprise an ergonomic shape for ease of grasping with a single hand of a user, and are preferably offset from the vertical axis of the device(s) to avoid interference with the user's vision during the surgical procedure. Alternatively, the handle portions 732, 734 may be contoured and/or angled to avoid interference with the user's vision. Although a slotted connection is shown in FIGS. 76A-C, other means of connecting the handle portions 732, 734 and the handle to the device(s) are contemplated. In particular, various connection devices described below in FIGS. 95-97 may be incorporated in the embodiment shown in FIGS. 76A-C.

FIGS. 77A-G depict another alternative embodiment of the surgical device comprising one or more optional alignment/depth/position control elements. Here, a handle includes at least a first and a second portion 732, 734, which may be positioned in a plurality of positions relative to one another to adjust the width of the handle. At least one of the first and second portions 732, 734 comprises indicia 744 denoting the width in known dimensions. The device of FIGS. 77A-G preferably comprises at least one rotational adjustment 742, which permits the angle of the handle to vary according to the desired orientation of one or more devices. The handle is preferably coupled to insert(s) which are placed into device(s) (not shown in FIGS. 77A-G). A preferred embodiment also comprises one or more depth control adjustment elements 740, as shown in FIG. 77C. This permits translation of the "legs" of the device. The device preferably includes indicia about the legs reflecting known dimensions for ease of use when adjusting the device for a particular procedure and patient anatomy.

FIGS. 78A-B depict adjustment guides 790, 792, which assist in achieving a desired angular and/or width and/or height adjustment. The adjustment guides 790, 792 preferably couple to the handle or legs of the device and are fixed into place when a desired position or orientation is achieved. For example, the width may be set by placing adjustment guide 790 against handle, as best shown in FIG. 78B, which prevent movement of the handle once the adjustment guide is secured in place. Similarly, an angular adjustment guide 792 serves as a wedge, and prevent greater or lesser rotation of the legs relative to the handle once securely placed against the device (as shown in FIG. 78B).

FIGS. 79A-B include views of a device for assisting in determining the incision and entry portal location for a particular surgical procedure. The device preferably comprises at least one reference element 802, which may be aligned with a known anatomical feature. Here, the feature is the centerline of the patient's spine and/or longitudinal axis of the spinous process. The device further comprises a height, width and angular adjustment 803, 800, 806. The angular adjustment 806 is associated with at least one guide member 804, which may be rotated or pivoted to a desired location according to the user's preference. The guide member 804 is preferably also height adjustable, and may further comprise a distal end including a marking surface, which permits the user to mark a desired location on the patient for future reference. The marking surface may be direct contact, or may be indirect, such as with a laser or other similar optical marking device. FIG. 79B depicts the device according to this embodiment in a final position, whereby the guide member is in the desired location and directed towards the underlying patient anatomy for the associated procedure. FIG. 80 is a detailed view of the device of FIGS. 79A-B.

Referring now to FIGS. 81A-C, another example of an embodiment is provided wherein the connection between attachment joint and slot or groove of coupling device 710 is such that a desired angle or direction of coupling device 710 is achieved once the joint and slot or groove are mated. Reference is again made to previously described FIGS. 69-75. FIGS. 81A-C also depict an embodiment wherein the retractors may be coupled spanning the spinous process and between different levels of a patient's spine. Other variations of this embodiment for use in non-spine procedures in expressly contemplated. Furthermore, as discussed in some detail above, the retractors and coupling elements 710 and bridge elements may also comprise one or more unique indicia which provide a surgeon or other medical professional with identifying information to assure that each component of a particular assembly is assembled in the proper location and joined to the proper apparatus.

In certain applications, it is desirable to provide a surgeon with an expandable retractor tube, such as the embodiment shown in FIGS. 82A-84C. In this embodiment, a collapsed retractor tube 820 in a first orientation is shown in FIG. 82A, and is of a smaller cross-section than a retractor in a second orientation, as shown in FIG. 82B. The retractor of FIG. 82A may be inserted through a smaller incision and mated with a patient-specific anatomical feature. After the retractor 820 is properly positioned, the retractor 820 may be expanded, such as, by way of example but not limitation, through the use of an instrument or tool provided with the retractor 820 (not shown in FIGS. 82A-B). Once the retractor 820 is positioned in its second position, additional instruments, tools, devices or even retractors may be positioned therethrough as shown in FIG. 82C. Referring to the embodiment shown in FIGS. 82A-D, the expandable refractor 820 may further comprise a means for attaching a patient-specific end-piece 825, such as described above in relation to FIGS. 69-73.

Variations on the embodiment described in the preceding paragraph are depicted in FIGS. 83-84. According to these embodiments, the retractor tube is expandable by a plurality of longitudinal hinges placed along the interior circumference of the refractor tube, as best shown in FIG. 84B. The hinges may be mechanical hinges or may be living hinges (i.e., formed from the material of the retractor tube). In other embodiments, variations on the hinge may be incorporated without departing from the novelty of the embodiment described herein. In certain embodiments, the retractor tube is disposable. In other embodiments, the retractor tube is reusable.

Referring now to FIG. 85, inserts provided with refractor tubes described herein may further comprise a longitudinal bore of varying dimension, which in practice permits the safe and effective application of one or more surgical tools or instruments. For example, as shown in FIG. 85, an insert 830 may provide a safety stop or depth control stop 832 by virtue of its geometrical configuration (i.e., preventing the instrument or tool from passing beyond a certain depth within the longitudinal bore of the insert). According to another embodiment, a patient-specific end-piece 834 may provide the ability to prevent an instrument or tool from extending beyond a controlled depth.

Referring now to FIGS. 89A-90C, it is often desirable to provide a coupling 900 between retractors located about multiple levels of a patient's spine when performing a MIS procedure. As shown in FIGS. 89A-B, one embodiment of the present disclosure is to provide such a coupling 900 that further comprises a secondary location for an additional retractor tube 910, which is located between two adjacent retractor tubes. The combination of the two adjacent retractor tubes, including their secure fixation to the patient boney anatomy, and the rigid structure provided by the coupler 900 shown in FIGS. 89A-B provide a well-defined reference point for insertion of an additional retractor 910 through a secondary location between the two positioned retractors. This additional retractor 910 can then be used to perform additional surgical procedures at locations between, for example, two adjacent vertebrae without requiring additional fixation of the retractor to the patient anatomy.

Referring now to FIGS. 91A-92D, various other embodiments are shown relating to the retractor and related elements described above. One embodiment, as shown in FIGS. 91A-D, provides a coupling element 920 which is adjustable. The adjustable features may include, but are not limited to, length, width, height, angle of orientation and depth. In this embodiment, no patient-specific coupling element or bridge needs to be preconfigured, and the adjustable coupling element may be reused. In one embodiment, patient-specific data may be used to provide a surgeon with specific settings for adjusting the adjustable coupling element 920 in a desired setting for use in a particular MIS procedure. This data may be provided before the MIS procedure and included with a specific surgical plan, either with or without any patient customized apparatus.

A variety of mechanical characteristics may be incorporated into the coupling device described above without departing from the spirit of the disclosure made herein. Applicant incorporates by reference U.S. Patent Publication No. 2009/0105760 in its entirety, which is co-pending and names Dr. George Frey as the sole inventor, for the purpose of further supplementing the disclosure and providing additional support for various mechanical characteristics capable of being employed in the coupling device.

Figure 93A:
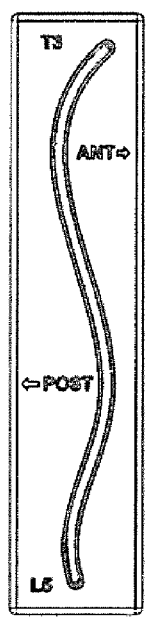
Figure 93B:
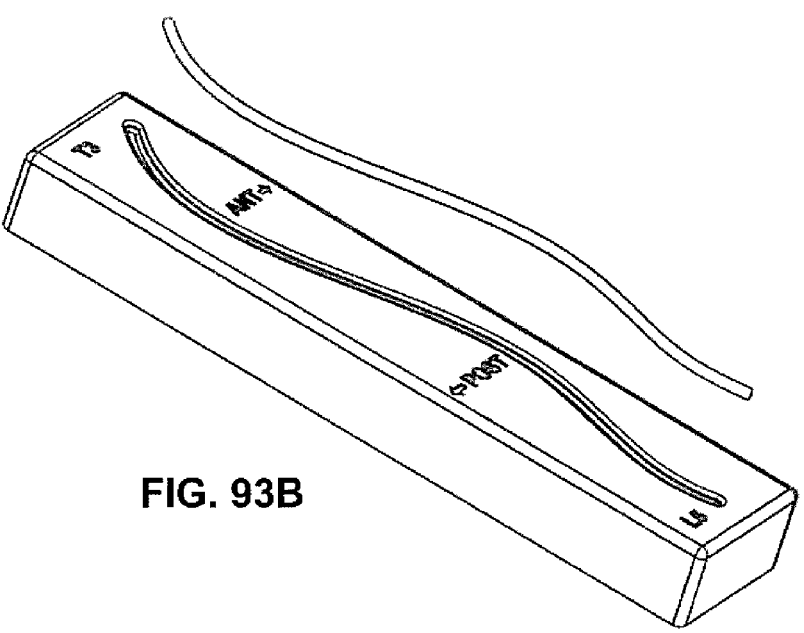
Figure 93C:
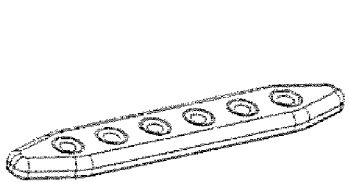
Figure 93D:
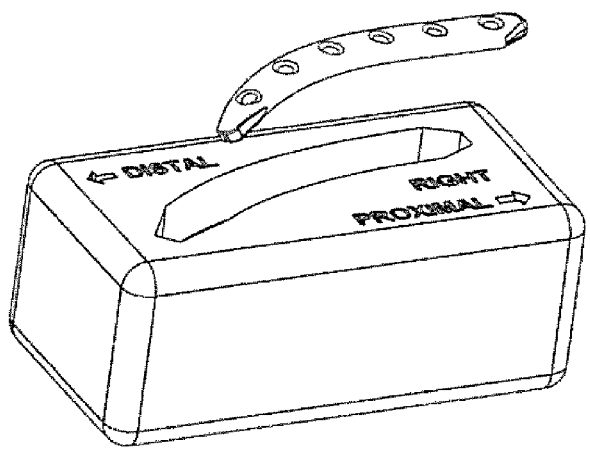

Another embodiment is shown in FIGS. 93A-D, wherein a template of a surgical tool, instrument or device is provided which may be customized or contoured to conform to a specific patient's anatomy. In certain embodiments, the template may provide a surgeon with a particular dimension, shape, orientation, etc. for a device such as a rod, as shown in FIGS. 93A-B. In yet other embodiments, the template may be the device, such as the one shown in FIGS. 93C-D.

FIGS. 94A-C are various views of one embodiment of the present disclosure, which includes a plurality of patient-specific guides. The plurality of guides may receive and be manipulated by an instrument, such as the inserter depicted in FIG. 54B. Alternatively, the plurality of guides may receive a plurality of elongated shafts or "indicators" to assist the user in visualizing the location, orientation, curvature and/or deformity associated with the patient's underlying anatomy. Here, the underlying anatomy is a patient's spine from T10 to L4. The indicators create a visual image of the deformity associated with these levels of the patient's spine. Additionally, the indicators permit a surgeon to determine the length and orientation (including curvature) of a fixation rod or other implant for correcting the deformity or otherwise treating the patient, and may also be captured by an optical system to digitally reproduce the curvature for the purpose of determining correction, rod shape/length, or correct positioning of guides. The indicators may assist the user in other aspects of the surgical procedure. For instance, FIG. 94C shows the plurality of indicators in a side elevation view, which allows the surgeon to visualize the difference in height of each level of the patient's spine and differences from one level to the next. The indicators also allow the user to visualize whether a particular patient-specific guide is misaligned or has become dislodged.

FIGS. 95A-C are side elevation views of a connector for attaching to a sleeve or an insert according to embodiments of the present disclosure. This connector comprises a threaded bore which is received by a threaded post, and is rotationally secured to the post by threaded engagement. This connection type may be used in varying manners, including but not limited to the connection between alignment devices and the surgical guide devices described herein. FIGS. 96A-C show a clamping connector according to another embodiment of the present disclosure. FIGS. 97A-C show a screw or pin connector according to yet another embodiment of the present disclosure. Here, the screw is inserted through a slot in a sleeve element and further inserted through a slot in the distal end of an apparatus associated with the device. For example, the apparatus may include a leg of an alignment device, such as the ones described above.

FIGS. 98A-C are side perspective views of an insert and guide sleeve according to one embodiment of the present disclosure. Here, the insert comprises one reference marking, which may comprise a cut, groove, notch, scoring or other marking for aligning the insert with the desired orientation. The marking is preferably visible with both the naked eye and through fluoroscopy, and may be visible through other known scanning technologies. This embodiment is particular useful for aligning the insert for receiving a cutting or drilling instrument, or for inserting an implant therethrough.

Figure 99A:
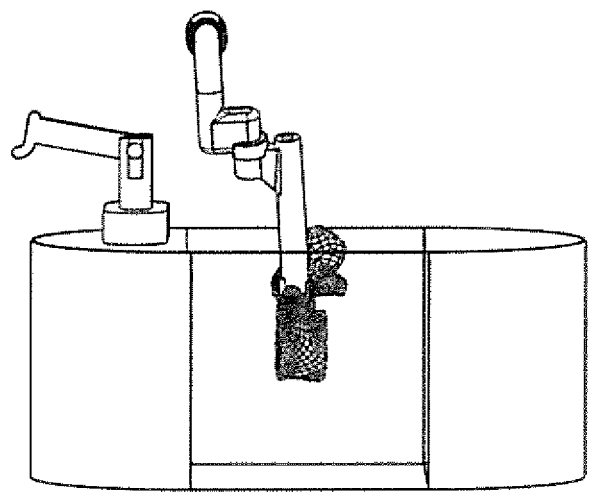
Figure 99B:
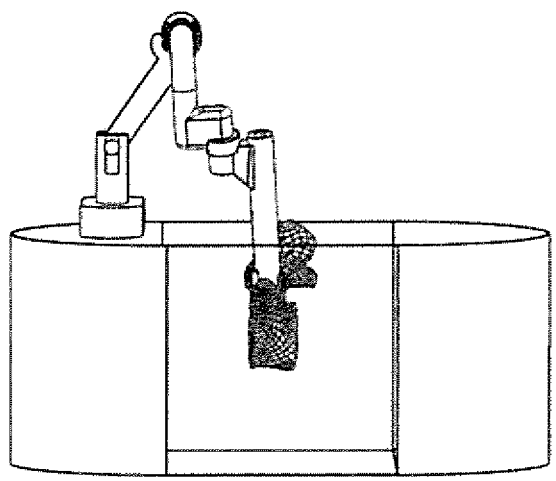
Figure 99C:
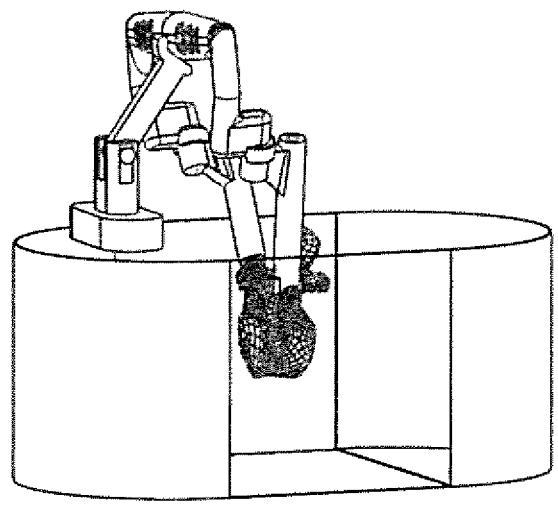

FIGS. 99A-G show various views of a system for aligning a guide according to one of the various embodiments described herein. This system further comprises an adjustable arm assembly, which may be affixed to an operating surface or alternatively to the patient. FIG. 99A shows the arm assembly in a first position away from the device(s), and FIG. 99B shows the arm assembly attached to the device(s), providing stability by resting on the patient's skin. This attachment between the device(s) and the arm assembly may permit a user to set and fix the sagittal angle of the device(s) when performing a surgical procedure on the patient's spine. FIG. 99C shows the embodiment of FIGS. 99A-B in a perspective view.

Figure 99D:
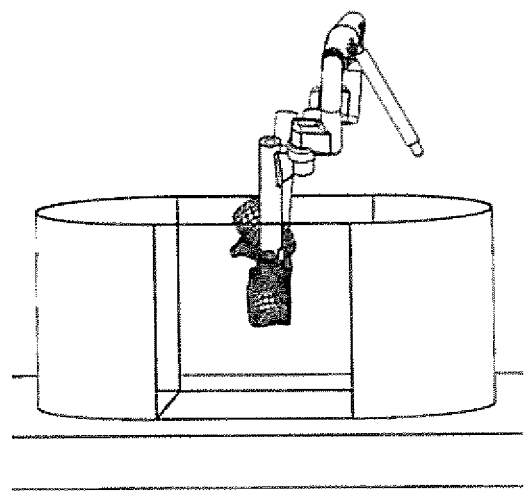
Figure 99E:
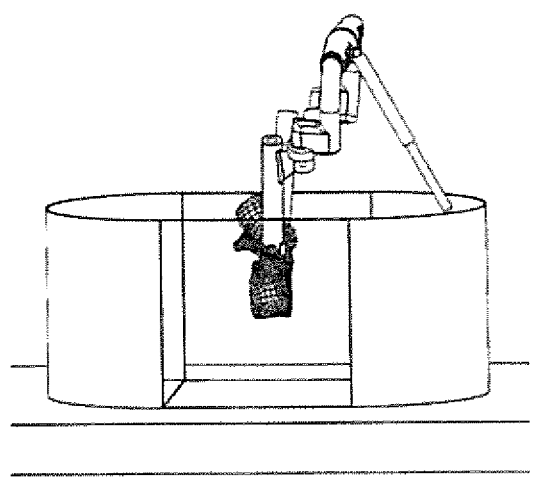
Figure 99F:
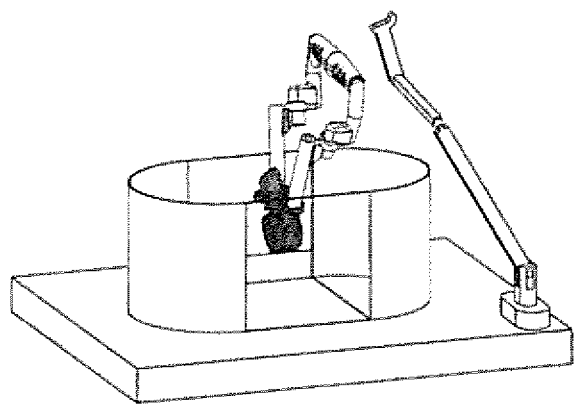
Figure 99G:
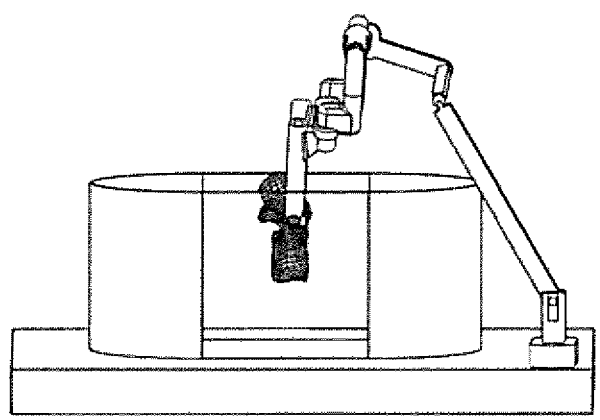
Figure 101A:
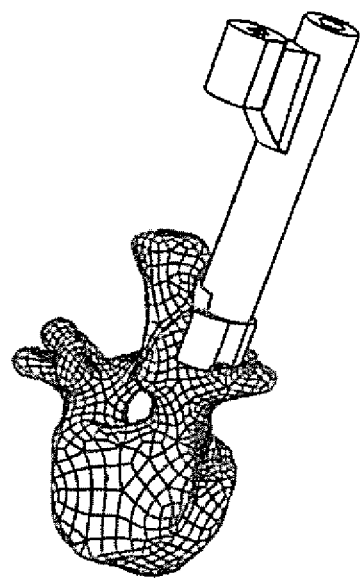
Figure 101B:
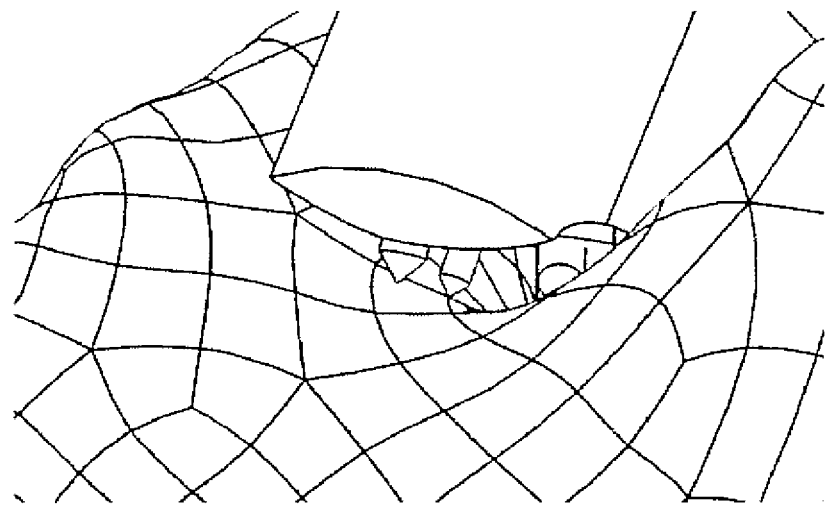
Figure 101C:
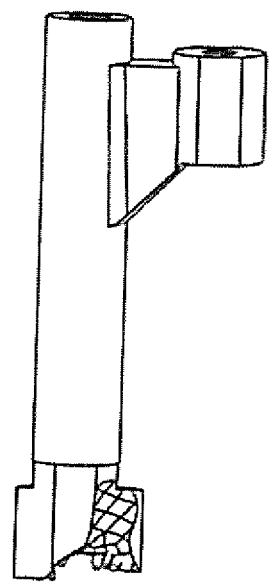
Figure 101D:
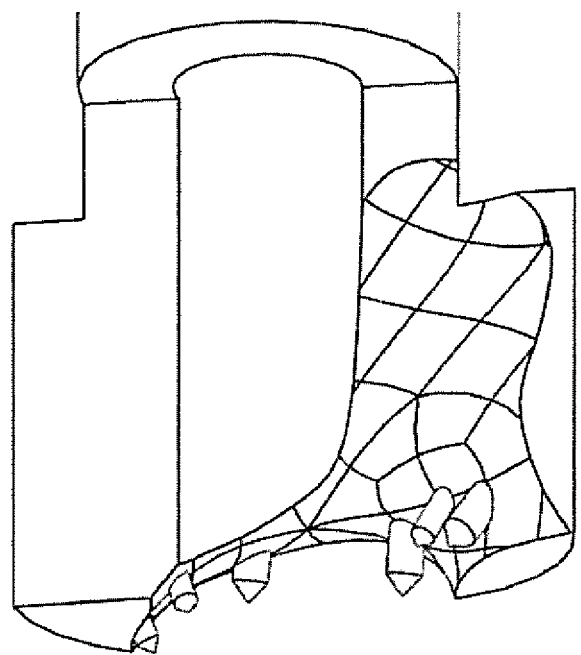

FIGS. 99D-E show an alternative embodiment, wherein the arm assembly comprises a telescoping member that rests on the patient's skin, which may be adjusted to a desired length and angle relative to the associated device(s). This serves to hold the handle of the device(s) in place when the user is not grasping the handle. FIGS. 99F-G depict yet another embodiment of the arm assembly, wherein the assembly is attached to an operating or side table or other horizontal surface. Each of these embodiments preferably includes a locking mechanism for securing the arm assembly components in place once the desired orientation and position has been established.

FIGS. 100A-D are side perspective views of a percutaneous delivery device, according to one embodiment of the present disclosure. The device preferably comprises a distal end having an expandable/retractable tip. When in a first position, as shown in FIG. 100C, the device may be inserted through any of the guides and/or inserts described herein. After insertion, the device may be expanded as shown in FIG. 100D and locked in an expanded position. The shaft of device may further comprise a collar for preventing insertion into the guide and/or insert beyond a desired distance.

FIGS. 101A-D are various views of a patient-specific guide according to yet another alternative embodiment of the present disclosure. In this embodiment, the patient contacting surfaces of the guide further comprise surface contacting elements. These elements may engage soft tissue about the underlying boney surface, for example, and are beneficial for penetrating soft tissue. These elements also provide greater stability and improve haptic feedback, which in turn allow the user to determine whether the guide is in the right location. In a preferred embodiment, the contacting elements are shaped to resemble barbs or blades, although in other embodiments may have varying sharpness, radius, length, and orientation.

Although the devices described above have been illustrated for use with certain guide screws and/or instruments, it is expressly understood that the devices may be used with a variety of other implantable and non-implantable apparatus, including by way of example, medial-to-laterally placed transpedicular screws (commonly referred to as cortical bone trajectory screws). Other screws and instruments may be used with the surgical devices described above without departing from the spirit of the disclosure, and are considered to be within the scope of the appended claims.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

Additionally, although the fusion cages of the present invention are particularly well-suited for implantation into the spinal column between two target vertebrae, and although much of the discussion of the present invention is directed toward their use in spinal applications, advantages offered by embodiments of the present invention may also be realized by implantation at other locations within a patient where the fusion of two or more bony structures may be desired. As one of skill in the art will appreciate, the present invention has applications in the general field of skeletal repair and treatment, with particular application to the treatment of spinal injuries and diseases. It should be appreciated, however that the principles of the present invention can also find application in other areas.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical device for use in a minimally invasive surgical procedure, comprising:
   two or more guides each having a proximal and a distal end, the distal ends each comprising patient-contacting surfaces configured to anatomically mate with and are determined from corresponding subcutaneous anatomical features of a patient;
   a coupling member selectively attachable to the proximal ends of a plurality of the two or more guides, thereby forming a medial portion of the surgical device;

wherein the proximal ends of the two or more guides extend outside of the patient and wherein the coupling member is configured to be selectively attached to at least a first guide and a second guide outside of the patient;

wherein the distal ends of the at least a first and second guides of the surgical device are configured to contact the corresponding subcutaneous anatomical features to ensure proper alignment and placement of the surgical device; and wherein the two or more guides, when coupled with the coupling member, are oriented in a pre-determined direction.

2. The surgical device of claim 1 wherein the two or more guides are configured to receive a bone anchor, an implant, a drill, a rasp, a blade, a screwdriver, a curette, a retractor, a distractor, an elevator or a debridement instrument.

3. The surgical device of claim 1 wherein the two or more guides are substantially cylindrical for use as or in connection with a tubular retractor.

4. The surgical device of claim 1 wherein the device is made of a material selected from the group consisting of a stainless steel, a titanium alloy, an aluminum alloy, a chromium alloy, a PEEK material, a carbon fiber, an ABS plastic, a polyurethane, a resin, a fiber-encased resinous material, a rubber, a latex, a synthetic rubber, a polymer, and a natural material.

5. A surgical device formed by anatomical data for a specific patient, comprising:
   a medial body of the surgical device, the medial body having a proximal and a distal end;
   at least one patient-specific element selectively coupled to the distal end of the medial body and configured to be positioned on a patient-specific subcutaneous anatomical feature corresponding to the patient-specific element;
   the medial body further comprising a central bore configured to receive at least one insert;
   the at least one insert selectively positioned within the medial body of the surgical device, the at least one insert comprising an aperture for receiving an instrument or implant;
   wherein the aperture of the at least one insert is customized to receive an instrument or advance an implant by a predetermined distance.

6. The surgical device according to claim 5 further comprising at least one coupling member selectively attachable to the proximal end of the medial body of the surgical device and at least one additional surgical device.

7. The surgical device according to claim 6, wherein the surgical device is identifiable by optical or electronic recognition means, which facilitates verification of the location and orientation of the surgical device relative to the patient-specific anatomical feature.

8. The surgical device according to claim 5, wherein the surgical device further comprises a plurality of surfaces configured for operatively associating the surgical device with the at least one additional surgical device, which in combination facilitate alignment and orientation of the surgical device and the at least one additional surgical device with the patient-specific anatomical feature.

9. The surgical device according to claim 8, wherein the at least one additional surgical device is designed to remain with a patient, and is selected from the group consisting of a bone anchoring device, an implantable device, a cage, a plate and a bioactive device.

10. The surgical device of claim 5, wherein the medial body comprises a central bore with a patient-matching surface.

11. An orthopedic device for use in a minimally invasive surgical procedure, comprising: a first patient-specific element configured to at least one patient-specific surface determined from a patient's anatomy and which anatomically conforms to at least a first subcutaneous anatomic feature of a specific patient; a second patient-specific element configured to at least one second patient-specific surface determined from a patient's anatomy and which anatomically conforms to at least a second subcutaneous anatomic feature of a specific patient; and an arcuate bridge coupling the first and second patient-specific elements, the arcuate bridge configured to be selectively engaged with the first and second patient-specific elements at a location beyond the patient's anatomy.

12. The orthopedic device of claim 11, further comprising first and second patient-specific bores passing through the corresponding first and second patient-specific elements and having patient-specific-orientations for guiding one or more fixation devices into the corresponding first and second anatomic portions of the patient.

13. The orthopedic device of claim 11, wherein in the first and second patient-specific surfaces correspond to first and second transverse processes of a vertebra of the patient.

14. The orthopedic device of claim 11, wherein the arcuate bridge further permits a user to verify proper placement and alignment of the first and second patient-specific elements.

15. The orthopedic device of claim 11, wherein the first and second patient-specific surfaces each anatomically mate with at least one contour of the lamina or inferior articular process of one or more vertebrae.

16. The orthopedic device of claim 11, wherein the device is configured to be used on one or more vertebrae of a patient.

17. The orthopedic device of claim 11, wherein the device may be selectively coupled to one or more additional orthopedic devices for mating with multiple anatomic features of a patient.

18. The orthopedic device of claim 12, wherein the first and second patient-specific bores are oriented along pre-determined trajectories determined from the anatomical features of the patient.

19. The orthopedic device of claim 17, wherein the device may be arranged in a monolithic or multi-level configuration for spanning multiple vertebrae of the patient.

* * * * *